(12) United States Patent
Deshpande et al.

(10) Patent No.: US 7,538,221 B2
(45) Date of Patent: May 26, 2009

(54) POLYMORPHS OF RACEMIC, DEXTROROTATORY, AND LEVOROTATORY ENANTIONERS OF 1-CYCLOPROPYL-6-FLUORO-8-METHOXY-7-(4-AMINO-3,3-DIMETHYLPIPERIDIN-1-YL)-1,4-DIHYDRO-4-OXO-QUINOLINE-3-CARBOXYLIC ACID HYDROCHLORIDE AND MESYLATE SALTS

(75) Inventors: Prasad Keshav Deshpande, Aurangabad (IN); Satish Baliram Bhavsar, Aurangabad (IN); Yati Chugh, Aurangabad (IN); Ravindra Dattatrya Yeole, Aurangabad (IN); Noel John De Souza, Mumbai (IN); Mahesh Vithalbhai Patel, Aurangabad (IN)

(73) Assignee: The Company of Wockhardt Limited, Mumbai-51 (IN)

( * ) Notice: Subject to any disclaimer, the term of this patent is extended or adjusted under 35 U.S.C. 154(b) by 315 days.

(21) Appl. No.: 10/578,371

(22) PCT Filed: Nov. 10, 2004

(86) PCT No.: PCT/IN2004/000347

§ 371 (c)(1),
(2), (4) Date: Aug. 21, 2006

(87) PCT Pub. No.: WO2005/066154

PCT Pub. Date: Jul. 21, 2005

(65) Prior Publication Data

US 2007/0082926 A1    Apr. 12, 2007

(30) Foreign Application Priority Data

Nov. 20, 2003    (IN) .................. 1199/MUM/2003

(51) Int. Cl.
*C07D 215/38*    (2006.01)
*A61K 31/44*    (2006.01)

(52) U.S. Cl. ............... 546/160; 546/156; 546/159; 514/253.08; 514/313

(58) Field of Classification Search ............... 546/156, 546/159, 160; 514/253.08, 313
See application file for complete search history.

(56) References Cited

U.S. PATENT DOCUMENTS 6,878,713 B2 * 4/2005 De Souza et al. ...... 514/253.08
6,964,966 B2 * 11/2005 De Souza et al. ...... 514/253.08
7,393,957 B2 * 7/2008 De Souza et al. ........... 546/156

FOREIGN PATENT DOCUMENTS

WO    WO03/050107 A    6/2003

OTHER PUBLICATIONS

D. J. W. Grant, Theory and Origin of Polymorphism. In H. G. Brittain (ed.) Polymorphism in Pharmaceutical Solids, Marcel Dekker, Inc, New York, 1999, pp. 1-34.

* cited by examiner

*Primary Examiner*—D. Margaret Seaman
(74) *Attorney, Agent, or Firm*—Bio Intellectual Property Service (Bio IPS) LLC; O. M. Sam Zaghmout

(57) ABSTRACT

A polymorphic forms of the hydrochloride salt and mesylate salt of racemic (±)-1-cyclopropyl-6-fluoro-8-methoxy-7-(4-amino-3,3-dimethylpiperidin-1-yl)-1,4-dihydro-4-oxo-quinoline-3-carboxylic acid, dextrorotatory R-(+)-1-cyclopropyl-6-fluoro-8-methoxy-7-(4-amino-3,3-dimethylpiperidin-1-yl)-1,4-dihydro-4-oxo-quinoline-3-carboxylic acid and S-(−)-1-cyclopropyl-6-fluoro-8-methoxy-7-(4-amino-3,3-dimethylpiperidin-1-yl)-1,4-dihydro-4-oxo-quinoline-3-carboxylic acid having formula (I) and (II) respectively are described. Processes for their preparation are also described. The invention further relates to methods of using, and pharmaceutical compositions comprising the compounds of the invention for treatment of bacterial infections in mammals.

24 Claims, 38 Drawing Sheets

1) Heat from 30.00°C to 300.00°C at 10.00°C/min

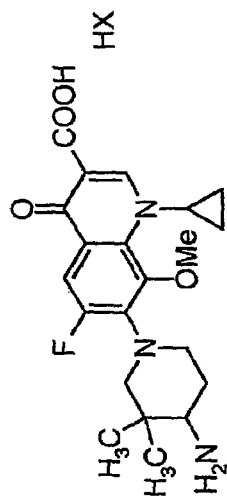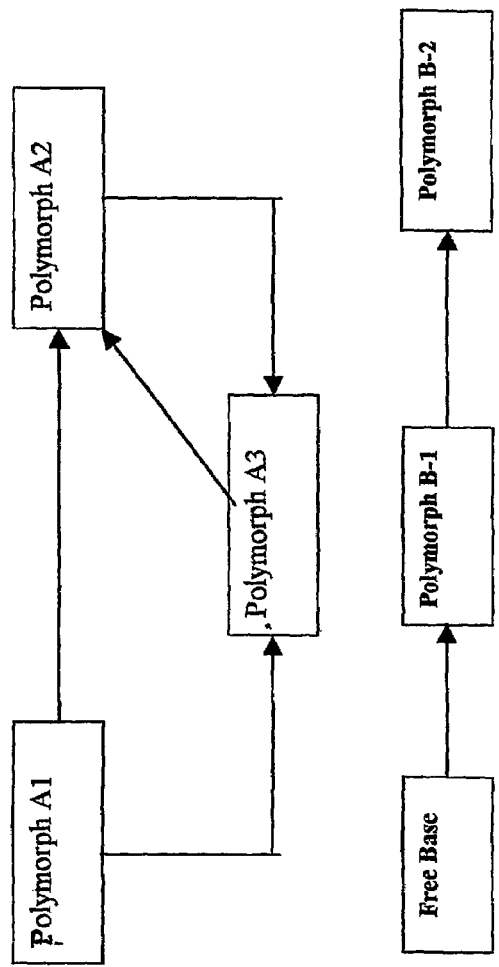
FIG - 37

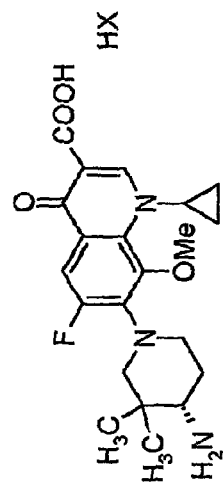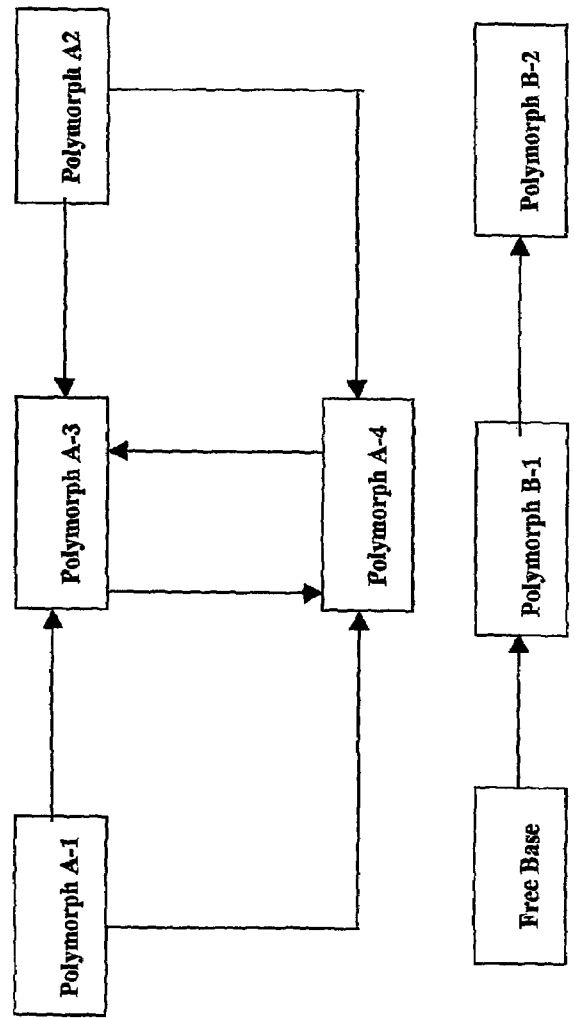
FIG - 38

POLYMORPHS OF RACEMIC, DEXTROROTATORY, AND LEVOROTATORY ENANTIONERS OF 1-CYCLOPROPYL-6-FLUORO-8-METHOXY-7-(4-AMINO-3,3-DIMETHYLPIPERIDIN-1-YL)-1,4-DIHYDRO-4-OXO-QUINOLINE-3-CARBOXYLIC ACID HYDROCHLORIDE AND MESYLATE SALTS

FIELD OF THE INVENTION

The present invention relates to ten novel polymorphs which are identified as (±) A-3, (±) B-1, (±) B-2, (+) A-3, (+) B-1, (+) B-2, (−) A-3, (−) A-4, (−) B-1 and (−) B-2.

Polymorphs are designated A-3 for the respective hydrochloride salts of racemic (±)-1-cyclopropyl-6-fluoro-8-methoxy-7-(4-amino-3,3-dimethylpiperidin-1 -yl)-1,4-dihydro-4-oxo-quinoline-3-carboxylic acid, dextrorotatory isomer R-(+)-1-cyclopropyl-6-fluoro-8-methoxy-7-(4-amino-3,3-dimethylpiperidin-1-yl)-1,4-dihydro-4-oxo-quinoline-3-carboxylic acid, and levorotatory isomer S-(−)-1-cyclopropyl-6-fluoro-8-methoxy-7-(4-amino-3,3-dimethylpiperidin-1-yl)-1,4-dihydro-4-oxo-quinoline-3-carboxylic acid and A-4 for the hydrochloride salt of the levorotatory isomer S-(−)-1-cyclopropyl-6-fluoro-8-methoxy-7-(4-amino-3,3-dimethylpiperidin-1-yl)-1,4-dihydro-4-oxo-quinoline-3-carboxylic acid.

The present invention also relates to polymorphs designated B-1 and B-2 for the respective mesylate salts of racemic (±)-1-cyclopropyl-6-fluoro-8-methoxy-7-(4-amino-3,3-dimethylpiperdin-1-yl)-1,4-dihydro-4-oxo-quinoline-3-carboxylic acid, dextrorotatory isomer R-(+)-1-cyclopropyl-6-fluoro-8-methoxy-7-(4-amino-3,3-dimethylpiperidin-1-yl)-1,4-dihydro-4-oxo-quinoline-3-carboxylic acid and levorotatory isomer S-(−)-1-cyclopropyl-6-fluoro-8-methoxy-7-(4-amino-3,3-dimethylpiperidin-1-yl)-1,4-dihydro-4-oxo-quinoline-3-carboxylic acid.

The invention also relates to processes for the preparation of the polymorphs, to pharmaceutical compositions made using and/or incorporating them and to the use of the polymorphs as antimicrobials.

Polymorphs A-3 of the respective hydrochloride salts of racemic (±)-1-cyclopropyl-6-fluoro-8-methoxy-7-(4-amino-3,3-dimethylpiperidin-1-yl)-1,4-dihydro-4-oxo-quinoline-3-carboxylic acid, dextrorotatory isomer R-(+)-1-cyclopropyl-6-fluoro-8-methoxy-7-(4-amino-3,3-dimethylpiperidin-1-yl)-1,4-dihydro-4-oxo-quinoline3-carboxylic acid, and levorotatory isomer S-(−)-1-cyclopropyl-6-fluoro-8-methoxy-7-(4-amino-3,3-dimethylpiperidin-1-yl)-1,4-dihydro-4-oxo-quinoline-3-carboxylic acid, polymorph A-4 of the respective hydrochloride salt of levorotatory isomer S-(−)-1-cyclopropyl-6-fluoro-8methoxy-7-(4-amino-3,3-dimethylpiperidin-1-yl)-1,4-dihydro-4-oxo-quinoline-3-carboxylic acid, and polymorphs B-1 and B-2 of the respective mesylate salts of racemic (±)-1-cyclopropyl-6-fluoro-methoxy-7-(4-amino-3,3-dimethylpiperidin-1-yl)-1,4-dihydro-4-oxo-quinoline-3-carboxylic acid, dextrorotatory isomer R-(+)-1-cyclopropyl-6fluoro-8-methoxy-7-(4-amino-3,3-dimethylpiperidin-1-yl)-1,4-dihydro-4-oxo-quinoline-3-carboxylic acid and levorotatory isomer S-(−)-1-cyclopropyl-6-fluoro-8-methoxy-7-(4-amino-3,3-dimethylpiperidin-1-yl)-1,4-dihydro-4-oxo-quinolin-3-carboxylic acid are hereinafter referred to as "the compound/s of the invention".

BACKGROUND OF THE INVENTION

The fluoroquinolones, 1-cyclopropyl-6-fluoro-8-methoxy-7-(4-amino-3,3-dimethylpiperidin-1-yl)-1,4-dihydro-4-oxo-quinoline3-carboxylic acid hydrochloride and 1-cyclopropyl-6-fluoro-8-methoxy-7-(4amino-3,3-dimethylpiperidin-1-yl)-1,4-dihydro-4-oxo-quinoline-3-carboxylic acid methane sulfonate ("methane sulfonate" being also termed as "mesylate") having the formulae I and II

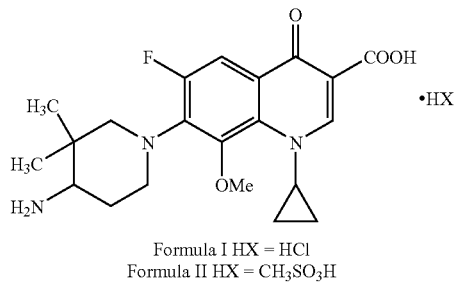

Formula I HX = HCl
Formula II HX = CH$_3$SO$_3$H are described in our pending U.S. Patent Application publication Nos. 2003/0096812 and 20030216568 and WO Application publication Nos. 02/085886 and 03/050107. Racemic and optically active enantiomeric forms of 1-cyclopropyl-6-fluoro-8methoxy-7-(4-amino-3,3-dimethylpiperidin-1-yl)-1,4-dihydro-4-oxo-quinoline-3-carboxylic acid are described in these US patent applications and WO applications.

The processes for preparing the respective hydrochloride and methane sulfonate salts of the racemic mixture and optical enantiomers of 1-cyclopropyl-6-fluoro-8-methoxy-7-(4-amino-3,3-dimethylpiperidin-1-yl)-1,4-dihydro-4-oxo-quinoline-3-carboxylic acid are described in our pending US patent application publication No. 2003/0096812 (the '812 application). The respective polymorphs A-1 and A-2 of the hydrochloride salt forms of the racemic mixture and enantiomeric isomers of 1-cyclopropyl-6-fluoro-8-methoxy-7-(4-amino-3,3-dimethylpiperidin-1-yl)-1,4-dihydro-4-oxo-quinoline-3carboxylic acid hydrochloride are also described in US application publication No. 2003/0216568 and corresponding WO application publication 03/050107.

Additionally, polymorphic forms A-3 and A-4 of levorotatory isomer S-(−)-1-cyclopropyl-6-fluoro-8-methoxy-7-(4-amino-3,3-dimethylpiperidin-1-yl)-1,4-dihydro4-oxo-quinoline-3-carboxylic acid hydrochloride are described in our co-pending Indian patent application No. 1199/MUM/2003 and U.S. application No. 60/523,872, from which this application claims priority, both of which are completely incorporated herein by reference.

According to our pending US patent application publication No. 2003/0216568 (the '568 application), the levorotatory enantiomer S-(−)-1-cyclopropyl-6-fluoro-8-methoxy-7-(4-amino-3,3-dimethylpiperidin-1-yl)-1,4-dihydro-4-oxo-quinoline3-carboxylic acid hydrochloride is produced by the method of the '812 application. On dissolution in methanol and cooling, a polymorph designated A-1 having a crystalline form is obtained, and the polymorph is characterized by Powder X-ray diffraction spectroscopy, infrared spectroscopy and differential scanning calorimetry. The '568 application also describes a second polymorph designated A-2 having a crystalline form prepared by dissolving the levorotatory S-(−)-1-cyclopropyl-6-fluoro-8-methoxy-7-(4-amino-3,3-dimethylpiperidin-1-yl)-1,4-dihydro-4-oxo-quinoline-3-carboxylic acid hydrochloride in 50% aqueous isopropanol and subsequent cooling. The A-2 crystalline polymorph being characterized by Powder X-ray diffraction spectroscopy, infrared spectroscopy and differential scanning calorimetry.

Although our co-pending US patent application publication Nos. '812 and '568 describe mesylate salts of the racemic mixture and optical enantiomers of 1-cyclopropyl-6-fluoro-8-methoxy-7-(4-amino-3,3-dimethylpiperidin-1-yl)-1,4-dihydro4-oxo-quinoline-3-carboxylic acid, the applications do not describe that the mesylate salts can exist in more than one polymorphic form.

We have now found novel pharmaceutically suitable hydrochloride salt polymorphic forms (designated A-3) and methane sulfonate salt polymorphic forms (designated B-1 and B-2) of the racemic mixture (±)-1-cyclopropyl-6-fluoro-8-methoxy-7-(4-amino-3,3-dimethylpiperidin-1-yl)-1,4-dihydro-4-oxo-quinoline-3-carboxylic acid, dextrorotatory isomer R-(+)-1-cyclopropyl-6-fluoro-8-methoxy-7-(4-amino-3,3-dimethylpiperidin-1-yl)-1,4-dihydro-4-oxo-quinoline-3-carboxylic acid, and S-(−)-1-cyclopropyl-6-fluoro-8-methoxy-7-(4-amino-3,3-dimethylpiperidin-1-yl)-1,4-dihydro-4-oxo-quinoline-3-carboxylic acid and additionally polymorph A-4 of hydrochloride salt of the S-(−)-1-cyclopropyl-6-fluoro-8-methoxy-7-(4-amino-3,3-dimethylpiperidin-1-yl)-1,4-dihydro-4-oxo-quinoline-3-carboxylic acid, and novel processes to prepare and isolate them.

These polymorphic forms A-3, A-4, B-1 and B-2 also have antibacterial activity. The compounds disclosed in our co-pending US patent application publications Nos. 2003/0096812 and 2003/0216568 also have antibacterial activity.

SUMMARY OF THE INVENTION

The present invention relates to novel polymorphs of (±)-1-cyclopropyl-6-fluoro-8-methoxy-7-(4-amino-3,3-dimethylpiperidin-1-yl)-1,4-dihydro-4-oxo-quinoline-3-carboxylic acid hydrochloride, R-(+)-1-cyclopropyl-6-fluoro-8-methoxy-7-(4-amino-3,3-dimethylpiperidin-1-yl)-1,4-dihydro-4-oxo-quinoline-3-carboxylic acid hydrochloride and S-(−)-1-cyclopropyl-6-fluoro-8-methoxy-7-(4-amino-3,3-dimethylpiperidin-1-yl)-1,4-dihydro-4-oxo-quinoline-3-carboxylic acid hydrochloride identified as polymorphs A-3 and A-4, the polymorphs having formula I, and to novel polymorphs of (±)-1-cyclopropyl-6-fluoro-8-methoxy-7-(4-amino-3,3-dimethylpiperidin-1-yl)-1,4-dihydro-4-oxo-quinoline-3-carboxylic acid mesylate, R-(+)-1-cyclopropyl-6-fluoro-8-methoxy-7-(4-amino-3,3-dimethylpiperidin-1-yl)-1,4-dihydro-4-oxo-quinoline-3-carboxylic acid mesylate and S-(−)-1-cyclopropyl-6-fluoro-8-methoxy-7-(4-amino-3,3-dimethylpiperidin-1-yl)-1,4dihydro-4-oxo-quinoline-3-carboxylic acid mesylate identified as polymorphs B-1 and polymorph B-2 thereof, having formula II.

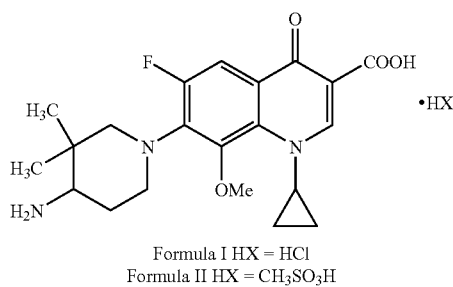

Formula I HX = HCl
Formula II HX = CH$_3$SO$_3$H

The present invention also relates to pharmaceutical compositions comprising one or more of polymorphs A-3, A-4, B-1, and B-2 and methods for using the polymorphs and compositions comprising the polymorphs. The present invention also relates to methods for preparation of the polymorphs.

The antibacterial activity of polymorphs A-1 and A-2 of the hydrochloride salt is described in our co-pending US patent application publications Nos. 2003/0096812 and 2003/0216568. The antibacterial activity of the polymorphic forms A-3 and A-4 of the hydrochloride salts, and of the polymorphic forms B-1 and B-2 of the mesylate salts is described herein and in our co-pending Indian patent application No. 11199/MUM/2003 and U.S. application No. 60/523,872.

BRIEF DESCRIPTION OF THE DRAWINGS

The invention will now be described in further detail with reference to the accompanying drawings.

FIG. 37 shows processes for preparing polymorphic forms A-3, B-1 and B-2.

FIG. 38 shows processes for preparing polymorphic forms A-3, A4, B-1 and B2.

DETAILED DESCRIPTION OF THE INVENTION

Figure 1:
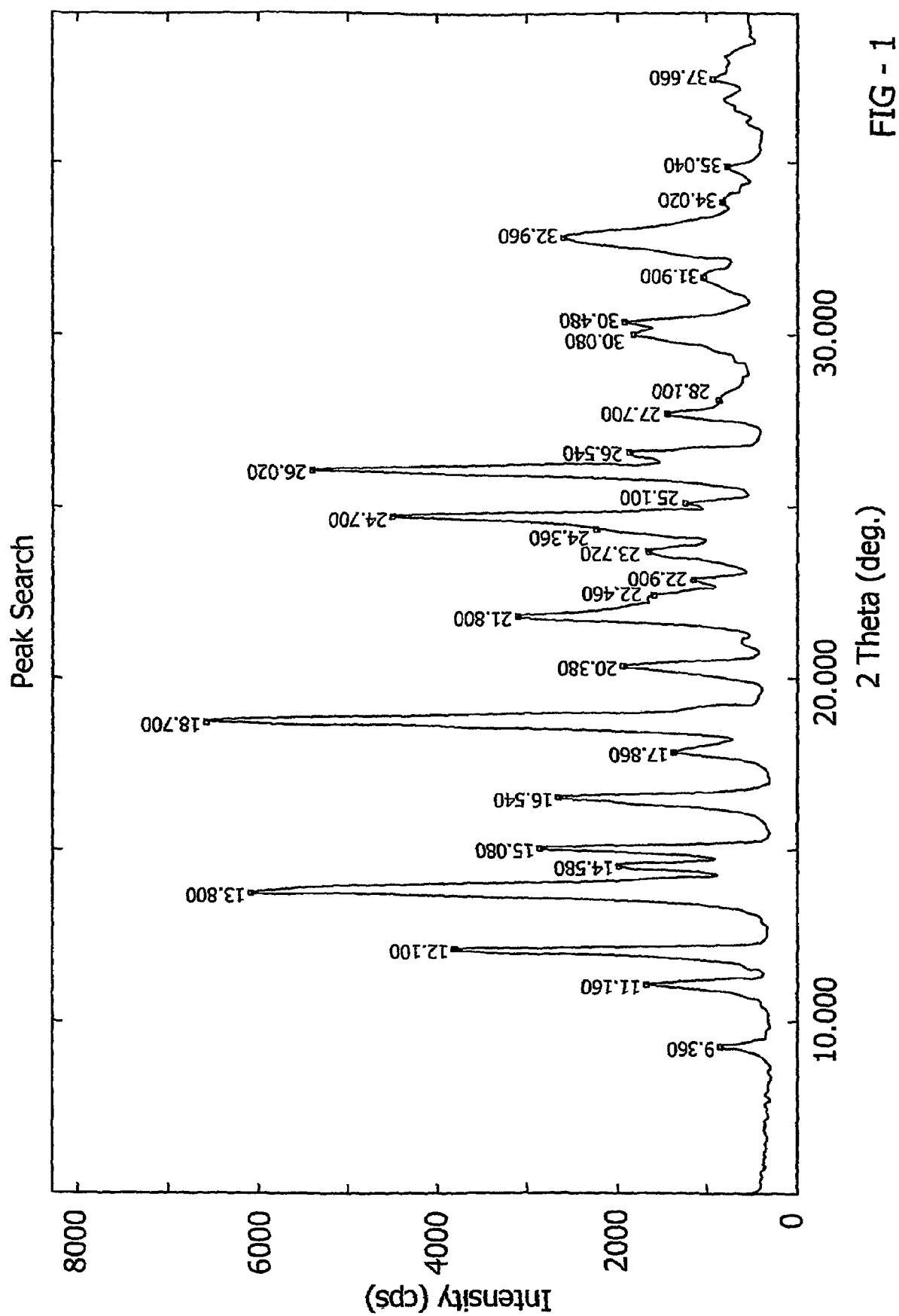
FIG. 1 represents a characteristic Powder X-ray diffraction (XRPD) spectrum of the crystalline A-1 form of (±)-1-cyclopropyl-6-fluoro-8-methoxy-7-(4-amino-3,3-dimethylpiperidin-1-yl)-1,4-dihydro-4-oxo-quinoline-3-carboxylic acid hydrochloride prepared by the methods described in our pending US application No. US 20030216568.

Unless defined otherwise, all technical and scientific terms used herein have the same meaning as commonly understood by one of ordinary skill in the art.

Polymorphs (±) A-3, (±) B-1, (±) B-2, (+) A-3, (+) B-1, (+) B-2, (−) A-3, (−) A-4, (−) B-1 and (−) B-2 may be characterized or differentiated by their Powder X-ray diffraction (XRPD) spectrum. The polymorphs may also be characterized by their differential scanning calorimetric (DSC) thermogram and Infra-red (IR) spectrum. The polymorphs may be characterized by one, two or three of these.

The present invention relates to (±)-1-cyclopropyl-6-fluoro-8-methoxy-7-(4-amino-3,3-dimethylpiperidin-1-yl)-1,4-dihydro-4-oxo-quinoline-3-carboxylic acid hydrochloride polymorph A-3 [(±) A-3] characterised by at least one of the following: an Powder X-ray diffraction pattern comprising peaks at (2θ): 5.32±0.2°, 5.68±0.2°, 9.42±0.2°, 10.06±0.2°, 10.40±0.2°, 11.40±0.2°, 11.78±0.2°, 12.98±0.2°, 13.74±0.2°, 14.38±0.2°, 14.66±0.2°, 16.02±0.2°, 22.52±0.2°, 23.74±0.2°, 24.48±0.2°, 25.22±0.2°, 27.36±0.2°, 28.74±0.2°, 31.28±0.2°, 31.72±0.2°;

DSC: endotherm at 252.50° C. (onset at 243.43° C.); and
Infra-red spectrum selected peaks (cm$^{-1}$): 3442, 2951, 2609, 1729, 1617, 1515, 1452, 1320, 1179, 952, 883.

The present invention also relates to R-(+)-1-cyclopropyl-6-fluoro-8-methoxy-7-(4-amino-3,3-dimethylpiperidin-1-yl)-1,4-dihydro-4-oxo-quinoline-3-carboxylic acid hydrochloride polymorph A-3 [(+) A-3] characterised by at least one of the following: an Powder X-ray diffraction pattern comprising peaks at (2θ): 5.34±0.2°, 5.70±0.2°, 9.46±0.2°, 10.08±0.2°, 10.44±0.2°, 11.42±0.2°, 11.82±0.2°, 12.86±0.2°, 13.62±0.2°, 14.26±0.2°, 14.72±0.2°, 16.08±0.2°, 22.16±0.2°, 23.68±0.2°, 24.18±0.2°, 24.86±0.2°, 25.98±0.2°, 27.04±0.2°, 28.84±0.2°, 31.56±0.2°, 31.84±0.2°;

DSC: endotherm at 251.16° C. (onset at 241.05° C.); and
Infra-red spectrum (cm$^{-1}$): 3430, 2805, 1029, 1728, 1617, 1515, 1452, 1180, 1051, 951.

The present invention also relates to S-(−)-1-cyclopropyl-6-fluoro-8-methoxy-7-(4-amino-3,3-dimethylpiperidin-1-yl)-1,4-dihydro-4oxo-quinoline-3-carboxylic acid hydrochloride polymorph A-4 [(−) A-4] characterised by at least one of the following: an Powder X-ray diffraction pattern comprising peaks at (2θ): 5.34±0.2°, 5.68±0.2°, 9.48±0.2°, 10.08±0.2°, 10.44±0.2°, 11.42±0.2°, 11.84±0.2°, 12.86±0.2°, 13.62±0.2°, 14.24±0.2°, 14.74±0.2°, 16.08±0.2°, 22.16±0.2°, 24.14±0.2°, 24.82±0.2°, 25.94±0.2°, 27.02±0.2°, 28.84±0.2°, 31.82±0.2°;

DSC: endotherm at 254.33° C. (onset at 248.00° C.); and
Infra-red spectrum (cm$^{-1}$): 2895, 1729, 1618, 1516, 1452, 1379, 1321, 1179, 1108, 1050, 951, 882, 808, 734.

The present invention further relates to a process for making (±)-1-cyclopropyl-6-fluoro-8-methoxy-7-(4-amino-3,3-dimethylpiperidin-1-yl)-1,4-dihydro-4-oxo-quinoline-3-carboxylic acid hydrochloride polymorph A-3, R-(+)-1-cyclopropyl-6-fluoro-8-methoxy-7-(4-amino-3,3-dimethylpiperidin-1-yl)-1,4-dihydro-4-oxo-quinoline-3-carboxylic acid hydrochloride polymorph A-3, and S-(−)-1-cyclopropyl-6-fluoro-8-methoxy-7-(4-amino-3,3-dimethylpiperidin-1-yl)-1,4-dihydro-4-oxo-quinoline-3-carboxylic acid hydrochloride polymorph A-4 comprising the steps of drying polymorphic forms A-1 at an elevated temperature optionally under vacuum, for a time sufficient to effect transformation to polymorphic form A-3 of racemic (±) and dextrorotatory R-(+) and polymorphic form A-4 of levorotatory S-(−) enantiomers of 1-cyclopropyl-6-fluoro-8-methoxy-7-(4-amino-3,3-dimethylpiperidin-1-yl)-1,4-dihydro-4-oxo-quinoline-3-carboxylic acid hydrochloride. In an example of the method, the drying of polymorphic form A-1 is carried out for about 12 hours.

The present invention relates to S-(−)-1-cyclopropyl-6-fluoro-8-methoxy-7-(4-amino-3,3-dimethylpiperidin-1-yl)-1,4-dihydro-4-oxo-quinoline-3-carboxylic acid hydrochloride polymorph A-3 [(−) A-3] characterised by at least one of the following: an Powder X-ray diffraction pattern comprising peaks at (2θ): 7.04±0.2°, 7.70±0.2°, 8.06±0.2°, 12.34±0.2°, 12.78±0.2°, 13.64±0.2°, 15.40±0.2°, 16.14±0.2°, 18.62±0.2°, 19.40±0.2°, 20.64±0.2°, 21.84±0.2°, 23.22±0.2°, 26.80±0.2°, 27.88±0.2°, 29.86±0.2°, 32.30±0.2°, 33.36±0.2°, 37.02±0.2°, 39.24±0.2°;

DSC: endotherm at 131.66° C. (onset at 95.32° C.), exotherm at 202.16° C. (onset at 198.36° C.), endotherm at 257.33° C. (onset at 252.359° C.)); and Infra-red spectrum selected peaks (cm$^{-1}$): 3396, 1715, 1621, 1530, 1451, 1274.

The present invention further relates to a process for making S-(−)-1-cyclopropyl-6-fluoro-8-methoxy-7-(4-amino-3,3-dimethylpiperidin-1-yl)-1,4-dihydro-4-oxo-quinoline-3-carboxylic acid hydrochloride polymorph A-3 comprising the steps of suspending or dissolving polymorphic form A-1 or A-2 of 1-cyclopropyl-6-fluoro-8-methoxy-7-(4-amino-3,3-dimethylpiperidin-1-yl-1,4-dihydro-4-oxo-quinoline-3-carboxylic acid hydrochloride in water, if necessary by heating, to form a suspension or a solution; adding an organic solvent such as $C_1$-$C_4$ alcohol selected from methanol, ethanol, n-propanol or isopropanol to the solution and isolating the polymorphic form A-3. In an alternate process polymorph A-1 can be dissolved in an aqueous solution of a hydrochloride salt of an inorganic acid, or a hydrochloride salt of an organic acid, or a sugar like dextrose, the solution allowed to cool and the crystals of the polymorphic form A-3 isolated.

The present invention furthermore relates to (±)-1-cyclopropyl-6-fluoro-8-methox-7-(4-amino-3,3-dimethylpipendin-1-yl)-1,4-dihydro-4-oxo-quinoline-3-carboxylic acid mesylate polymorph B-1 [(±) B-1] characterised by at least one of the following: an Powder X-ray diffraction pattern comprising peaks at (2θ): 5.80±0.2°, 8.08±0.2°, 9.08±0.2°, 12.92±0.2°, 14.70±0.2°, 16.48±0.2°, 17.40±0.2°, 18.36±0.2°, 18.74±0.2°, 19.60±0.2°, 20.44±0.2°, 20.94±0.2°, 21.50±0.2°, 22.80±0.2°, 23.28±0.2°, 23.84±0.2°, 24.36±0.2°, 25.50±0.2°, 26.00±0.2°, 26.78±0.2°, 27.24±0.2°, 29.22±0.2°, 30.66±0.2°, 37.58±0.2°.

DSC: endotherm at 302.33° C. (onset at 298.55° C.); and
Infra-red spectrum (cm$^{-1}$): 3443, 3079, 2960, 1735, 1615, 1516, 1446, 1383, 1323, 1236, 1139, 1045.

The present invention also relates to R-(+)-1-cyclopropyl-6-fluoro-8-methoxy-7-(4-amino-3,3-dimethylpiperidin-1-yl)-1,4-dihydro-4-oxo-quinoline-3-carboxylic acid mesylate polymorph B-1 [(+) B-1] characterised by at least one of the following: an Powder X-ray diffraction pattern comprising peaks at (2θ): 5.74±0.2°, 8.02±0.2°, 9.02±0.2°, 12.84±0.2°, 14.74±0.2°, 16.46±0.2°, 17.32±0.2°, 18.38±0.2°, 19.58±0.2°, 20.38±0.2°, 20.92±0.2°, 21.48±0.2°, 22.80±0.2°, 23.80±0.2°, 24.28±0.2°, 25.62±0.2°, 26.88±0.2°, 27.32±0.2°, 28.20±0.2°, 29.16±0.2°, 30.68±0.2°.

DSC: endotherm at 299.83° C. (onset at 295.27° C.); and

Infrared spectrum (cm$^{-1}$): 3442, 2958, 2625, 1735, 1616, 1516, 1446, 1323, 1236, 1140, 1045, 961, 550.

The present invention furthermore relates to S-(−)-1-cyclopropyl-6-fluoro-8-methoxy-7-(4-amino-3,3-dimethylpiperidin-1-yl)-1,4-dihydro-4-oxo-quinoline-3-carboxylic acid mesylate polymorph B-1 [(−) B-1] characterised by at least one of the following: an Powder X-ray diffraction pattern comprising peaks at (2θ): 8.02±0.2°, 12.84±0.2°, 14.70±0.2°, 16.44±0.2°, 17.30±0.2°, 19.56±0.2°, 20.90±0.2°, 21.46±0.2°, 23.76±0.2°, 25.56±0.2°, 27.30±0.2°, 30.66±0.2°, 37.46±0.2°;

DSC: endotherm at 301.00° C. (onset at 297.58° C.); and
Infra-red spectrum (cm$^{-1}$): 3441, 2956, 1735, 1617, 1517, 1447, 1321, 1231, 1141, 1043, 886, 821, 776.

The present invention furthermore relates to a process for making S-(−)-1-cyclopropyl-6-fluoro-8-methoxy-7-(4-amino-3,3-dimethylpiperidin-1-yl)-1,4-dihydro-4-oxo-quinoline-3-carboxylic acid mesylate polymorph B-1 comprising the steps of suspending or dissolving S-(−)-1-cyclopropyl-6-fluoro-8-methoxy-7-(4-amino-3,3-dimethylpiperidin-1-yl)-1,4-dihydro-4-oxo-quinoline-3-carboxylic acid in an organic solvent such as C1-C4 alcohol selected from methanol, ethanol, n-propanol or isopropanol to form a suspension/solution, heating the suspension/solution to a temperature between room temperature and efflux temperature of the solvent; adding methane sulfonic acid to the suspension/solution, heating the suspension/solution for a period of 1-24 hrs; and isolating the mesylate form B-1.

The present invention furthermore relates to (±)-1-cyclopropyl-6-fluoro-8-methoxy-7-(4-amino-3,3-dimethylpiperidin-1-yl)-1,4-dihydro-4-oxo-quinoline-3-carboxylic acid mesylate polymorph B-2 [(±) B-2] characterised by at least one of the following: an Powder X-ray diffraction pattern comprising peaks at (2θ): 9.40±0.2°, 9.94, 10.74±0.2°, 12.32±0.2°, 12.98±0.2°, 14.02±0.2°, 15.72±0.2°, 16.92±0.2°, 18.84±0.2°, 19.38±0.2°, 20.52±0.2°, 21.20±0.2°, 22.80, 22.96±0.2°, 24.64±0.2°, 25.54±0.2°, 28.38±0.2°, 29.92±0.2°, 30.72±0.2°, 35.92, 37.88±0.2°;

DSC: endotherm at 98.500° C. (onset at 74.41° C.), endotherm at 303.16° C. (onset at 298.849° C.); and
Infra-red spectrum (cm$^{-1}$): 3465, 2955, 1728, 1623, 1518, 1461, 1384, 1325, 1277, 1197, 1112, 1050.

The present invention also relates to R-(+)-1-cyclopropyl-6-fluoro-8-methoxy-7-(4-amino-3,3-dimethylpiperidin-1-yl)-1,4-dihydro-4-oxo-quinoline-3-carboxylic acid mesylate polymorph B-2 [(+) B-2] characterised by at least one of the following: an Powder X-ray diffraction pattern comprising peaks at (2θ): 8.04±0.2°, 9.36±0.20, 10.06±0.2°, 10.84±0.2°, 12.24±0.2°, 12.88±0.2°, 13.94±0.2°, 15.26±0.2°, 15.76±0.2°, 16.82±0.2°, 17.16±0.2°, 18.78±0.2°, 19.62±0.2°, 20.42±0.2°, 21.22±0.2°, 22.30±0.2°, 23.16±0.2°, 24.26±0.2°, 24.62±0.2°, 25.54±0.2°, 28.38±0.2°, 30.00±0.2°, 30.84±0.2°, 38.18±0.2°;

DSC: endotherm at 306.83° C. (onset at 303.39° C.); and
Infra-red spectrum (cm$^{-1}$): 3084, 2949, 1730, 1626, 1520, 1464, 1383, 1325, 1180, 1048, 949, 599.

The present invention furthermore relates to S-(−)-1-cyclopropyl-6-fluoro-8-methoxy-7-(4-amino-3,3-dimethylpiperidin-1-yl)-1,4-dihydro-4-oxo-quinoline-3-carboxylic acid mesylate polymorph B-2 [(−) B-2] characterised by at least one of the following: an Powder X-ray diffraction pattern comprising peaks at (2θ): 9.38±0.2°, 10.04±0.2°, 12.28±0.2°, 12.94±0.2°, 13.98±0.2°, 15.78±0.2°, 16.86±0.2°, 18.80±0.2°, 19.62±0.2°, 21.24±0.2°, 22.32±0.2°, 23.18±0.2°, 24.64±0.2°, 25.56±0.2°, 28.44±0.2°, 30.02±0.2°, 30.90±0.2°, 39.74±0.2°;

DSC: exotherm at 83.83° C. (onset at 58.11° C.), endotherm at 305.50° C. (onset at 301.48° C.); and
Infra-red spectrum (cm$^{-1}$): 3486, 1728, 1624, 1521, 1460, 1325, 1191, 1047, 879, 781.

The present invention furthermore relates to a process for making (±)-1-cyclopropyl-6-fluoro-8-methoxy-7-(4-amino-3,3-dimethylpiperidin-1-yl)-1,4-dihydro-4-oxo-quinoline-3-carboxylic acid mesylate polymorph B-2, a process for making R-(+)-1-cyclopropyl-6-fluoro-8-methoxy-7-(4-amino-3,3-dimethylpiperidin-1-yl)-1,4-dihydro-4-oxo-quinoline-3-carboxylic acid mesylate polymorph B-2 and a process for making S-(−)-1-cyclopropyl-6-fluoro-8-methoxy-7-(4-amino-3,3-dimethylpiperidin-1-yl)-1,4-dihydro-4-oxo-quinoline-3-carboxylic acid mesylate polymorph B-2 comprising the steps of dissolving corresponding racemic or dextrorotatory or levorotatory crystalline form B-1 of 1-cyclopropyl-6-fluoro-8-methoxy-7-(4-amino-3,3-dimethylpiperidin-1-yl)-1,4-dihydro-4-oxo-quinoline-3-carboxylic acid mesylate in water, by heating if necessary, to form a solution; cooling the solution, adding an aqueous-miscible organic solvent such as C1-C4 alcohol selected from methanol, ethanol, n-propanol, isopropanol, allowing to stand for 24 hrs to effect transformation to polymorphic form B-2; and isolating the mesylate polymorphic form B-2.

The present invention further relates to processes for preparing polymorphs of hydrochloride salt or mesylate salt of (+)-1-cyclopropyl-6-fluoro-8-methoxy-7-(4-amino-3,3-dimethylpiperidin-1-yl)-1,4-dihydro-4-oxo-quinoline-3-carboxylic acid and R-(+)-1-cyclopropyl-6-fluoro-8-methoxy-7-(4-amino-3,3-dimethylpiperidin-1-yl)-1,4-dihydro-4-oxo-quinoline-3-carboxytic acid A-3, B-1 and B-2 as illustrated in FIG. 37.

The present invention further relates to processes for preparing polymorphs of hydrochloride salt and mesylate salt of S-(−)-1-cyclopropyl-6-fluoro-8-methoxy-7-(4-amino-3,3-dimethylpiperidin-1-yl)-1,4-dihydro-4-oxo-quinoline-3-carboxylic acid A-3, A-4, B-1 and B-2 as illustrated in FIG. 38

Referring to FIG. 37, polymorph A-3 of racemic (±)-1-cyclopropyl-6-fluoro8-methoxy-7-(4-amino-3,3-dimethylpiperidin-1-yl)-1,4-dihydro-4-oxo-quinoline-3-carboxylic acid hydrochloride is prepared in one sequence from polymorph A-1. Polymorph A-1 is prepared according to the method of Example 103 of our pending US patent application publication No. US 20030216568, the disclosure of which is hereby incorporated herein by reference in its entirety. Polymorphic form A-1 of (±)-1-cyclopropyl-6-fluoro-8-methoxy-7-(4-amino-3,3-dimethylpiperidin-1-yl)-1,4-dihydro-4-oxo-quinoline-3-carboxylic acid hydrochloride, has an Powder X-ray diffraction spectrum as shown in FIG. 1.

Figure 2:
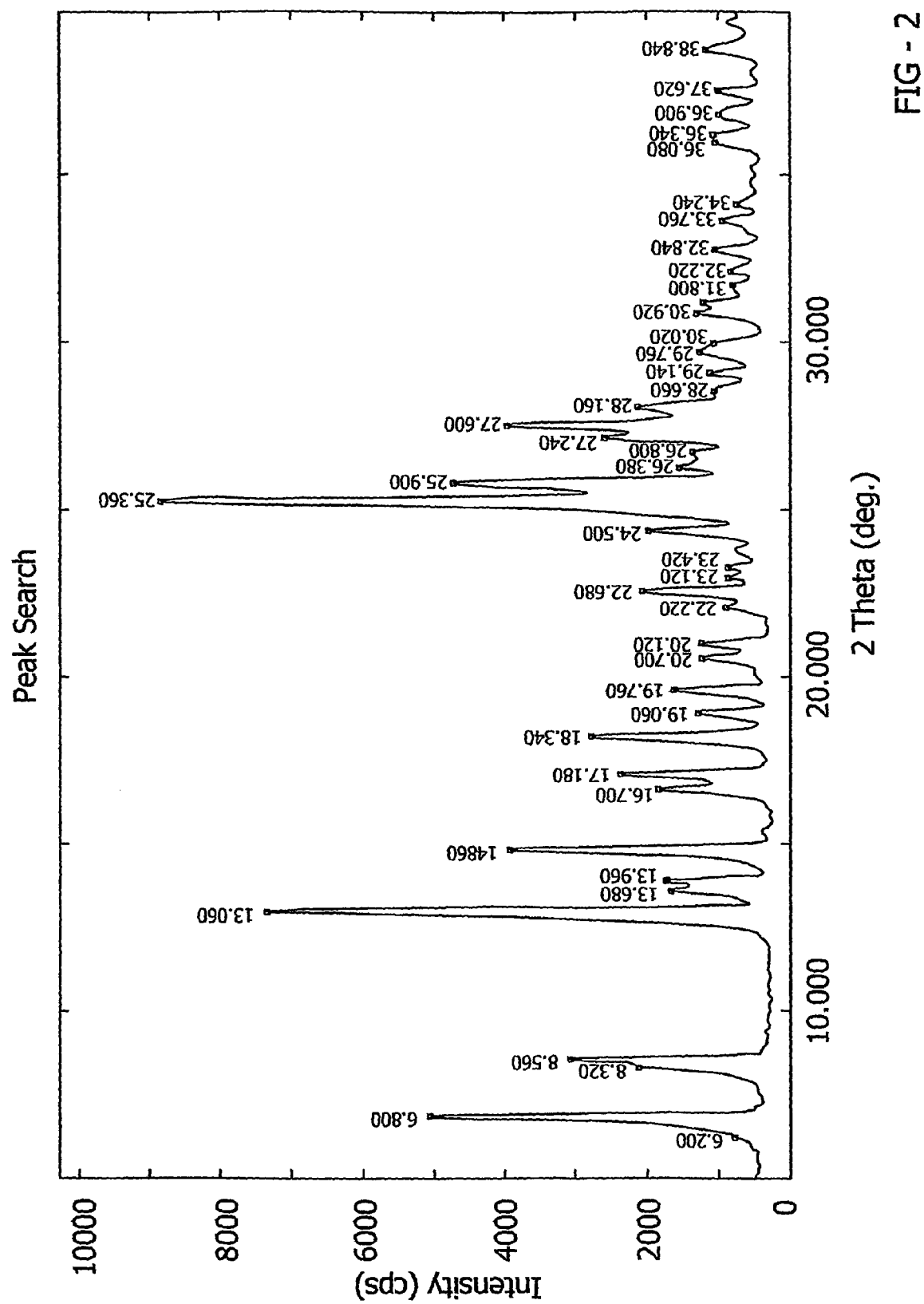
FIG. 2 represents a characteristic Powder X-ray diffraction (XRPD) spectrum of the crystalline A-2 form of (4)-1-cyclopropyl-6-fluoro-8-methoxy-7-(4-amino-3,3-dimethylpiperidin-1-yl)-1,4-dihydro-4-oxo-quinoline-3-carboxylic acid hydrochloride prepared by the methods described in our pending US application No. US 20030216568.

Polymorph A-3 may also be prepared from polymorph A-2 as per FIG. 37. Polymorph A-2is prepared according to the method of Example 104 of our pending US patent application publication No. US 20030216568, the disclosure of which is hereby incorporated herein by reference in its entirety. Polymorphic form A-2 of (±)-1-cyclopropyl-6-fluoro-8-methoxy-7-(4-amino-3,3dimethylpiperidin-1-yl)-1,4-dihydro-4-oxo-quinoline-3-carboxylic acid hydrochloride, has an Powder X-ray diffraction spectrum as shown in FIG. 2.

Figure 7:
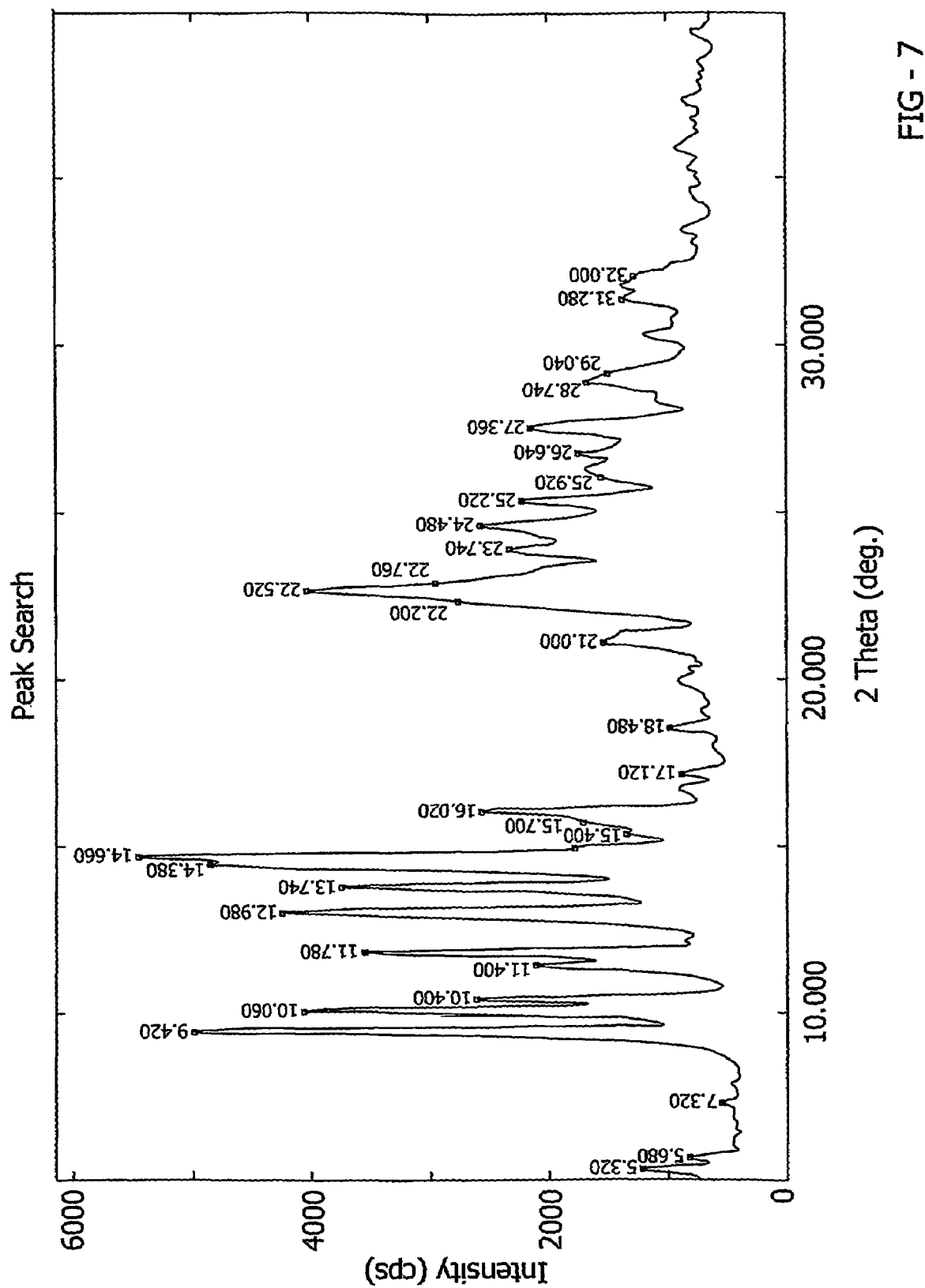
FIG. 7 represents a characteristic Powder X-ray diffraction (XRPD) spectrum of the crystalline A-3 form of (±)-1-cyclopropyl-6-fluoro-8-methoxy-7-(4-amino-3,3-dimethylpiperidin-1-yl)-1,4-dihydro-4-oxo-quinoline-3-carboxylic acid hydrochloride of the present invention.
Figure 17:
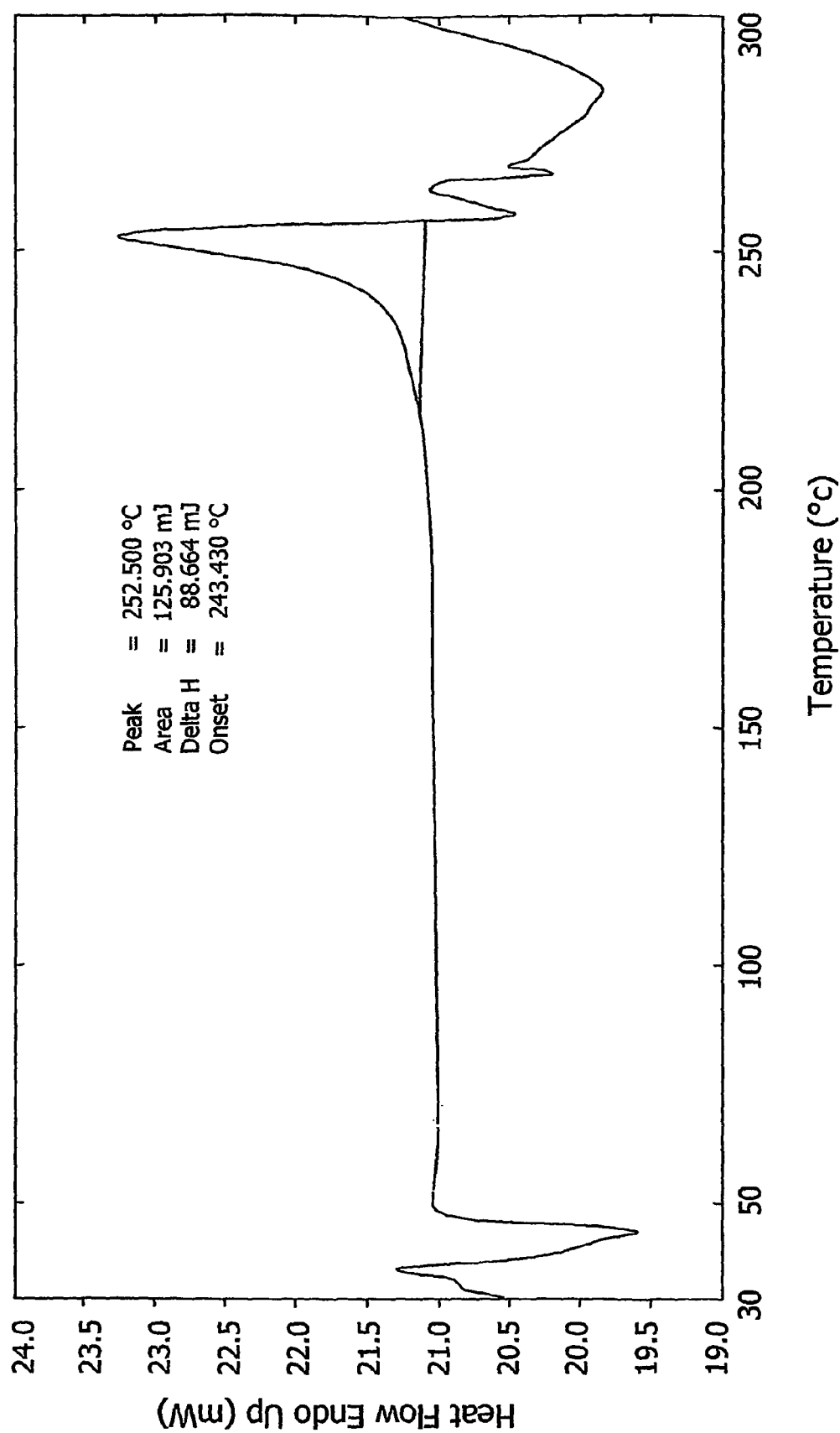
FIG. 17 represents a characteristic Differential Scanning Calorimetric (DSC) thermogram of the crystalline A-3 form of (±)-1-cyclopropyl-6-fluoro-8-methoxy-7-(4-amino-3,3-dimethylpiperidin-1-yl)-1,4-dihydro-4-oxo-quinoline-3-carboxylic acid hydrochloride of the invention.
Figure 27:
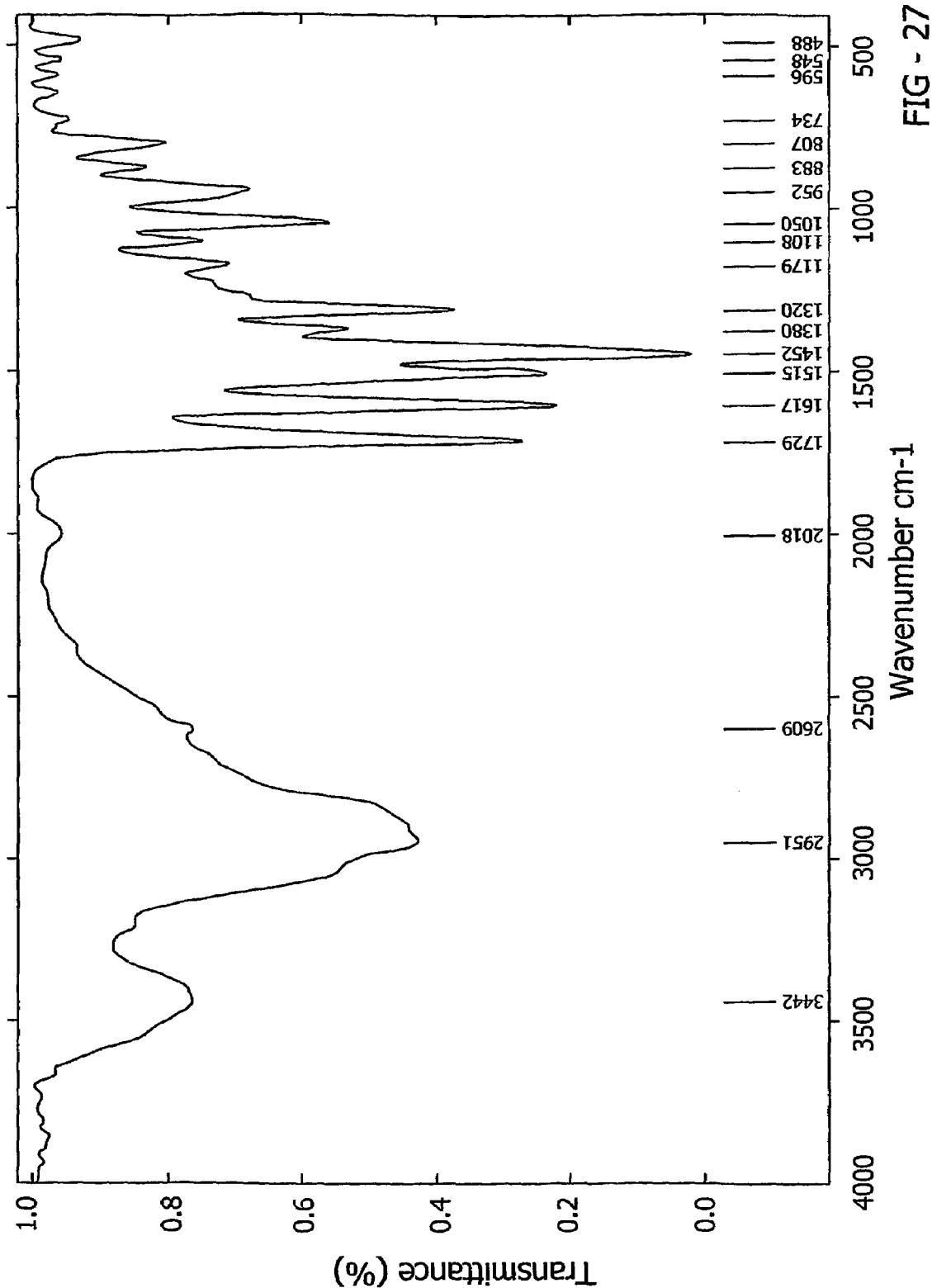
FIG. 27 represents a characteristic Infra-red (IR) spectrum of the crystalline A-3 form of (±)-1-cyclopropyl-4-fluoro-8-methoxy-7-(4-amino-3,3dimethylpiperidin-1-yl)-1,4-dihydro-4-oxo-quinoline-3-carboxylic acid hydrochloride of the invention.

Referring to FIG. 37, polymorph A-3 of (±)-1-cyclopropyl-6-fluoro-8-methoxy-7-(4-amino-3,3-dimethylpiperidin-1-yl)-1,4-dihydro-4-oxo-quinoline-3-carboxylic acid hydrochloride is prepared from polymorphs A-1 or A-2 by vacuum drying polymorphic forms A-1 or A-2 at an elevated temperature, preferably 130° C. up to 150° C. optionally under reduced pressure for a time, preferably up to 12 hours, and recovering the polymorphic form A-3 as a crystalline solid as shown in FIGS. 7, 17 and 27.

Powder X-ray diffraction (2θ): 5.32±0.2°, 5.68±0.2°, 9.49±0.2°, 10.06±0.2°, 10.40±0.2°, 11.40±0.2°, 11.78±0.2°, 12.98±0.2°, 13.74±0.2°, 14.38±0.2°, 14.66±0.2°, 16.02±0.2°, 22.52±0.2°, 23.74±0.2°, 24.48±0.2°, 25.22±0.2°, 27.36±0.2°, 28.74±0.2°, 31.28±0.2°;

DSC: endotherm at 252.50° C. (onset at 243.43° C.); Infrared spectrum selected peaks (cm$^{-1}$): 3442, 2951, 2609, 1729, 1617, 1515, 1452, 1320, 1179, 952, 883.

Figure 3:
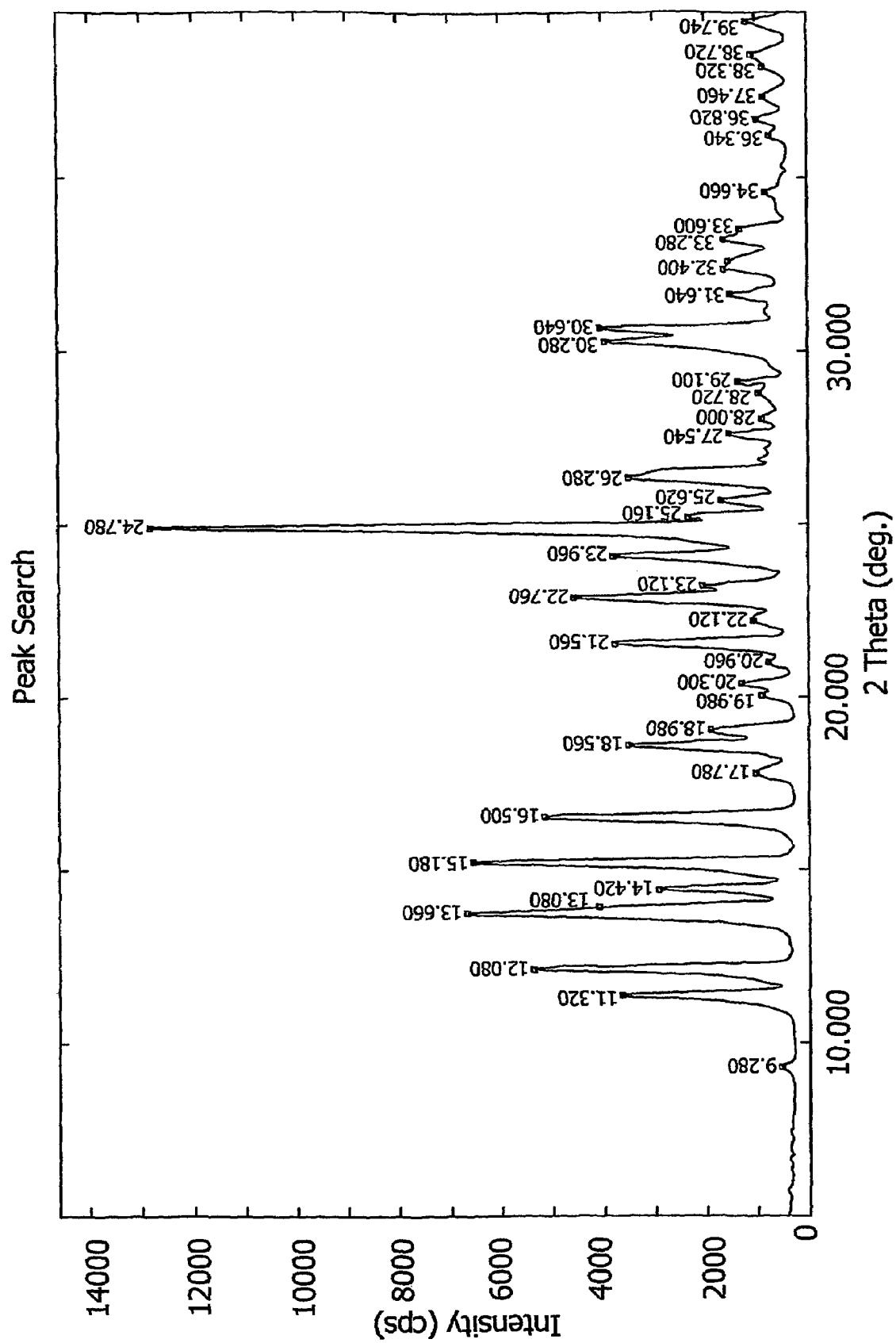
FIG. 3 represents a characteristic Powder X-ray diffraction (XRPD) spectrum of the crystalline A-1 form of R-(+)-1-cyclopropyl-6-fluoro-8-methoxy-7-(4-amino-3,3-dimethylpiperidin-1-yl)-1,4-dihydro-4-oxo-quinoline-3-carboxylic acid hydrochloride prepared by the methods described in our pending US application No. US 20030216568.

Polymorph A-3 of the dextrorotatory enantiomer R-(+)-1-cyclopropyl-6-fluoro-8-methoxy-7-(4-amino-3,3dimethylpiperidin-1-yl)-1,40-dihydro-4-oxo-quinoline-3-carboxylic acid hydrochloride may be prepared, as per FIG. 37, in one sequence from polymorph A-1. Polymorph A-1 is prepared according to the method of Example 107 of our pending US patent application No. US 20030216568. Polymorphic form A-1 of R-(+)-1-cyclopropyl-6-fluoro-8-methoxy-7-(4-amino-3,3-dimethylpiperidin-1-yl)-1,4-dihydro-4-oxo-quinoline-3-carboxylic acid hydrochloride, has an Powder X-ray diffraction spectrum as shown in FIG. 3.

Figure 4:
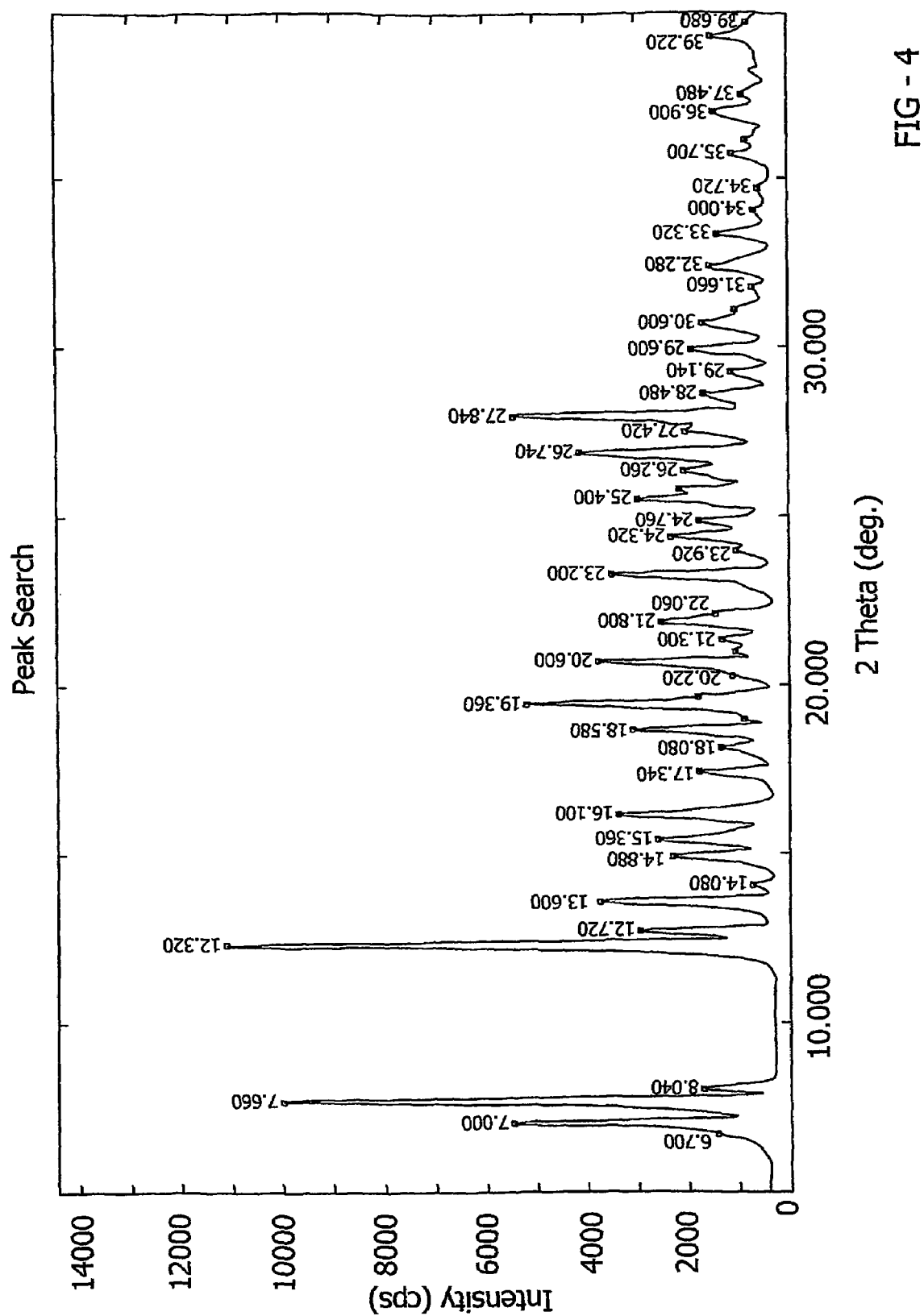
FIG. 4 represents a characteristic Powder X-ray diffraction (XRPD) spectrum of the crystalline A-2 form of R-(+)-1-cyclopropyl-6-fluoro-8-methoxy-7-(4-amino-3,3-dimethylpiperidin-1-yl)-1,4-dihydro-4-oxo-quinoline-3-carboxylic acid hydrochloride prepared by the methods described in our pending US application No. US 20030216568.

Polymorph A-3 of R-(+)-1-cyclopropyl-6-fluoro-8-methoxy-7-(4-amino-3,3-dimethylpiperidin-1-yl)-1,4-dihydro-4-oxo-quinoline-3-carboxylic acid hydrochloride can also be prepared from polymorph A-2 as per FIG. 37. Polymorph A-2 is prepared according to the method of Example 108 of our pending US patent application No. US 20030216568. Polymorphic form A-2 of R-(+)-1-cyclopropyl-6-fluoro-8-methoxy-7-(4-amino-3,3-dimethylpiperidin-1-yl)-1,4-dihydro-4-oxo-quinoline-3-carboxylic acid hydrochloride, has an Powder X-ray diffraction spectrum as shown in FIG. 4.

Figure 8:
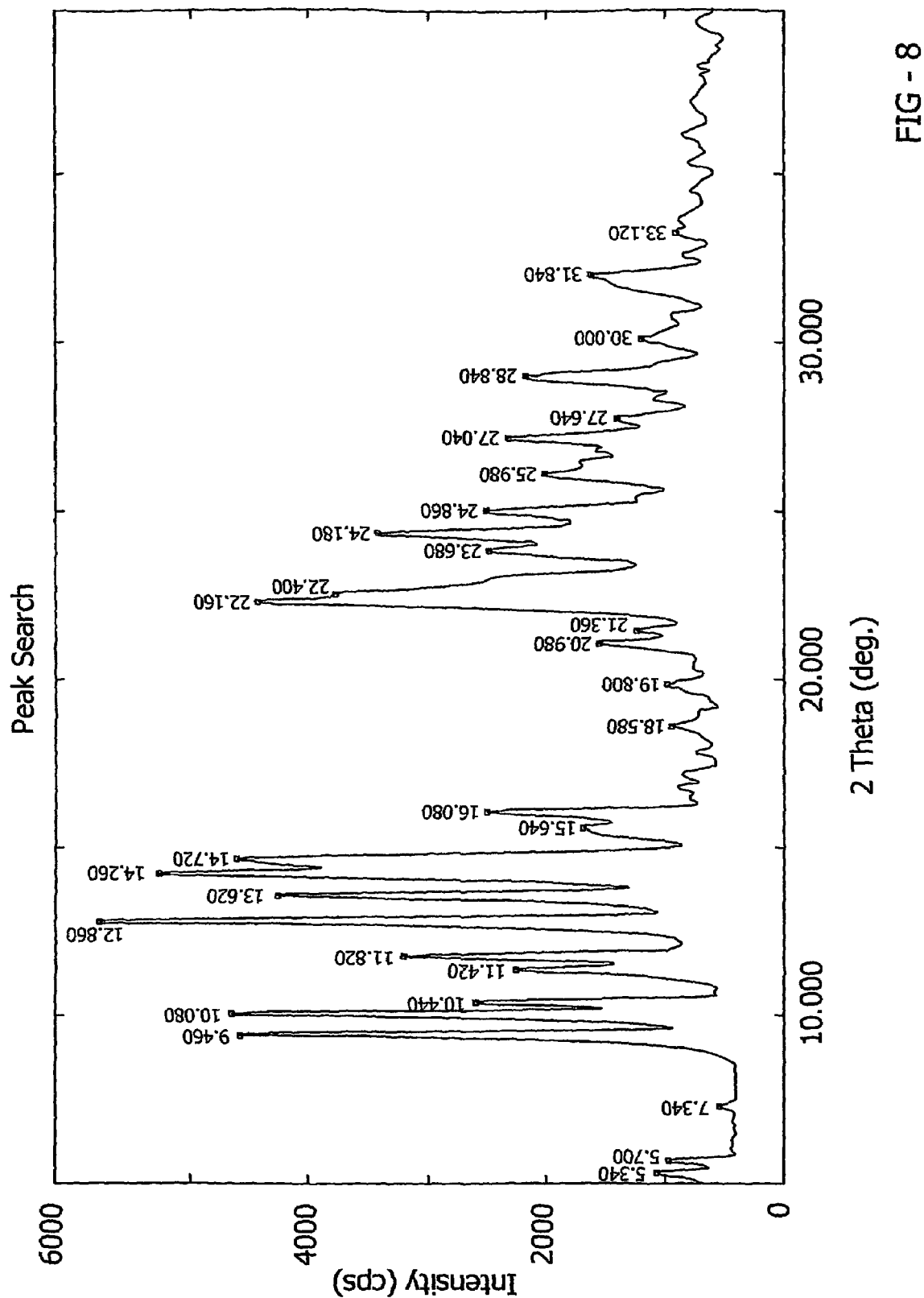
FIG. 8 represents a characteristic Powder X-ray diffraction (XRPD) spectrum of the crystalline A-3 form of R-(+)-1-cyclopropyl-6-fluoro-8-methoxy-7-(4-amino-3,3-dimethylpiperidin-1-yl)-1,4-dihydro-4-oxo-quinoline-3-carboxylic acid hydrochloride of the invention.
Figure 18:
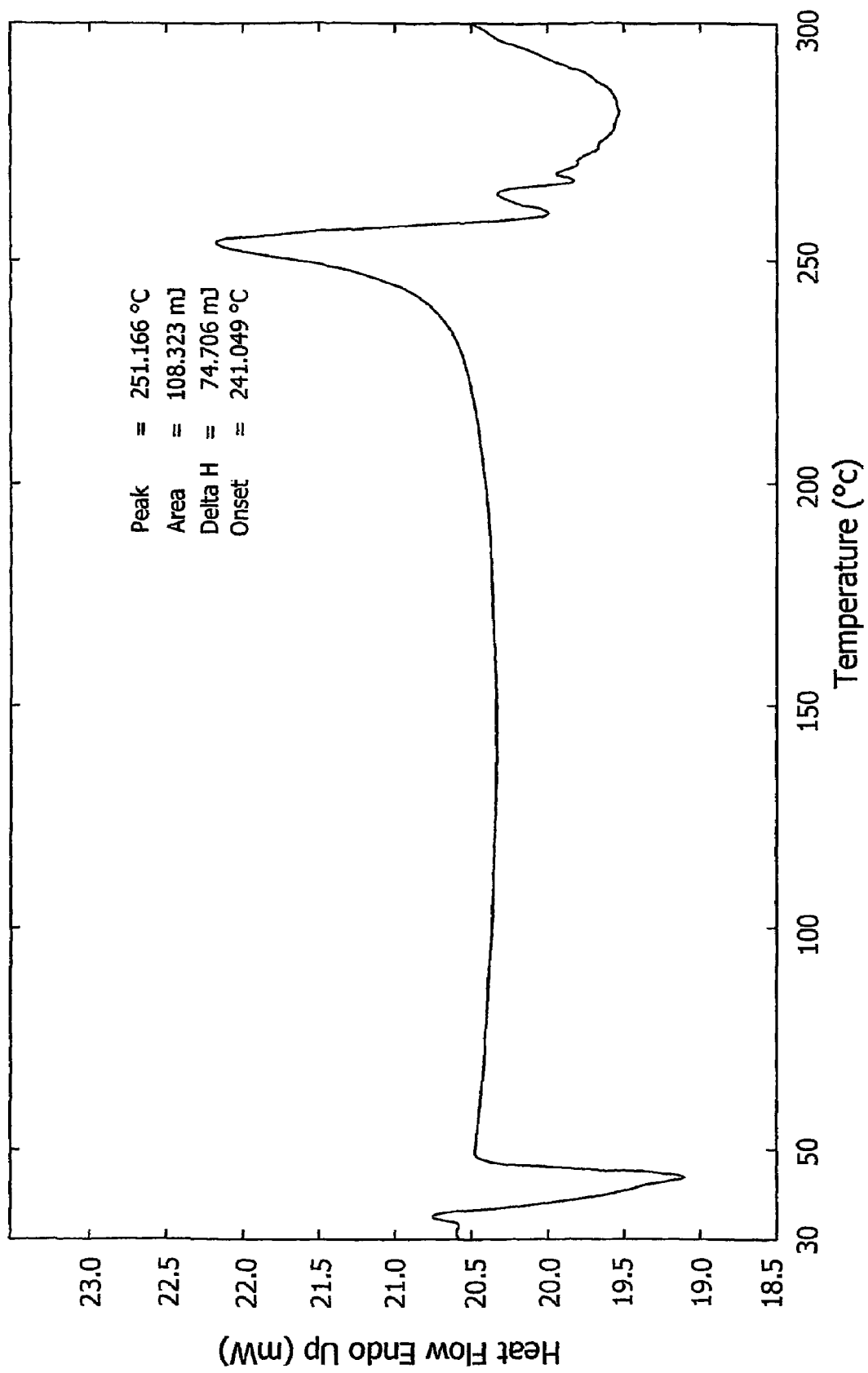
FIG. 18 represents the Differential Scanning Calorimetric (DSC) thermogram of the crystalline A-3 form of R-(+)-1-cyclopropyl-6-fluoro-8-methoxy-7-(4-amino-3,3-dimethylpiperidin-1-yl)-1,4-dihydro-4-oxo-quinoline-3-carboxylic acid hydrochloride of the invention.
Figure 28:
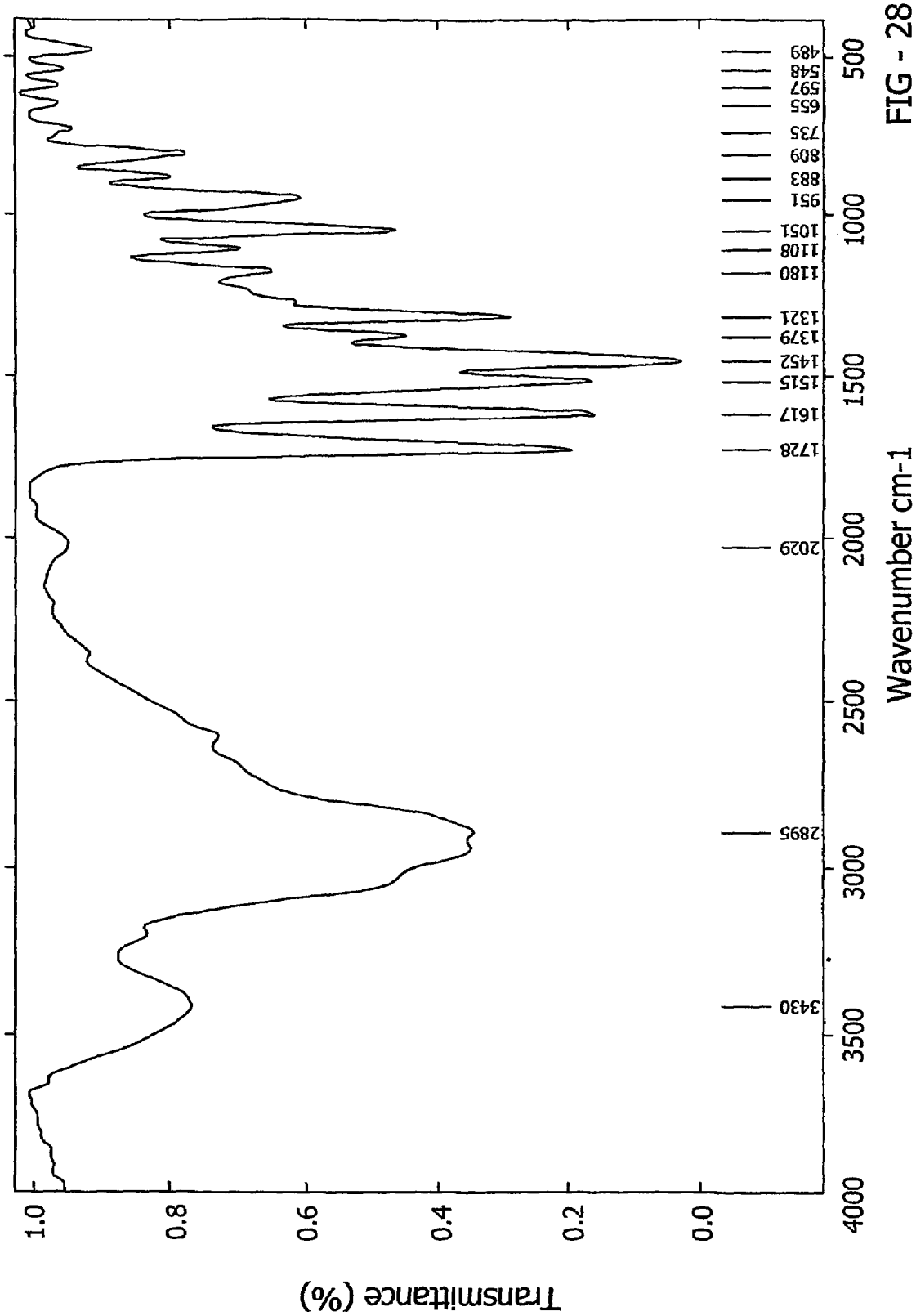
FIG. 28 represents the Infra-red (IR) spectrum of the crystalline A-3 form of R-(+)-1-cyclopropyl-6-fluoro-8-methoxy-7-(4-amino-3,3-dimethylpiperidin-1-yl)-1,4-dihydro-4-oxo-quinoline carboxylic acid hydrochloride of the invention.

Thus, polymorph A-3 of R-(+)-1-cyclopropyl-6-fluoro-8-methoxy-7-(4-amino-3,3-dimethylpiperidin-1-yl)-1,4-dihydro-4-oxo-quinoline-3-carboxylic acid hydrochloride can be prepared from polymorphs A-1 or A-2 by a process similar to that described above for the racemic forms (e.g. (±) A-3) by vacuum drying polymorphic forms A-1 or A-2 at an elevated temperature, preferably 130° C. up to 150° C. optionally under reduced pressure for a time, preferably up to 12 hours, and recovering the polymorphic form A-3 as a crystalline solid as shown in FIGS. 8, 18 and 28.

Powder X-ray diffraction (2θ): 5.34±0.2°, 5.70±0.2°, 9.46±0.2°, 10.08±0.2°, 10.44±0.2°, 11.42±0.2°, 11.82±0.2°, 12.86±0.2°, 13.62±0.2°, 14.26±0.2°, 14.72±0.2°, 16.08±0.2°, 22.16±0.2°, 23.68±0.2°, 24.18±0.2°, 24.86±0.2°, 25.98±0.2°, 27.04±0.2°, 28.84±0.2°, 31.56±0.2°, 31.84±0.2°;

DSC: endotherm at 251.16° C. (onset at 241.05° C.);

Infra-red spectrum (cm$^{-1}$): 3430, 2805, 1029, 1728, 1617, 1515, 1452, 1180, 1051, 951.

Polymorphic forms A-1 or A-3 of the (±)-mixture and R-(+)-isomer can be converted to their corresponding polymorphic forms A-2 according to a sequence in FIG. 37, by treatment with water and isopropanol. The water may be in the form of liquid or vapour.

Referring to FIG. 37, polymorph B-1 of (±)-1-cyclopropyl-6-fluoro-8-methoxy-7-(4-amino-3,3-dimethylpiperidin-1-yl)-1,4-dihydro-4-oxo-quinoline-3-carboxylic acid mesylate is prepared from (±)-1-cyclopropyl-6-fluoro-8-methoxy-7-(4-amino-3,3-dimethylpiperidin-1-yl)-1,4-dihydro-4-oxo-quinoline-3-carboxylic acid, described in Example 10 in our pending US application No. US 20030216568. Thus, (±)-1-cyclopropyl-6-fluoro-8-methoxy-7-(4-amino-3,3-dimethylpiperidin-1-yl)-1,4-dihydro-4-oxo-quinoline-3-carboxylic acid is suspended or dissolved in a suitable organic solvent such as $C_1$-$C_6$ alkanols, preferably isopropanol or $C_1$-$C_6$ alkyl esters of $C_1$-$C_6$ alkanoic acids, preferably ethyl acetate, or acetonitrile to form a suspension/solution, heating the suspension/solution to a temperature between about 25° C. and 80° C.; adding methane sulfonic acid to the suspension/solution, heating at a temperature of 70-80° C. for a period of time, preferably 1 hour, and recovering it as a crystalline material upon cooling the solution. The resultant crystals are dried to a constant weight to yield the polymorph B-1 of the invention. The polymorphic form of the crystals is provided in this invention as characterized by the data in the respective FIGS. 11, 21 and 31.

Powder X-ray diffraction (2θ): 5.80±0.2°, 8.08±0.2°, 9.08±0.2°, 12.92±0.2°, 14.70±0.2°, 16.48±0.2°, 17.40±0.2°, 18.36±0.2°, 18.74±0.2°, 19.60±0.2°, 20.44±0.2°, 20.94±0.2°, 21.50±0.2°, 22.80±0.2°, 23.28±0.2°, 23.84±0.2°, 24.36±0.2°, 25.50±0.2°, 26.00±0.2°, 26.78±0.2°, 27.24±0.2°, 29.22±0.2°, 30.66±0.2°, 37.58±0.2°.

DSC: endotherm at 302.33° C. (onset at 298.55° C.);

Infra-red spectrum (cm$^{-1}$): 3443, 3079, 2960, 1735, 1615, 1516, 1446, 1383, 1323, 1236, 1139, 1045.

Figure 12:
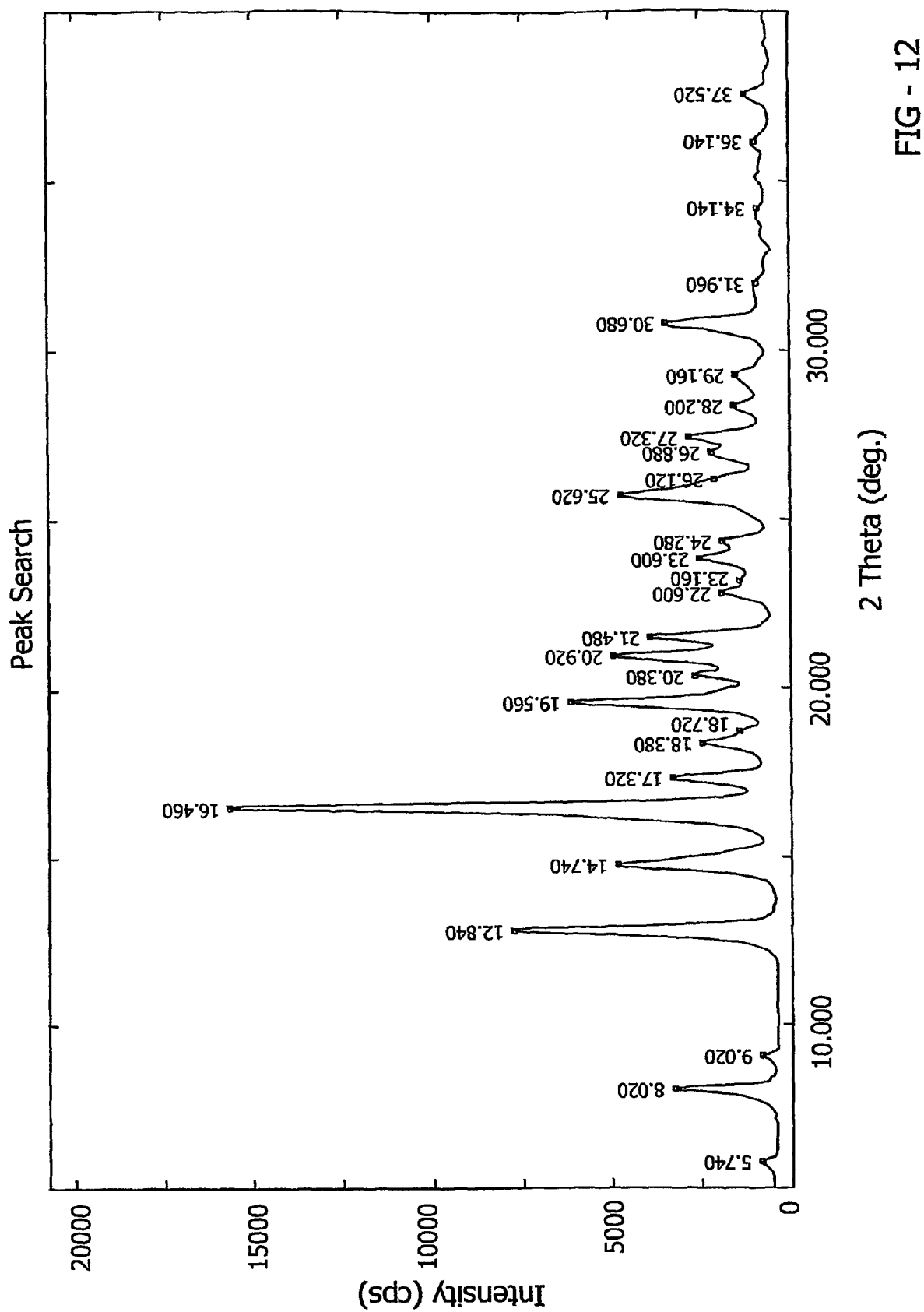
FIG. 12 represents the Powder X-ray diffraction (XRPD) spectrum of the crystalline B-1 form of R-(+)-1-cyclopropyl-6-fluoro-8-methoxy-7-(4-amino-3,3-dimethylpiperidin-1-yl)-1,4-dihydro-4-oxo-quinoline-3-carboxylic acid mesylate of the invention.
Figure 22:
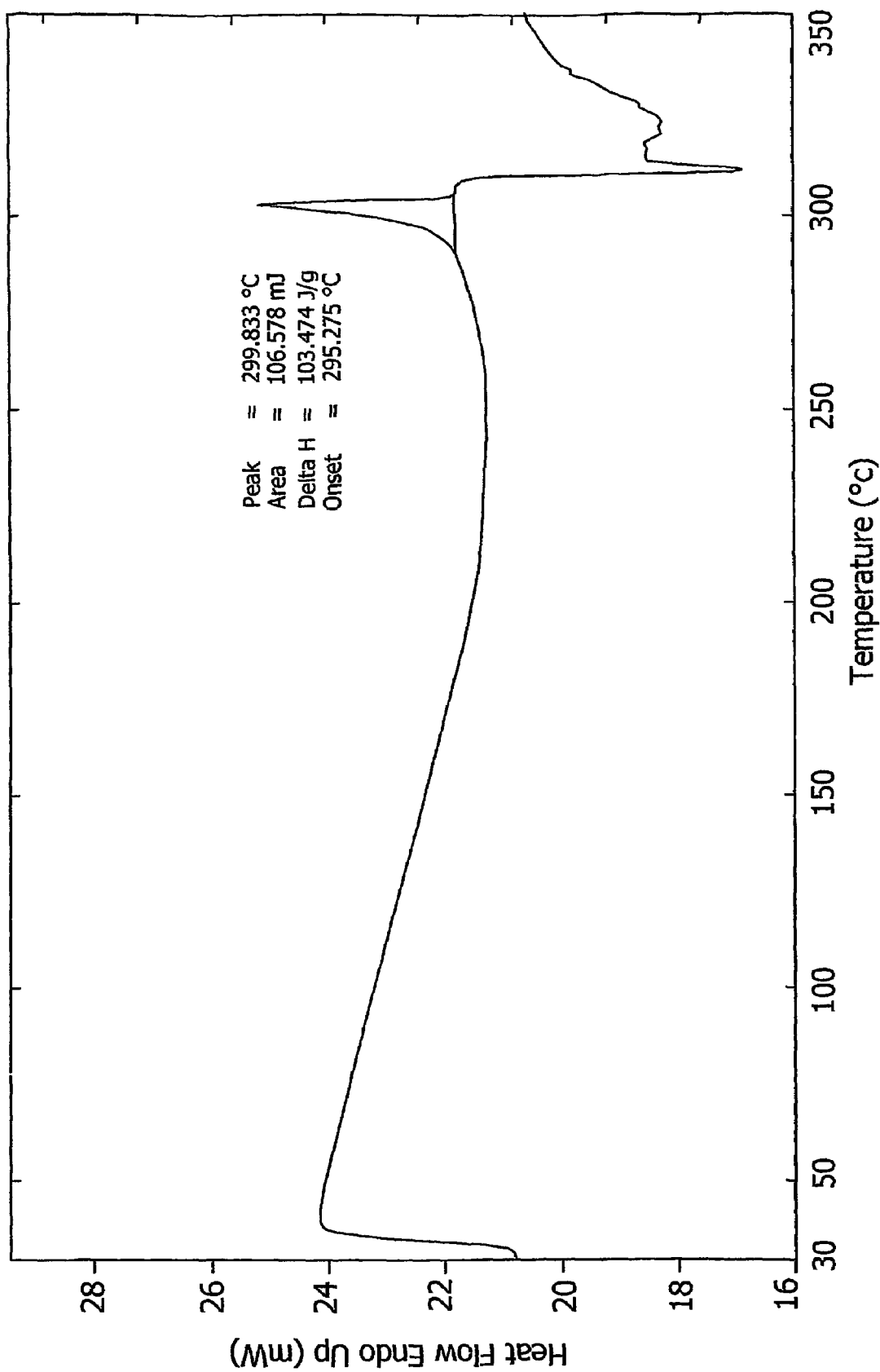
FIG. 22 represents the Differential Scanning Calorimetric (DSC) thermogram of the crystalline B-1 form of R-(+)-1-cyclopropyl-6-fluoro-8-methoxy-7-(4-amino-3,3-dimethylpiperidin-1-yl)-1,4-dihydro-4-oxo-quinoline-3-carboxylic acid mesylate of the invention.
Figure 32:
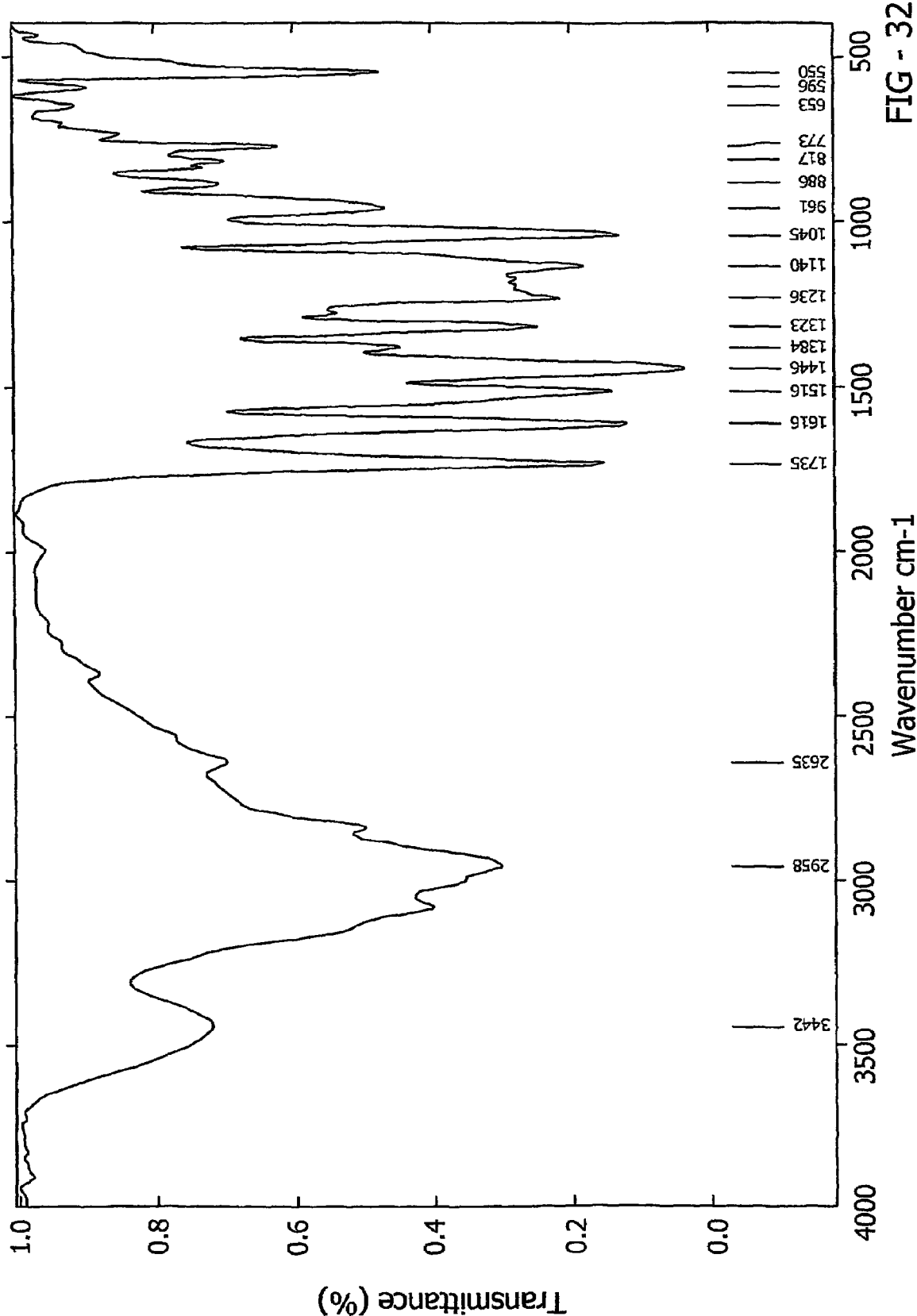
FIG. 32 represents the Infra-red (IR) spectrum of the crystalline B-1 form of R-(+)-1-cyclopropyl-6-fluoro-8-methoxy-7-(4-amino-3,3-dimethylpiperidin-1-yl)-1,4-dihydro-4-oxo-quinoline-3-carboxylic add mesylate of the invention.

Following a similar procedure as above, crystalline polymorph B-1 of R-(+)-1-cyclopropyl-6-fluoro-8-methoxy-7-(4-amino-3,3-dimethylpiperidin-1-yl)-1,4-dihydro-4-oxo-quinoline-3-carboxylic acid mesylate can be obtained from R-(+)-1-cyclopropyl-6-fluoro-8-methoxy-7-(4-amino-3,3-dimethylpiperidin-1-yl)-1,4-dihydro-4-oxo-quinoline-3-carboxylic acid. The procedure to prepare R-(+)-1-cyclopropyl-6-fluoro-8-methoxy-7-(4-amino-3,3-dimethylpiperidin-1-yl)-1,4-dihydro-4-oxo-quinoline-3-carboxylic acid is described in Example 16 in our pending US application No. US 20030216568. The polymorphic form of the crystals is provided in this invention as characterized by the data as shown in FIGS. 12, 22 and 32.

Powder X-ray diffraction (2θ): (2θ): 5.74±0.2°, 8.02±0.2°, 9.02±0.2°, 12.84±0.2°, 14.74±0.2°, 16.46±0.2°, 17.32±0.2°, 18.38±0.2°, 19.58±0.2°, 20.38±0.2°, 20.92±0.2°, 21.48±0.2°, 22.80±0.2°, 23.80±0.2°, 24.28±0.2°, 25.62±0.2°, 26.88±0.2°, 27.32±0.2°, 28.20±0.2°, 29.16±0.2°, 30.68±0.2°.

DSC: endotherm at 299.83° C. (onset at 295.27° C.);

Infrared spectrum (cm$^{-1}$): 3442, 2958, 2625, 1735, 1616, 1516, 1446, 1323, 1236, 1140, 1045, 961, 550.

Figure 14:
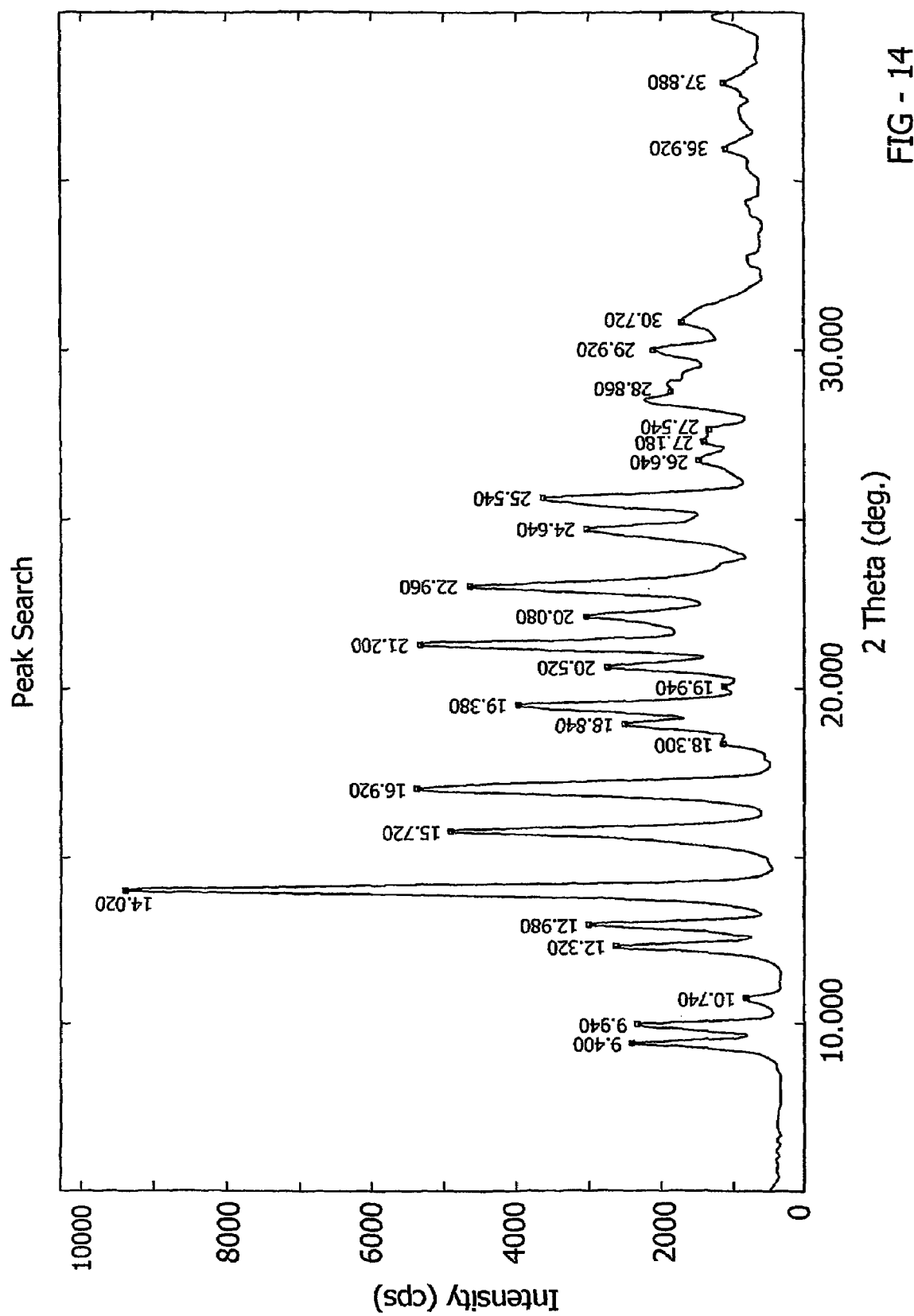
FIG. 14 represents the Powder X-ray diffraction (XRPD) spectrum of the crystalline B-2 form of (±)-1-cyclopropyl-6-fluoro-8-methoxy-7-(4-amino-3,3-dimethylpiperidin-1-yl)-1,4-dihydro-4-oxo-quinoline-3-carboxylic acid mesylate of the invention.
Figure 24:
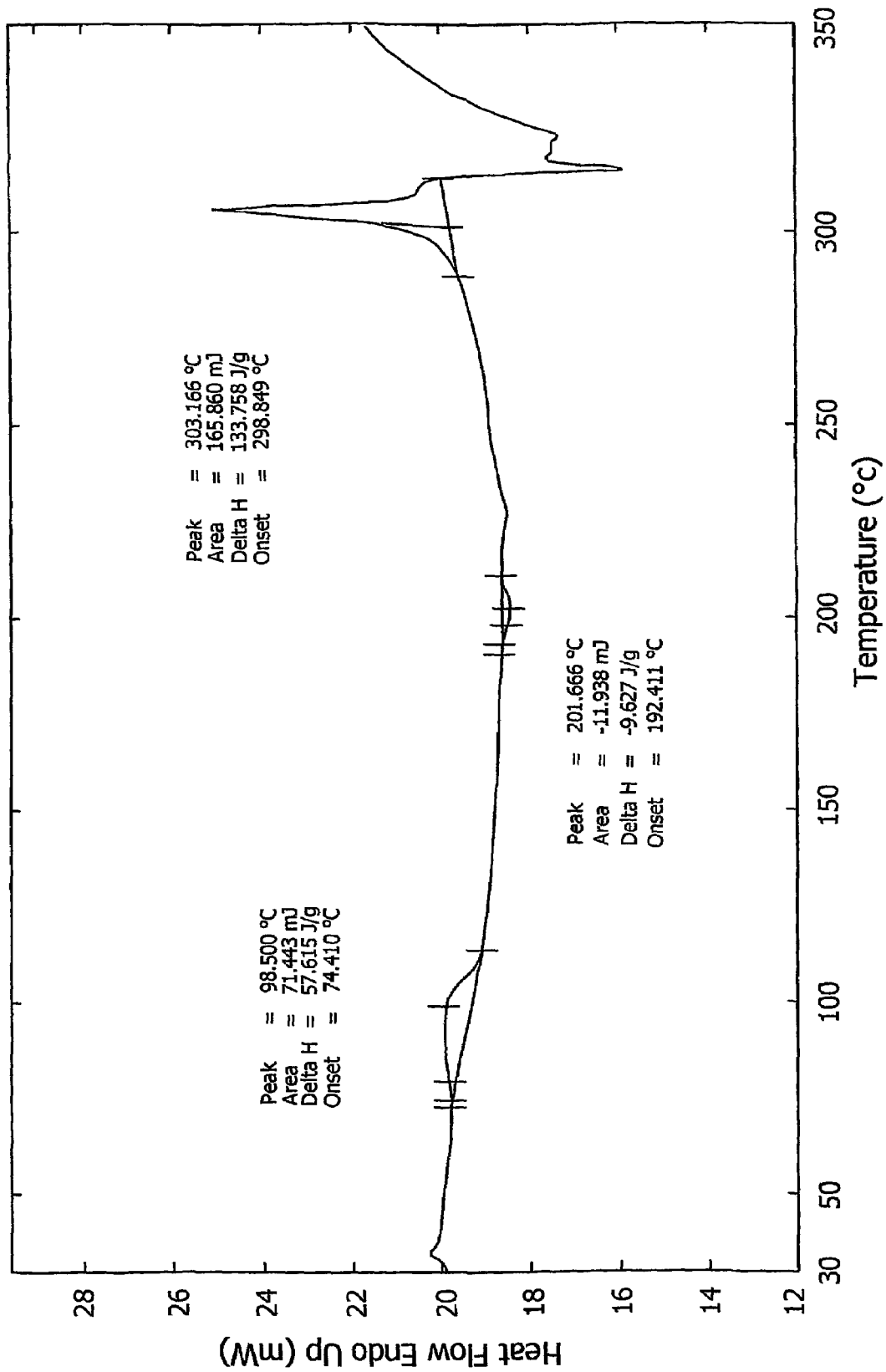
FIG. 24 represents the Differential Scanning Calorimetric (DSC) thermogram of the crystalline B-2 form of (±)-1-cyclopropyl-6-fluoro-8-methoxy-7-(4-amino-3,3-dimethylpiperidin-1-yl)-1,4-dihydro-4-oxo-quinoline-3-carboxylic acid mesylate of the invention.
Figure 36:
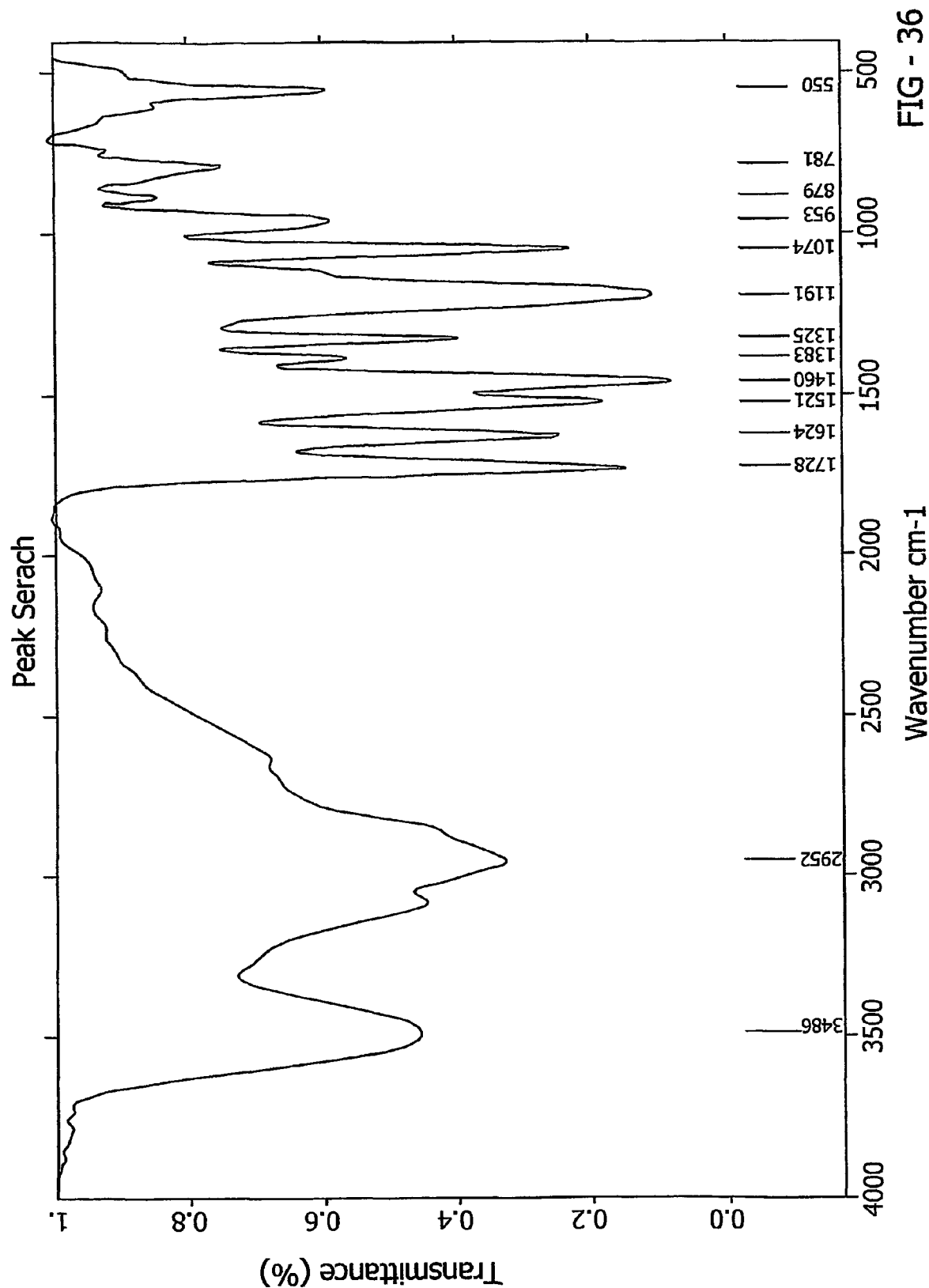
FIG. 36 represents the Infra-red (IR) spectrum of the crystalline B-2 form of S-(−)-1-cyclopropyl-6-fluoro-8-methoxy-7-(4-amino-3,3-dimethylpiperidin-1-yl)-1,4-dihydro-4-oxo-quinoline-3-carboxylic acid methane sulfonate of the invention.

Referring to FIG. 37, crystalline polymorph B-2 is prepared from polymorph B-1 by dissolving crystalline polymorphic form B-1 of (±)-1-cyclopropyl-6-fluoro-8-methoxy-7-(4-amino-3,3-dimethylpiperidin-1-yl)-1,4-dihydro-4-oxo-quinoline-3-carboxylic acid mesylate in water by heating at a temperature between 25-100° C., preferably 80-100° C. to form a solution; cooling the solution to 25-35° C. and adding an aqueous-miscible organic solvent. A suitable organic solvent includes $C_1$-$C_6$ alkanols, preferably isopropanol, or $C_3$-$C_6$ aliphatic ketones, preferably acetone, or acetonitrile. The reaction mixture is allowed to stand for a 24 hrs to effect transformation to polymorphic form B-2, and subsequent recovery of the polymorphic form B-2 as a crystalline material upon cooling to 25-35° C. The resultant crystals are dried to a constant weight to yield the polymorph B-2 of the invention as shown in FIGS. 14, 24 and 36.

Powder X-ray diffraction (2θ): 9.40±0.2°, 9.94, 10.74±0.2°, 12.32±0.2°, 12.98±0.2°, 14.02±0.2°, 15.72±0.2°, 16.92±0.2°, 18.84±0.2°, 19.38±0.2°, 20.52±0.2°, 21.20±0.2°, 22.80, 22.96±0.2°, 24.64±0.2°, 25.54±0.2°, 28.38±0.2°, 29.92±0.2°, 30.79±0.2°, 35.92, 37.88±0.2°;

DSC: endotherm at 98.50° C. (onset at 74.41° C.), endotherm at 303.16° C. (onset at 298.849° C.);

Infra-red spectrum (cm$^{-1}$): 3465, 2955, 1728, 1623, 1518, 1461, 1384, 1325, 1277, 1197, 1112, 1050.

Figure 15:
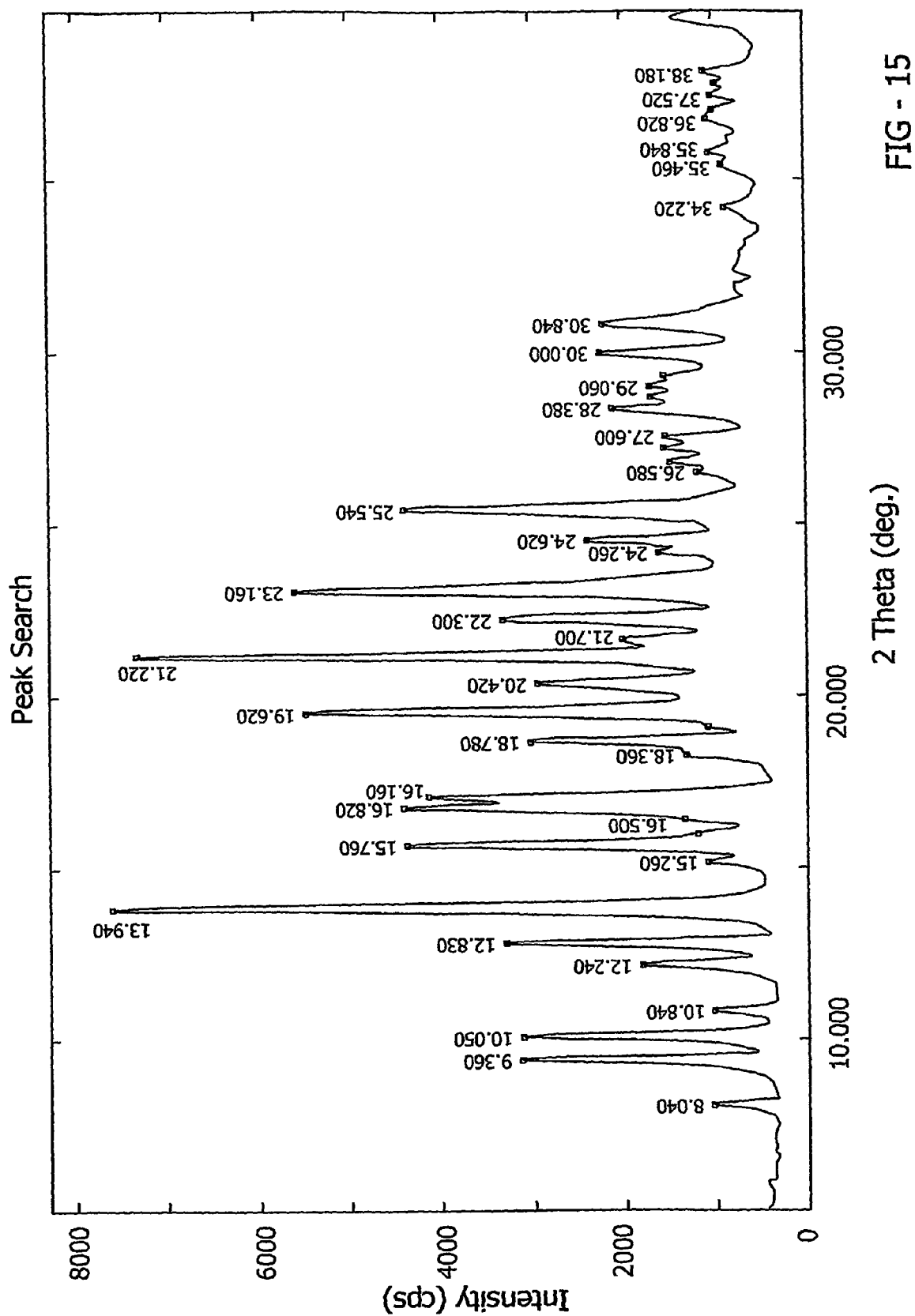
FIG. 15 represents the Powder X-ray diffraction (XRPD) spectrum of the crystalline B-2 form of R-(+)-1-cyclopropyl-6-fluoro-8-methoxy-7-(4-amino-3,3-dimethylpiperidin-1-yl)-1,4-dihydro-4-oxo-quinoline-3-carboxylic acid mesylate of the invention.
Figure 25:
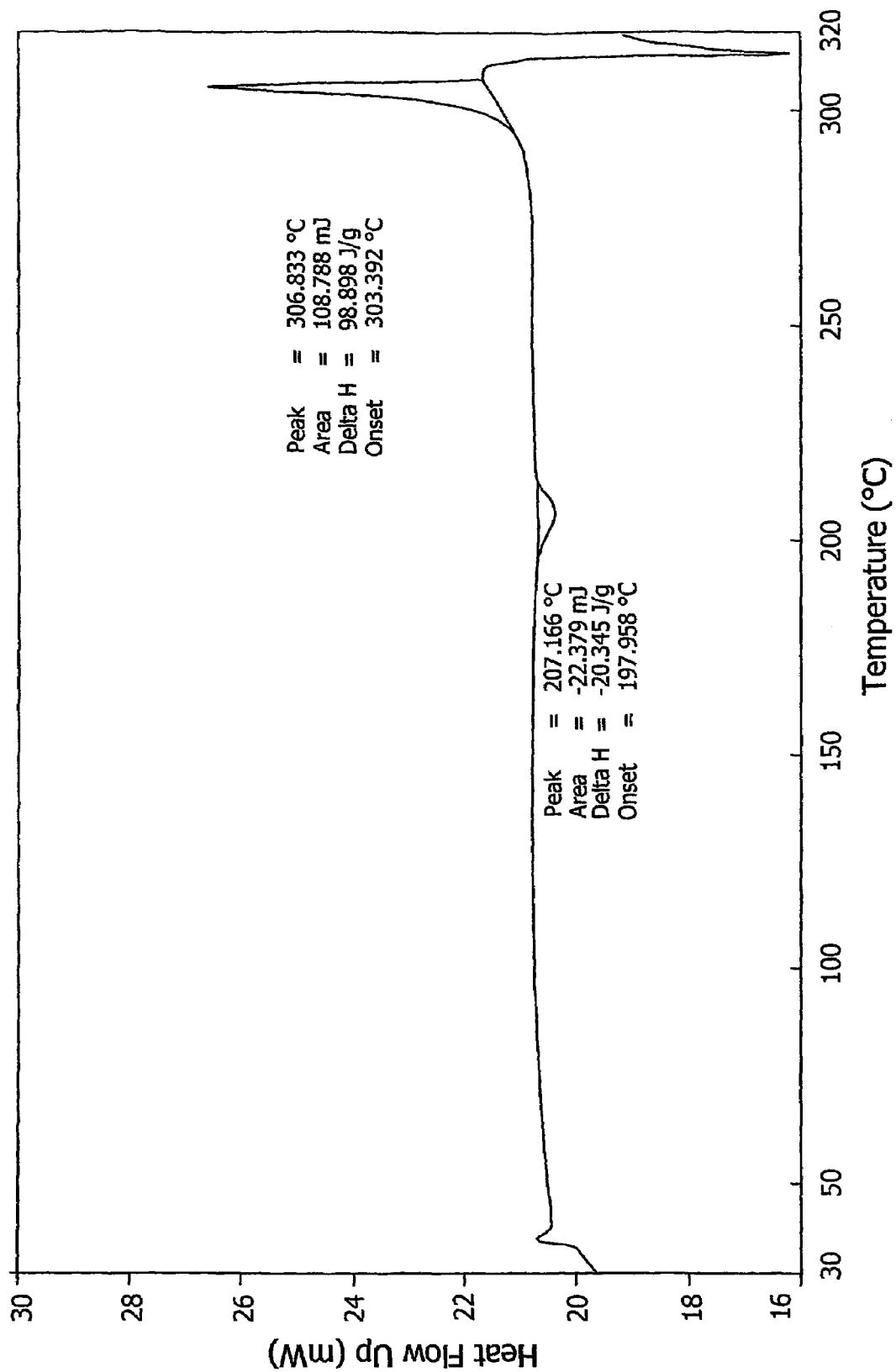
FIG. 25 represents the Differential Scanning Calorimetric (DSC) thermogram of the crystalline B-2 form of R-(+)-1-cyclopropyl-6-fluoro8-methoxy-7-(4-amino-3,3-dimethylpiperidin-1-yl)-1,4-dihydro-4-oxo-quinoline-3-carboxylic acid mesylate of the invention.
Figure 35:
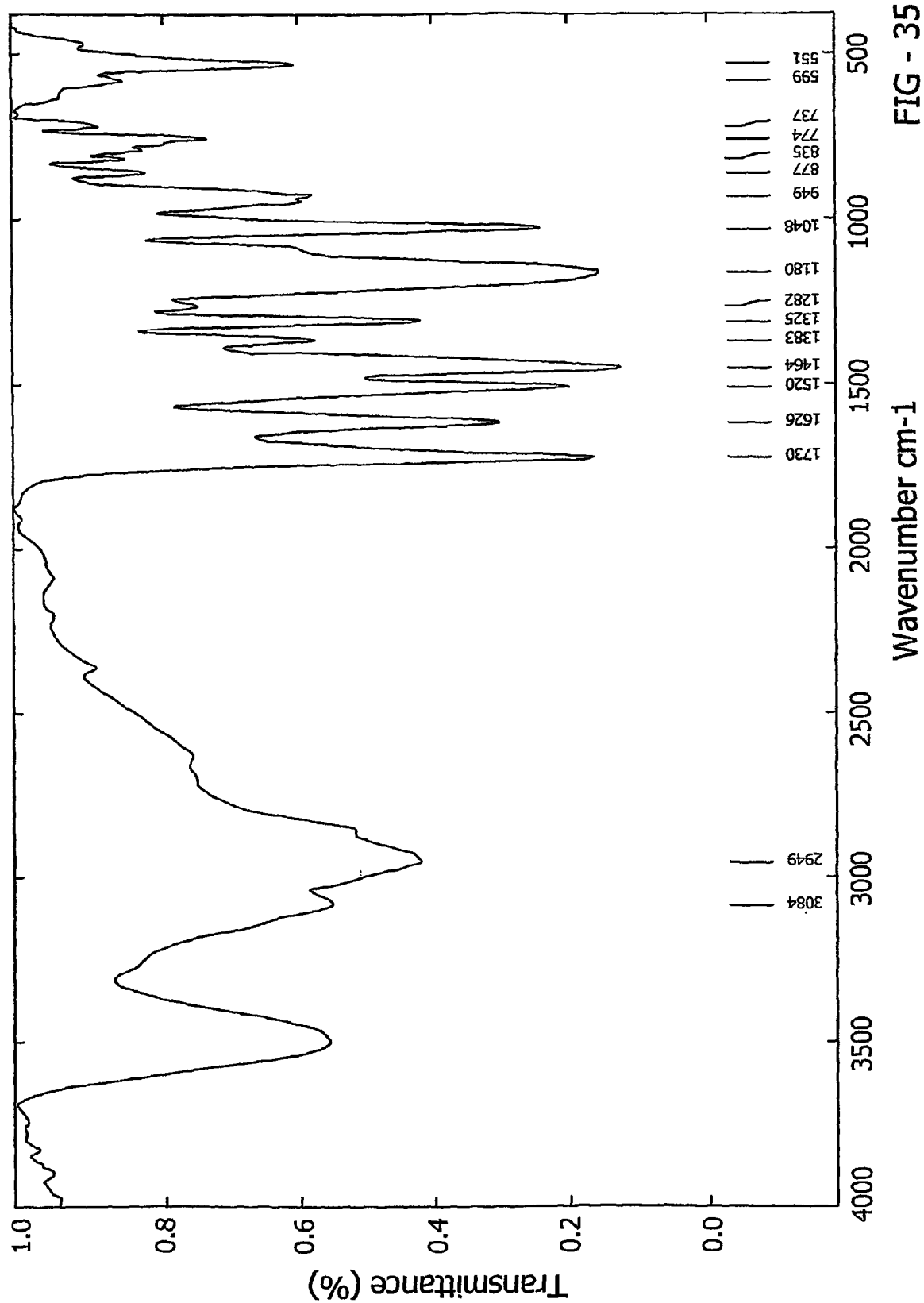
FIG. 35 represents the Infra-red (IR) spectrum of the crystalline B-2 form of R-(+)-1-cyclopropyl-6-fluoro-8-methoxy-7-(4-amino-3,3-dimethylpiperidin-1-yl)-1,4-dihydro-4-oxo-quinoline-3-carboxylic acid methane sulfonate of the invention.

Following the similar procedure as above, crystalline polymorph B-2 of R-(+)-1-cyclopropyl-6-fluoro-8-methoxy-7-(4-amino-3,3dimethylpiperidin-1-yl)-1,4-dihydro-4-oxo-quinoline-3-carboxylic acid mesylate can be obtained from crystalline polymorph B-1 of R-(+)-1-cyclopropyl-6-fluoro-8-methoxy-7-(4-amino-3,3-dimethylpiperidin-1-yl)-1,4-dihydro-4-oxo-quinoline-3-carboxylic acid as shown in FIGS. 15, 25 and 35.

Powder X-ray diffraction (2θ): 8.04±0.2°, 9.36±0.2°, 10.06±0.2°, 10.84±0.2°, 12.24±0.2°, 12.88±0.2°, 13.94±0.2°, 15.26±0.2°, 15.76±0.2°, 16.82±0.2°, 17.16±0.2°, 18.78±0.2°, 19.62±0.2°, 20.42±0.2°, 21.22±0.2°, 22.30±0.2°, 23.16±0.2°, 24.26±0.2°, 24.26±0.2°, 25.54±0.2°, 28.38±0.2°, 30.00±0.2°, 30.84±0.2°, 38.18±0.2°;

DSC: endotherm at 306.83° C. (onset at 303.39° C.);

Infra-red spectrum (cm$^{-1}$): 3084, 2949, 1730, 1626, 1520, 1464, 1383, 1325, 1180, 1048, 949, 599.

Referring to FIG. 38, polymorph A-3 of S-(−)-1-cyclopropyl-6-fluoro-8-methoxy-7-(4-amino-3,3-dimethylpipeddin-1-yl)-1,4-dihydro-4-oxo-quinoline-3-carboxylic acid hydrochloride is prepared in one sequence from polymorph A-1. Polymorph A-1 may be prepared according to the method of Example 105 of our pending US patent application No. 2003/0216568, the disclosure of which is hereby incorporated herein by reference in its entirety. Polymorphic form A-1 of S-(−)-1-cyclopropyl-6-fluoro-8-methoxy-7-(-amino-3,3-dimethylpiperidin-1-yl)-1,4-dihydro-4-oxo-quinoline-3-carboxylic acid hydrochloride, having Powder X-ray diffraction spectrum as shown in FIG. 1, is suspended or dissolved in water, if necessary by heating at 25-100° C., maintaining with stirring at that temperature for a period of time between 0.5 to 12 hours to form a suspension or a solution and adding a water-miscible organic solvent. Suitable solvents include $C_1$-$C_6$ alkanols, preferably isopropanol, or acetonitrile, or $C_3$-$C_6$ aliphatic ketones, preferably acetone. The resulting mixture is stirred for a sufficient period of time, preferably up to 12 hours to effect the transformation completely to polymorphic form A-3, and recovering the polymorphic form A-3 as a crystal upon cooling the solution. The resultant crystals are dried to a constant weight to yield the polymorph A-3 of the invention.

Figure 9:
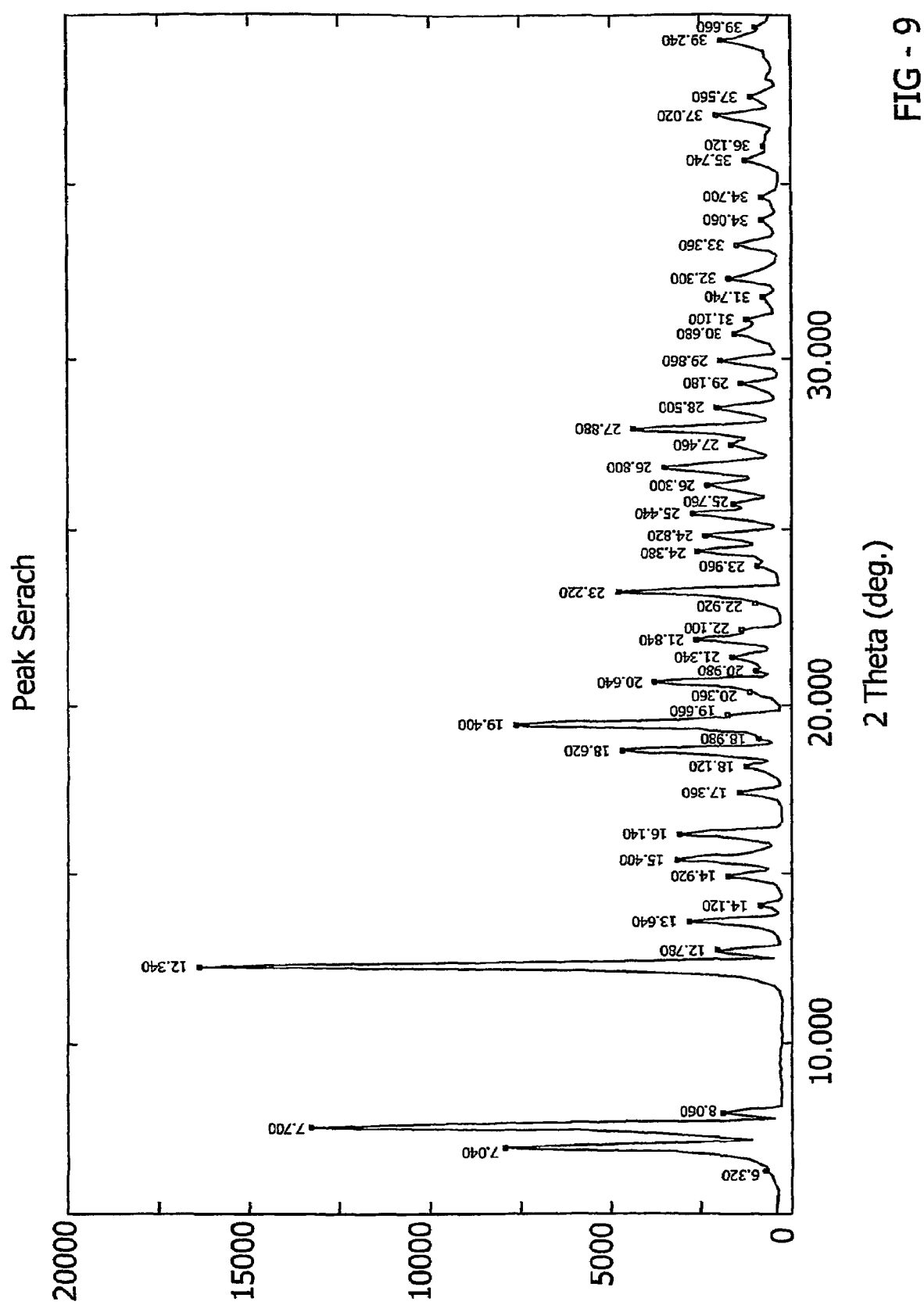
FIG. 9 represents a characteristic Powder X-ray diffraction (XRPD) spectrum of the crystalline A-3 form of S-(−)-1-cyclopropyl-6-fluoro-8-methoxy-7-(4-amino-3,3-dimethylpiperidin-1-yl)-1,4-dihydro-4-oxo-quinoline-3-carboxylic acid hydrochloride of the present invention.
Figure 19:
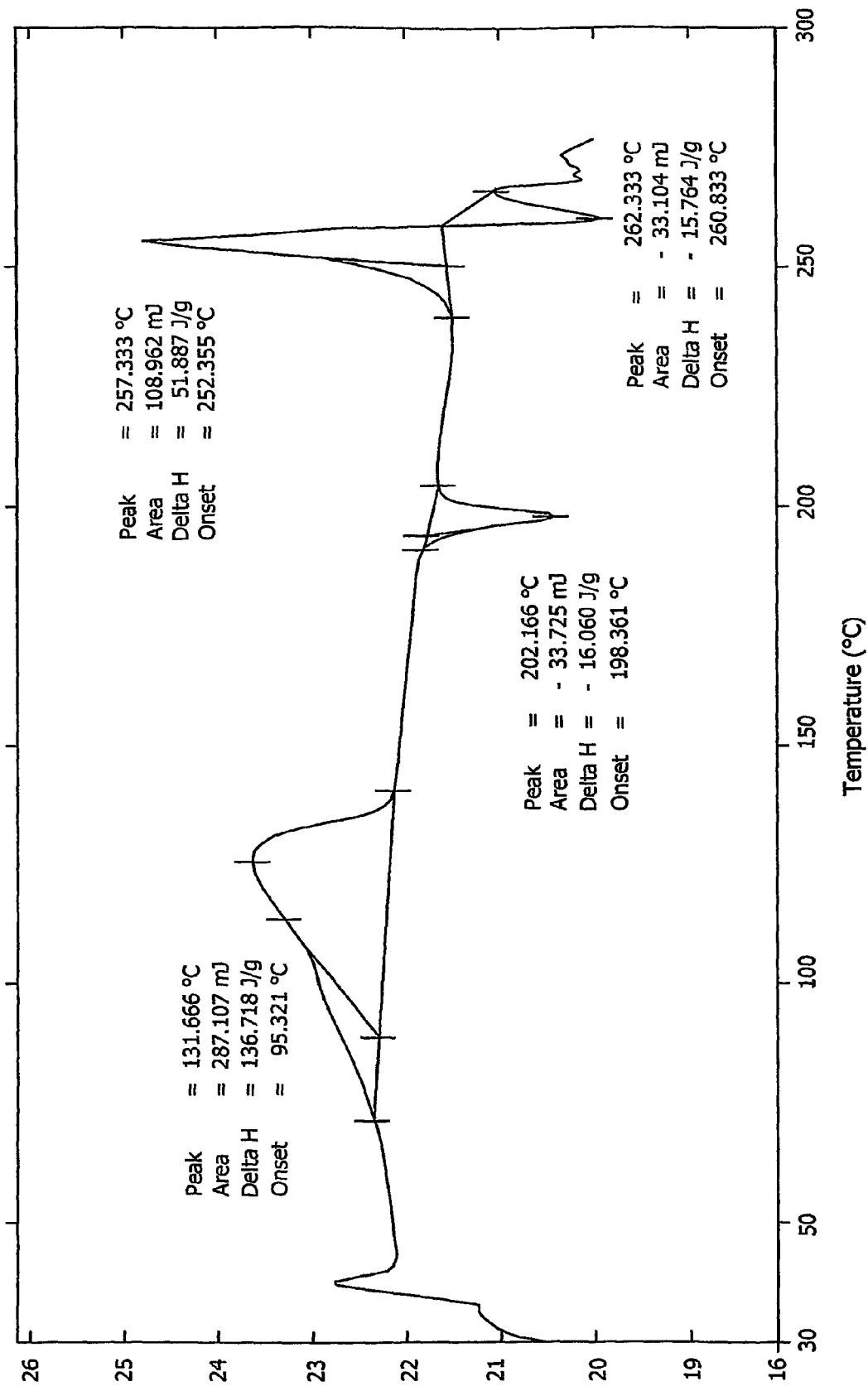
FIG. 19 represents a characteristic Differential Scanning Calorimetric (DSC) thermogram of the crystalline A-3 form of S-(−)-1-cyclopropyl-6-fluoro-8-methoxy-7-(4-amino-3,3-dimethylpiperidin-1-yl)-1,4-dihydro-4-oxo-quinoline-3-carboxylic acid hydrochloride of the invention.
Figure 29:
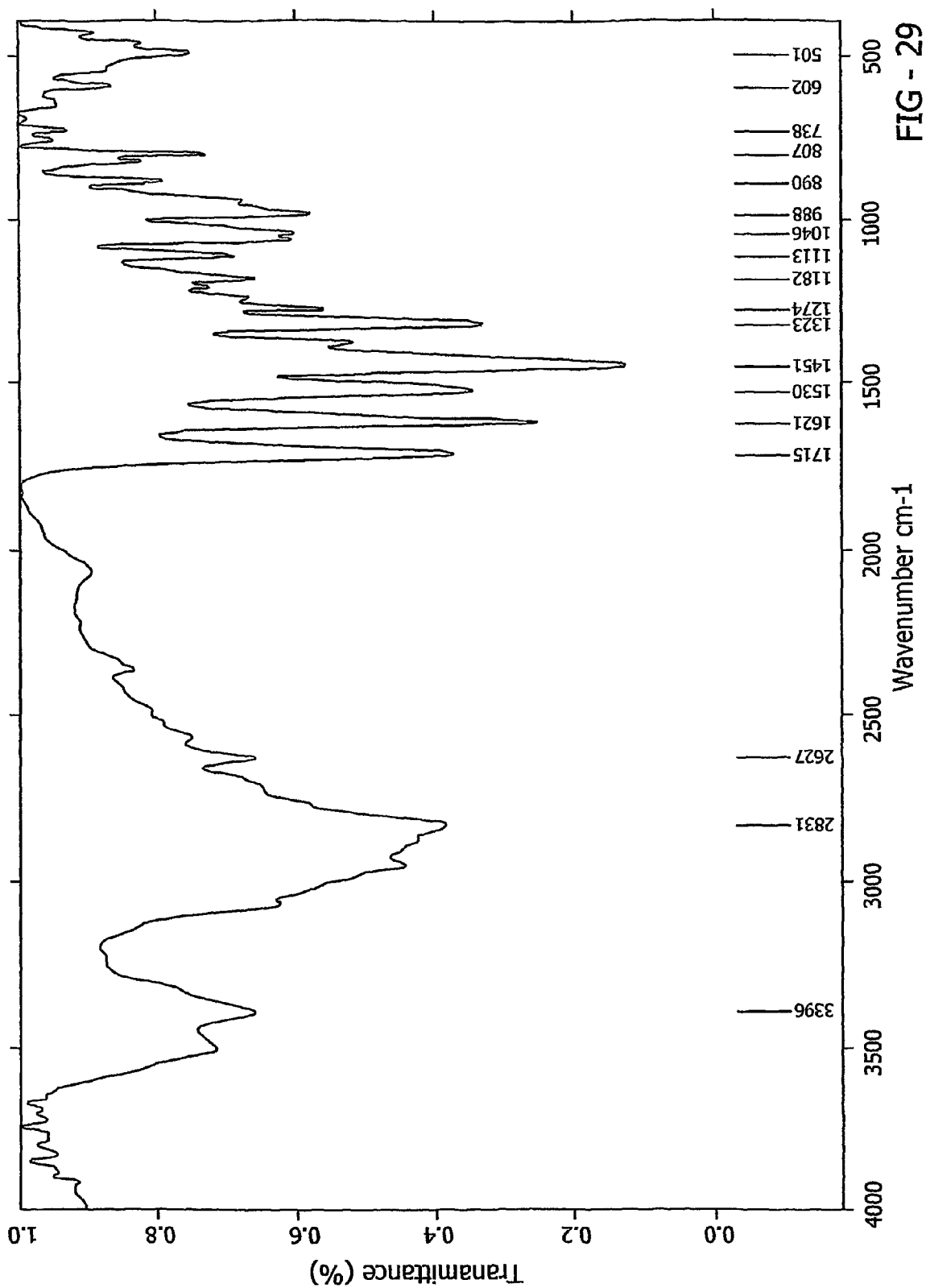
FIG. 29 represents a characteristic Infra-red (IR) spectrum of the crystalline A-3 form of S-(−)-1-cyclopropyl-6-fluoro-8-methoxy-7-(4-amino-3,3-dimethylpiperidin-1-yl)-1,4-dihydro-4-oxo-quinoline-3-carboxylic acid hydrochloride of the invention.

Analysis: FIG. 9, 19 and 29.

Powder X-ray diffraction (2θ): 7.04±0.2°, 7.70±0.2°, 8.06±0.2°, 12.34±0.2°, 12.78±0.2°, 13.64±0.2°, 15.40±0.2°, 16.14±0.2°, 18.62±0.2°, 19.40±0.2°, 20.64±0.2°, 21.84±0.2°, 23.22±0.2°, 26.80±0.2°, 27.88±0.2°, 29.86±0.2°, 32.30±0.2°, 33.36±0.2°, 37.02±0.2°, 39.24±0.2°;

DSC: endotherm at 131.66° C. (onset at 95.32° C.) exotherm at 202.16° C. (onset at 198.36° C.), endotherm at 257.33° C. (onset at 252.35° C.));

Infrared spectrum selected peaks (cm$^{-1}$): 3396, 1715, 1621, 1530, 1451, 1274.

Alternatively, polymorph A-1 may also be converted to polymorph A-3 by dissolving A-1 in an aqueous solution of a salt of an inorganic acid, preferably sodium chloride, optionally by heating if necessary, to obtain a clear solution, maintaining the solution at temperatures of 3-5° C. to effect the transformation completely to polymorphic form A-3, and recovering the polymorphic form A-3 as a crystal. The resultant crystals are dried to a constant weight to yield the polymorph A-3 of the invention.

According to FIG. 38 polymorphic form A-3 may also be formed is a second sequence from Polymorphic form A-2. Polymorph A-2 may be prepared according to the method of Example 106 of our pending US patent application No. 2003/0216568, the disclosure of which is hereby incorporated-herein by reference in-its entirety. Polymorphic form A-2 of S-(−)-1-cyclopropyl-6-fluoro-8-methoxy-7-(4-amino-3,3-dimethylpiperidin-1-yl)-1,4-dihydro-4-oxo-quinoline-3-carboxylic acid hydrochloride, having Powder X-ray diffraction spectrum as shown in FIG. 2 is suspended or dissolved in water, if necessary by heating at 80-100° C. to form a solution, cooling to a temperature of 30-40° C. and adding a water-miscible organic solvent. Suitable solvents include $C_1$-$C_6$ alkanols, preferably isopropanol. The resulting mixture is stirred for a sufficient period of time, preferably up to 12 hours to effect the transformation completely to polymorphic form A-3, and recovering the polymorphic form A-3 as a crystal upon cooling the solution. The resultant crystals are dried to a constant weight to yield the polymorph A-3 of the invention.

Referring to FIG. 38, polymorph Am is prepared from polymorphs A-1, A-2 and A-3 by vacuum drying polymorphic forms A-1 or A-2 or A-3 at an elevated temperature, preferably 130° C. up to 150° C. optionally under reduced pressure for a time, preferably up to 12 hours, and recovering the polymorphic form A-4 as a crystalline solid.

Figure 10:
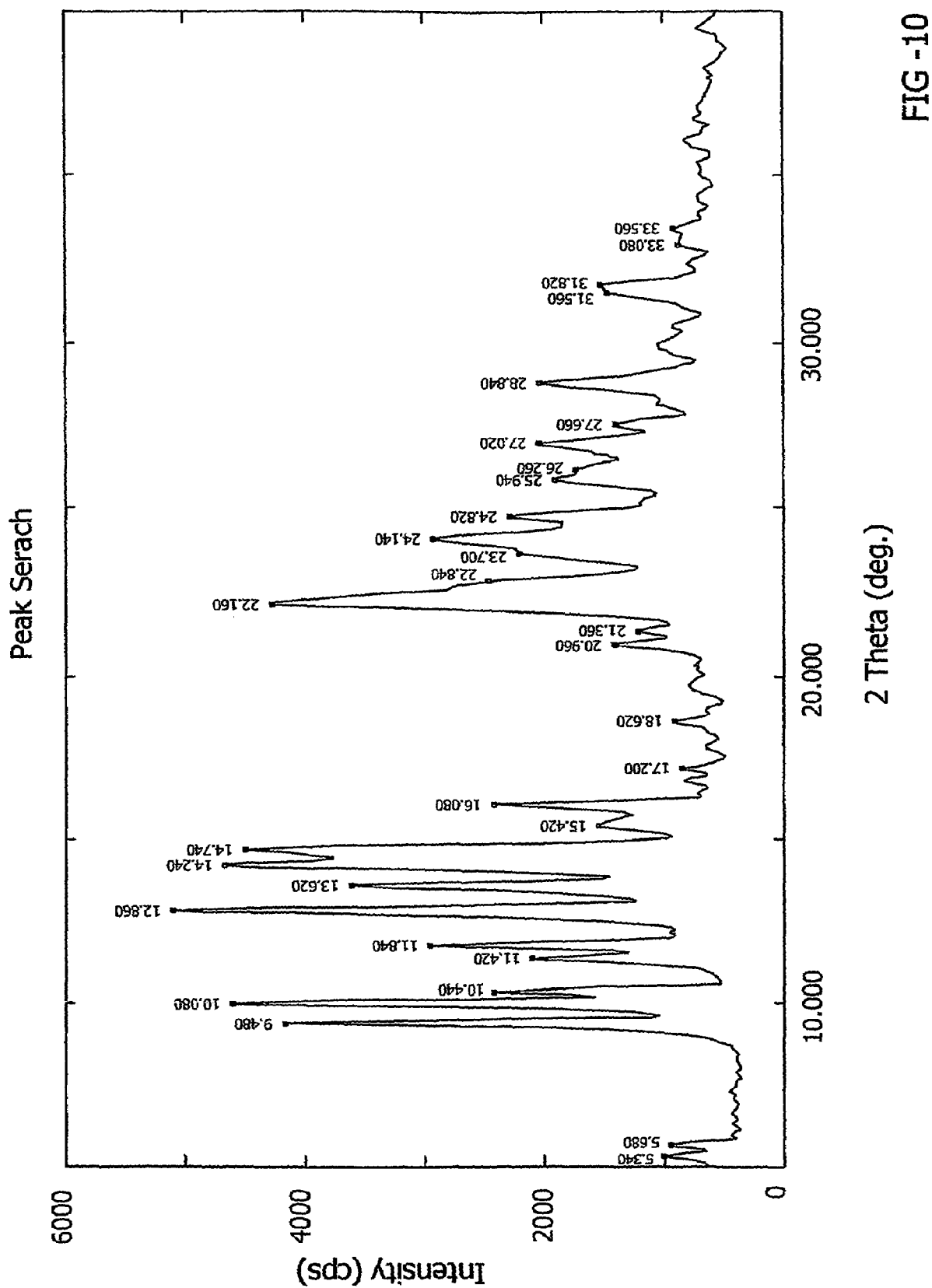
FIG. 10 represents a characteristic Powder X-ray diffraction (XRPD) spectrum of the crystalline A-4 form of S-(−)-1-cyclopropyl-6-fluoro-8-methoxy-7-(4-amino-3,3-dimethylpiperidin-1-yl)-1,4-dihydro-4-oxo-quinoline-3-carboxylic add hydrochloride of the invention.
Figure 20:
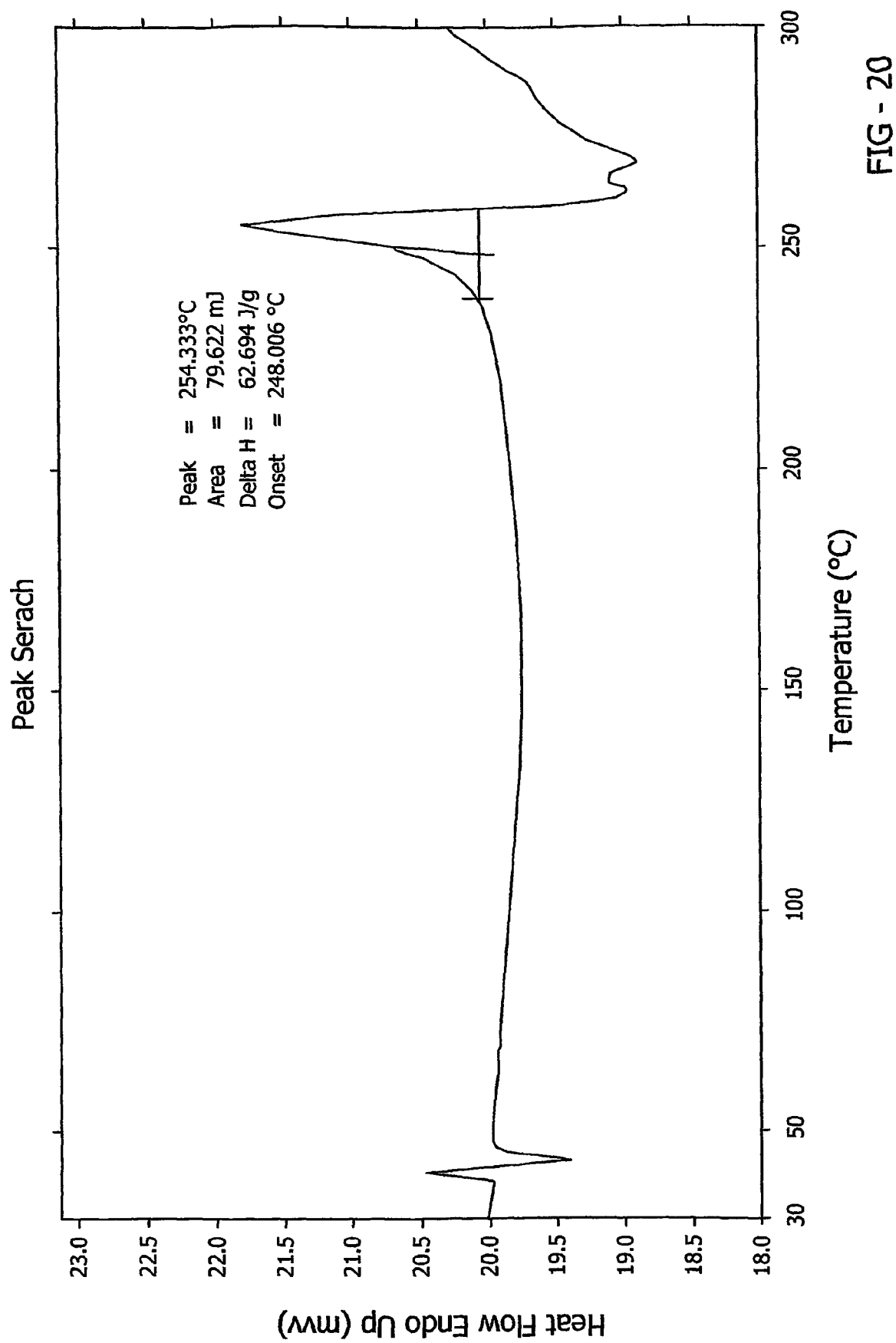
FIG. 20 represents the Differential Scanning Calorimetric (DSC) thermogram of the crystalline A-4 form of S-(−)-1-cyclopropyl-6-fluoro-8-methoxy-(4-amino-3,3-dimethylpiperidin-1-yl)-1,4-dihydro-4-oxo-quinoline-3-carboxylic acid hydrochloride of the invention.
Figure 30:
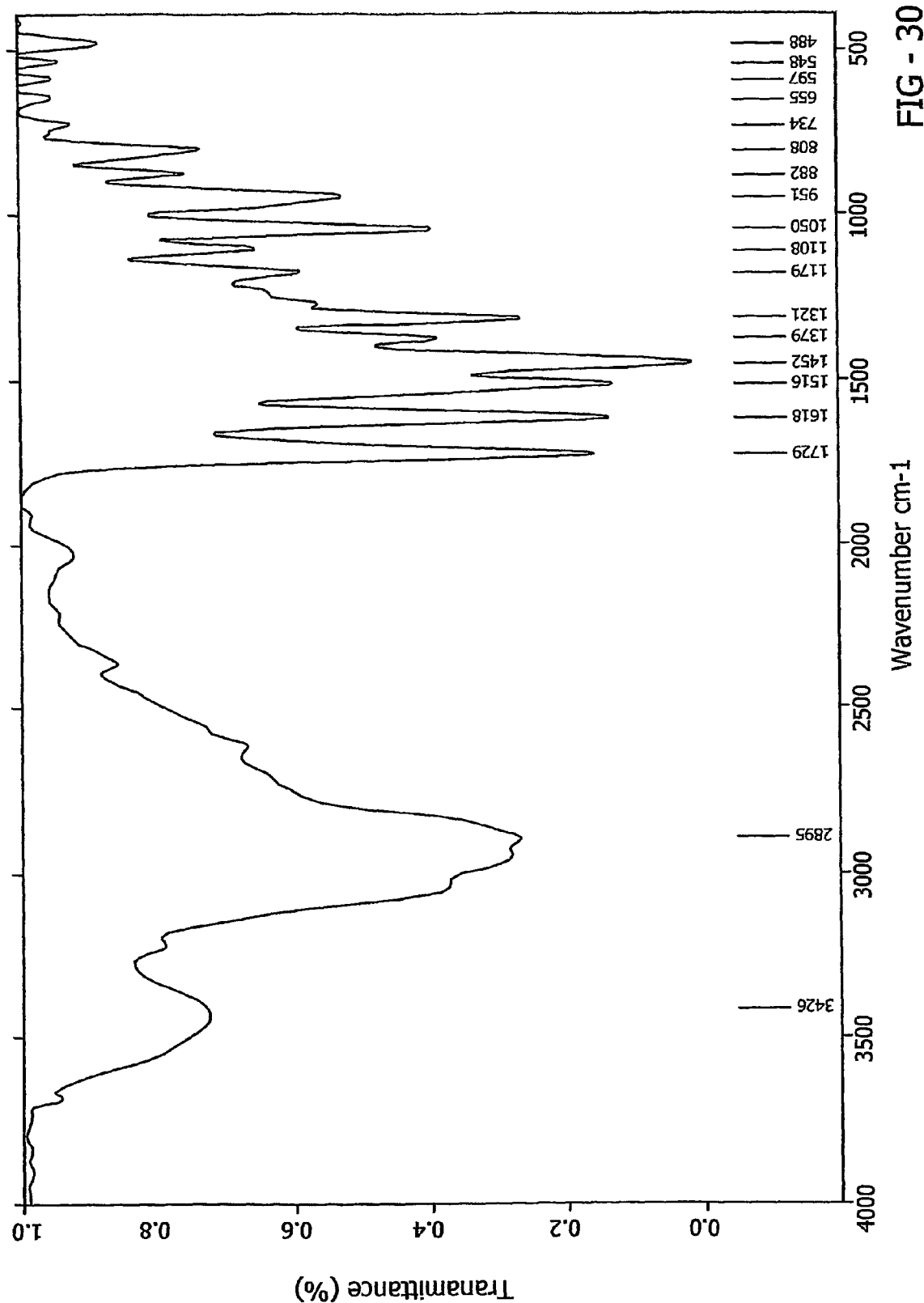
FIG. 30 represents the Infra-red (IR) spectrum of the crystalline A4 form of S-(−)-1-cyclopropyl-6-fluoro-8-methoxy-7-(4-amino-3,3-dimethylpiperidin-1-yl)-1,4-dihydro-4-oxo-quinoline-3-carboxylic acid hydrochloride of the invention.

Analysis: FIG. 10, 20 and 30.

Powder X-ray diffraction (2θ): 5.34±0.2°, 5.68±0.2°, 9.48±0.2°, 10.08±0.2°, 10.44±0.2°, 11.42±0.2°, 11.84±0.2°, 12.86±0.2°, 13.62±0.2°, 14.24±0.2°, 14.74±0.2°, 16.08±0.2°, 22.16±0.2°, 24.14±0.2°, 24.82±0.2°, 25.94±0.2°, 27.02±0.2°, 28.84±0.2°, 31.82±0.2°;

DSC: endotherm at 254.33° C. (onset at 248.00° C.);

Infrared spectrum (cm$^{-1}$): 2895, 1729, 1618, 1516, 1452, 1379, 1321, 1179, 1108, 1050, 951, 882, 808, 734.

Polymorph A-4 can be converted to polymorph A-3 according to a third sequence in FIG. 37, by treatment with water and isopropanol as indicated above with respect to the conversion of polymorph A-2 to polymorph A-3. The water may be in the form of liquid or vapour.

Referring to FIG. 38, polymorph B-1 is prepared from S-(−)-1-cyclopropyl-6-fluoro-8-methoxy-7-(4-amino-3,3-dimethylpiperidin-1-yl)-1,4-dihydro-4-oxo-quinoline-3-carboxylic acid. S-(−)-1-cyclopropyl-6-fluoro-8-methoxy-7-(4-amino-3,3-dimethylpiperidin-1-yl)-1,4-dihydro-4-oxo-quinoline-3-carboxylic acid, described as Example 17 in our pending US application Nos. 2003/0096812 and 2003/0216568, is suspended or dissolved in a suitable organic solvent such as $C_1$-$C_6$ alkanols, preferably isopropanol or $C_1$-$C_6$ alkyl esters of $C_1$-$C_6$ alkanoic acids, preferably ethyl acetate, or acetonitrile to form a suspension/solution, heating the suspension/solution to a temperature between about 25° C. and 80° C.; adding methane sulfonic acid to the suspension/solution, heating at a temperature of 70-80° C. for a period of time, preferably 1 hour, and recovering the polymorphic form B-1 as a crystal upon cooling the solution. The resultant crystals are dried to a constant weight to yield the polymorph B-1 of the invention.

Figure 13:
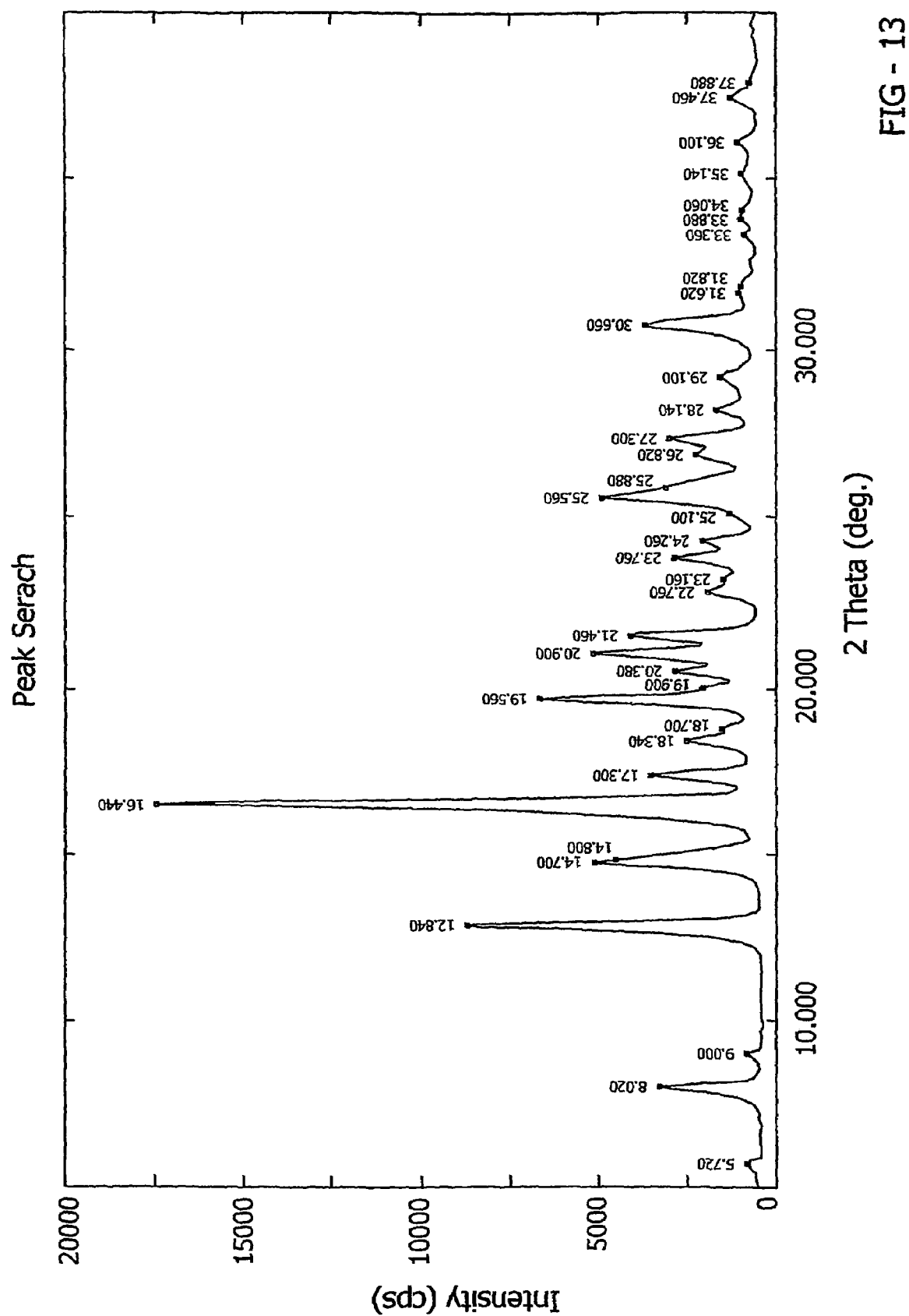
FIG. 13 represents the Powder X-ray diffraction (XRPD) spectrum of the crystalline B-1 form of S-(−)-1-cyclopropyl-6-fluoro-8-methoxy-7-(amino-3,3-dimethylpiperdin-1-yl)-1,4-dihydro--oxo-quinoline-3-carboxylic acid mesylate of the invention.
Figure 23:
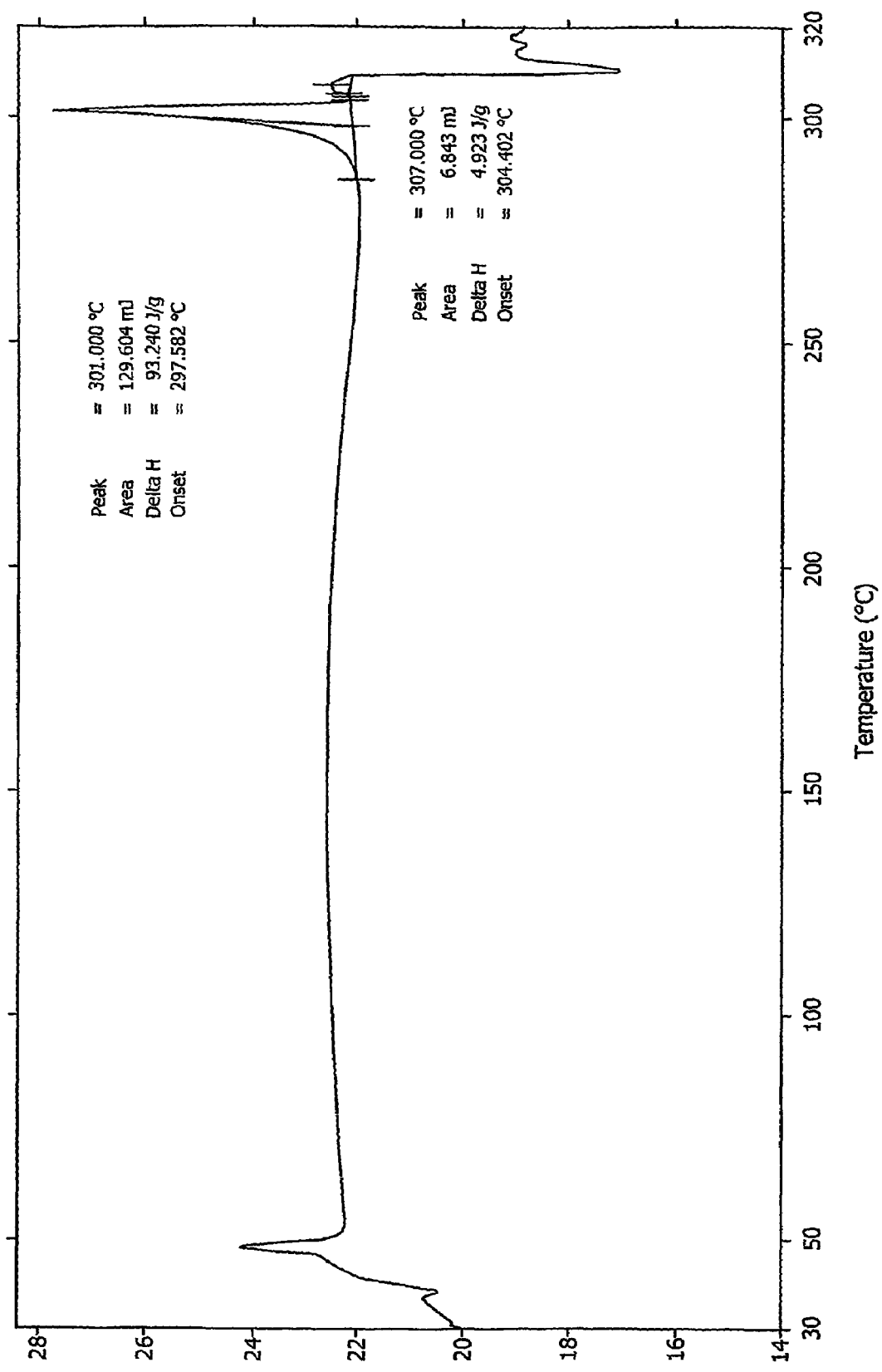
FIG. 23 represents the Differential Scanning Calorimetric (DSC) thermogram of the crystalline B-1 form of S-(−)-1-cyclopropyl-6-fluoro-8-methoxy-7-(4-amino-3,3-dimethylpiperidin-1-yl)-1,4-dihydro-4-oxo-quinoline-3-carboxylic acid mesylate of the invention.
Figure 33:
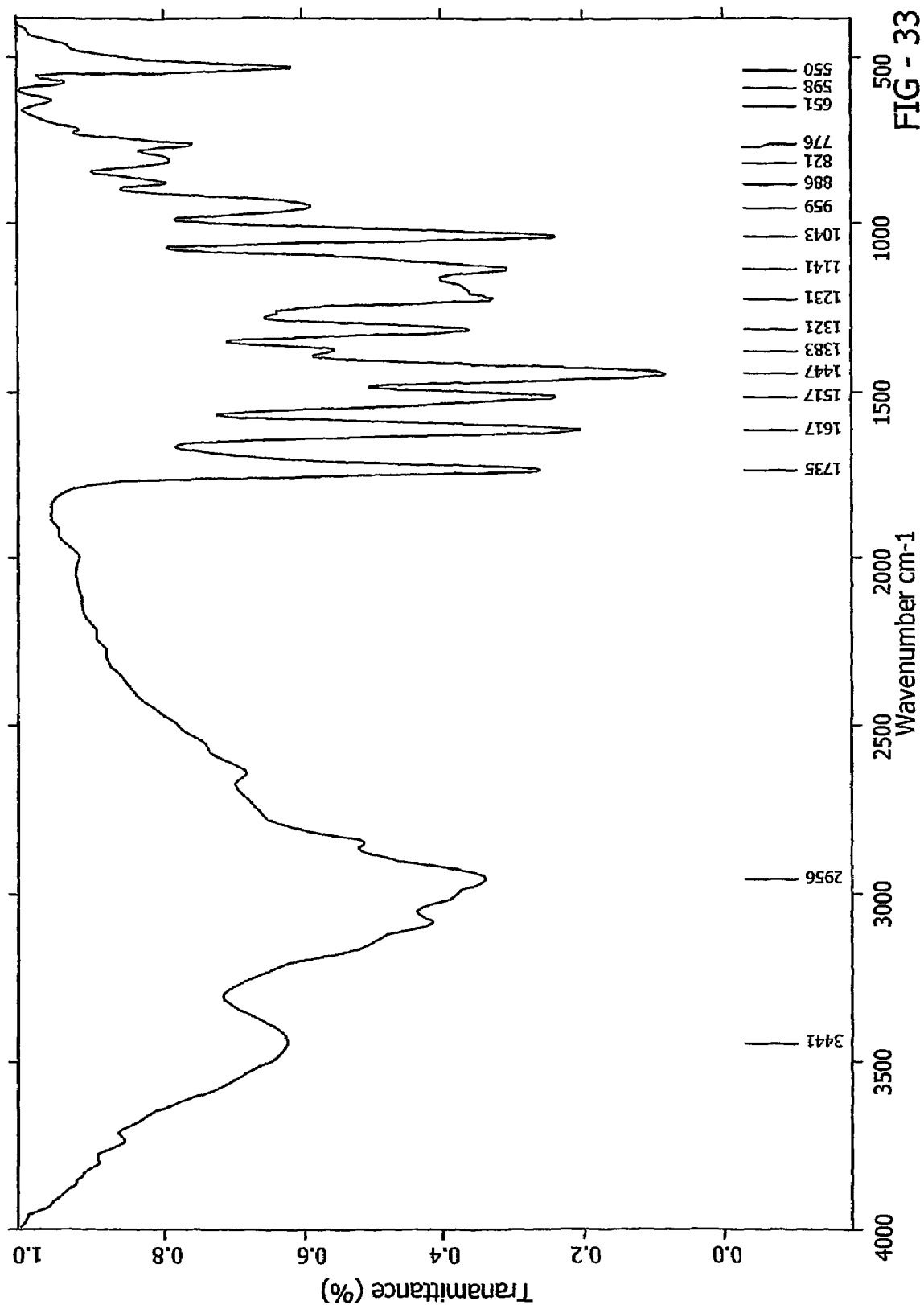
FIG. 33 represents the Infra-red (IR) spectrum of the crystalline B-1 form of S-(−)-1-cyclopropyl-6-fluoro-8-methoxy-7-(4-amino-3,3-dimethylpiperidin-1-yl)-1,4-dihydro-4-oxo-quinoline-3-carboxylic acid mesylate of the invention.

Analysis: FIG. 13, 23 and 33.

Powder X-ray diffraction (2θ): 8.02±0.2°, 12.84±0.2°, 14.70±0.2°, 16.44±0.2°, 17.30±0.2°, 19.56±0.2°, 20.90±0.2°, 21.46±0.2°, 23.76±0.2°, 25.56±0.2°, 27.30±0.2°, 30.66±0.2°, 37.46+0.2°;

DSC: endotherm at 301.00° C. (onset at 297.58° C.).

Infra-red spectrum (cm$^{-1}$): 3441, 2956, 1735, 1617, 1517, 1447, 1321, 1231, 1141, 1043, 886, 821, 776.

Referring to FIG. 38 polymorph B-2 is prepared from polymorph B1 by dissolving crystalline polymorphic form B-1 of S-(−)-1-cyclopropyl-6-fluoro-8-methoxy-7-(4-amino-3,3-dimethylpiperidin-1-yl)-1,4dihydro-4-oxo-quinoline-3-carboxylic acid mesylate in water by heating at a temperature between 25-100° C., preferably 80-100° C. to form a solution; cooling the solution to 25-35° C. and adding an aqueous-miscible organic solvent. A suitable organic solvent includes $C_1$-$C_6$ alkanols, preferably isopropanol, or $C_3$-$C_6$ aliphatic ketones, preferably acetone, or acetonitrile. The reaction mixture is allowed to stand for 24 hrs, and subsequent recovery of the polymorphic form B-2 as a crystal upon cooling. The resultant crystals are dried to a constant weight to yield the polymorph B-2 of the invention.

Figure 16:
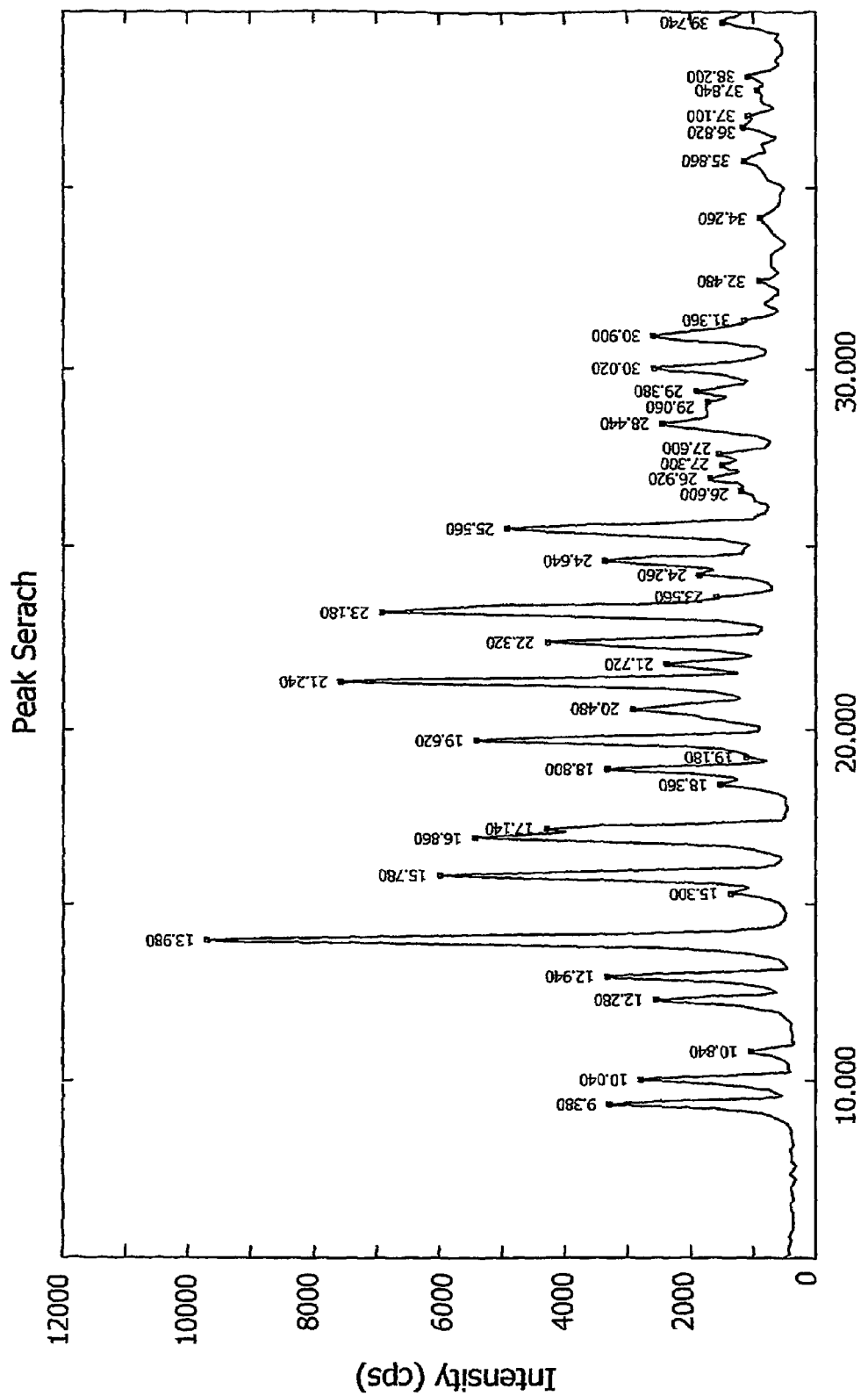
FIG. 16 represents the Powder X-ray diffraction (XRPD) spectrum of the crystalline B-2 form of S-(−)-1-cyclopropyl-6-fluoro-8-methoxy-7-(4-amino-3,3-dimethylpiperidin-1-yl)1,4-dihydro-4-oxo-quinoline-3-carboxylic acid mesylate of the invention.
Figure 26:
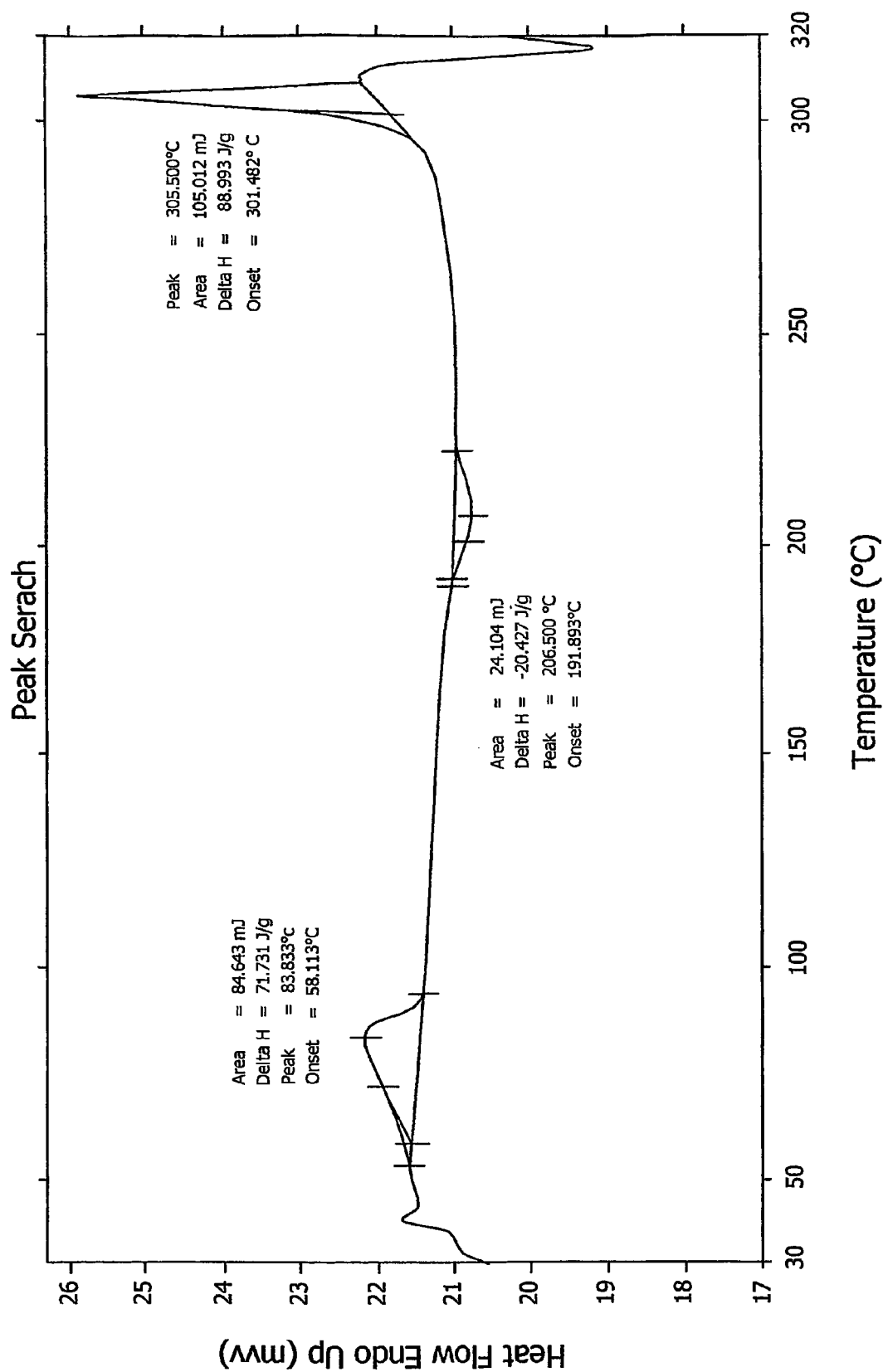
FIG. 26 represents the Differential Scanning Calorimetric (DSC) thermogram of the crystalline B-2 form of S-(−)-1-cyclopropyl-6-fluoro-8-methoxy-7-(4-amino-3,3-dimethylpiperidin-1-yl)-1,4-dihydro-4-oxo-quinoline-3-carboxylic acid mesylate of the invention.

Analysis: FIG. 16, 26 and 36.

Powder X-ray diffraction (2θ): 9.38±0.2°, 10.04±0.2°, 12.28±0.2°, 12.94±0.2°, 13.98±0.2°, 15.78±0.2°, 16.86±0.2°, 18.80±0.2°, 19.62±0.2°, 21.24±0.2°, 22.32±0.2°, 23.18±0.2°, 24.64±0.2°, 25.56±0.2°, 28.44±0.2°, 30.02±0.2°, 30.90±0.2°, 39.74±0.2°;

DSC: exotherm at 83.83° C. (onset at 58.11° C.), endotherm at 305.50° C. (onset at 301.48° C.);

Infra-red spectrum ($cm^{-1}$): 3486, 1728, 1624, 1521, 1460, 1325, 1191, 1047, 879, 781.

The polymorphs may be isolated from the various mixtures by techniques known to those of skill in the art. The compounds of the invention may be obtained for example, by crystallizing or by precipitating the compound of the invention from the appropriate solvent or solvent mixture. Some of the compounds of the invention may be obtained by transforming one polymorph into another by heating one polymorph optionally under reduced pressure.

Mesylate salt polymorphs B-1 and B-2 have higher aqueous solubility as shown below over all hydrochloride salt polymorphs, including those disclosed in our earlier applications.

| Salt | Polymorph | Aqueous Solubility at 25-30° C. (mg/ml) |
|---|---|---|
| Hydrochloride Salts | (±)/(+)/(−) A-1 | 40-50 |
| | (±)/(+)/(−) A-2 | 4-10 |
| | (±)/(+) A-3 anhydrous | <2 |
| | (−) A-3 | 10 |
| | (−) A-4 anhydrous | <2 |
| Mesylate Salts | (±)/(+)/(−) B-1 | 80-200 |
| | (±)/(+)/(−) B-2 | 100-200 |

Percent relative humidity stability study and aqueous solubility data discloses that—

Polymorphs A-2 of (+) and (−) and A-3 of (−) are thermodynamically stable polymorphs.

Polymorphs (±) and (+) A-1 and A-3 changed to polymorph A-2 when the solid is kept for 20 days in 78% relative humidity, thereby changing the Powder X-ray Diffraction spectrum and aqueous solubility of original polymorphs.

Polymorphs (−) A-1, A-2 and A-4 changed to polymorph A-3 when the solid is kept for 20 days in 78% relative humidity, thereby changing the Powder X-ray Diffraction spectrum and aqueous solubility of original polymorphs.

Thermodynamically stable form is an essential prerequisite for pharmaceutical pre-formulation of solids. The thermodynamically stable form is an advantageous feature for increasing the shelf life and ease of storage conditions and packaging.

Hence, the polymorphs A-2 of previous application and A-3 and B-2 included in the current specification have the advantages over known compounds and polymorphs.

The present invention also relates to pharmaceutical compositions containing or made using an antibacterially effective amount of one or more of a polymorph of racemic (±), dextrorotatory R-(+), or levorotatory S-(−) enantiomer of 1-cyclopropyl-6-fluoro-8-methoxy-7-(4-amino-3,3-dimethylpiperidin-1-yl)-1,4-dihydro-4-oxo-quinoline-3-carboxylic acid hydrochloride and mesylate of formula I and II respectively as described above (e.g. the polymorphs of the invention) together with a pharmaceutically acceptable carrier. The present invention also relates to a method for treating bacterial infection in a human or non-human mammal or other animal which comprises administrating to the subject in need of such treatment a therapeutically or prophylactially effective amount of such a pharmaceutical composition or polymorph.

The antibacterial polymorphic compounds of the invention of formula I and II that can be synthesized using, for example, the methods and intermediates of this invention are useful in the treatment of mammals having a broad spectrum of bacterial infections as extensively described in the co-pending US patent application publications 2003/0096812 and 200310216568.

In an embodiment of the invention, the pharmaceutical compositions contain an effective amount of the active compounds of the invention described in this specification in admixture with a pharmaceutically acceptable carrier, diluent or excipients, and optionally other therapeutic ingredients.

The present invention also encompasses an antiinfective composition for the treatment of humans and animals in need of prophylaxix and/or therapy for systemic or topical infections especially resistant gram-positive organism infections, gram-negative organism infections, mycobacterial infections and nosocomial pathogen infections, which composition comprises an amount of a compound of the invention, substantially sufficient to eradicate said Infection, but not to cause any undue side effects. Compounds and compositions of this invention can be administered to humans and animals who are at risk of being infected, for example a compound or composition of this invention can be administered to a patient prior to and/or after surgery.

In addition the compounds of the invention have superior bactericidal activity against pneumococci and streptococci of various groups. Cidal features available in such molecules add to their clinical attractiveness as it would offer clinicians a valuable treatment option to treat a broader range of infections caused by staphylococci, MRSA, MRSE, pneumococci, streptococci, mycobacteria and diverse range of anaerobic bacteria of clinical importance in a situation such as patients allergic to flactam or possibility of infections due to macrolide resistant strains of streptococci and pneumococci or MRSA/QRSA. For anaerobic bacterial infections, currently available treatment options are rather limited due to reasons such as inadequate potency or gaps in the spectrum of anaerobic pathogens covered. Such is the case with macrolides. With β-lactam antibacterials, the major shortcoming is their liability to a variety of β-lactamases, the drug inactivating enzymes elaborated by commonly encountered anaerobic pathogens. Older fluoroquinolones such as ciprofloxacin, levofloxacin, pefloxacin also suffered due to inadequate anti-anaerobic potency. The molecules of invention demonstrate several distinct gains in antimicrobial properties against anaerobic pathogens vis-à-vis earlier antibacterial agents of the β-lactam, macrolide and fluoroquinolone classes.

It has been found that the compounds of this invention, and compositions containing these compounds, are effective antimicrobial agents against a broad range of pathogenic microorganisms with advantages in low susceptibility to microbial resistance, reduced toxicity, and improved pharmacology.

Moreover, the compounds of the invention also retain the other valuable features, of being bactericidal to fluoroquinolone resistant staphylococci (QRSA with resistant gyrase) and even to staphylococcal and pneumococcal isolates possessing Nor A efflux pumps and other efflux pumps. The compounds of the invention also display efflux pump inhibitory activity. A combination of all these properties coupled with overall good safety and tolerability observed in a new molecule renders them worthy of therapeutic use in humans and animals. By virtue of such features, they have considerable advantages over existing fluoroquinolone antibacterials, in particular in the treatment of respiratory diseases and infections of skin and soft tissue.

The above list of pathogens is merely by way of example and is in no way to be interpreted as limiting. *Streptococci* are implicated as one of the most common pathogens, in both the pediatric and adult population in diverse infections/diseases. Examples which may be mentioned of diseases, which can thus be prevented, alleviated and/or cured by the formulations according to the invention include but are not limited to are meningitis, otitis extema, otitis media; pharyngitis; pneumonia; life-threatening bacteremia, peritonitis; pyelonephritis; cystitis; endocarditis; systemic infections; bronchitis; arthritis; local infections; and septic diseases. Several molecules of the present inventions also exhibit impressive gains in potency against *Mycobactedum tuberculosis* and therefore of potential value in the treatment of latent and recalcitrant mycobacterial infections such as tuberculosis.

These findings have an important implication from the point of view of the systemic use of the compounds of the invention in view of their superior potency, superior bactericidal activity, expanded biospectrum, better bioavailability and improved tolerability which are now enabled to be administered systemically in therapeutically effective doses.

Utilizing the compounds of the invention whether in systemic or topical dosage form, results in clearer dose-related definitions of efficacy, diminished toxic effects and accordingly an improved therapeutic index.

The present invention encompasses certain compounds, dosage forms, and methods of administering the compounds to a human or other animal subject. Specific compounds and compositions to be used in the invention must, accordingly, be pharmaceutically acceptable. As used herein, such a "pharmaceutically acceptable" component is one that is suitable for use with humans and/or animals without undue adverse side effects (such as toxicity, irritation, and allergic response) commensurate with a reasonable benefit/risk ratio.

The pharmaceutical compositions are prepared according to conventional procedures used by persons skilled in the art to make stable and effective compositions. In the solid, liquid, parenteral and topical dosage forms, an effective amount of the active compound or the active ingredient is any amount, which produces the desired results.

For the purpose of this invention the pharmaceutical compositions may contain the active compounds of the invention in a form to be administered alone, but generally in a form to be administered in admixture with a pharmaceutical carrier selected with regard to the intended route of administration and standard pharmaceutical practice. The compounds retain their polymorphic identity even in solution (non-solid composition) e.g. some polymorphs show less aqueous solubility and some shows higher, owing to their polymorphic identity. Suitable carriers which can be used are, for example, diluents or excipients such as fillers, extenders, binders, emollients, wetting agents, disintegrants, surface active agents and lubricants which are usually employed to prepare such drugs depending on the type of dosage form.

Any suitable route of administration may be employed for providing the patient with an effective dosage of the compound of the invention their derivatives, salts and hydrates thereof. For example, oral, rectal, parenteral (subcutaneous, intramuscular, intravenous), transdermal, topical and like forms of administration may be employed. Dosage forms include (solutions, suspensions, etc) tablets, pills, powders, troches, dispersions, suspensions, emulsions, solutions, capsules, injectable preparations, patches, ointments, creams, lotions, shampoos and the like.

The prophylactic or therapeutic dose of the compounds of the invention in the acute or chronic management of disease Will vary with the severity of condition to be treated, and the route of administration. In addition, the dose, and perhaps the dose frequency, will also vary according to the age, body weight and response of the individual patient. In general, the total daily dose range, for the compounds of the invention, the derivatives, salts or hydrates thereof, for the conditions described herein, is from about 200 mg to about 1500 mg, in single or divided doses. Preferably, a daily dose range should be between about 400 mg to 1200 mg, in single or divided dosage, while most preferably a daily dose range should be between about 500 mg to about 1000 mg in divided dosage. While intramuscular administration may be a single dose or up to 3 divided doses, intravenous administration can include a continuous drip. It may be necessary to use dosages outside these ranges in some cases as will be apparent to those skilled in the art. Further, it is noted that the clinician or treating physician will know how and when to interrupt, adjust, or terminate therapy in conjunction with individual patient's response including the selection of the formulation, route of administration and dosage. The term "an amount sufficient to eradicate such infections but insufficient to cause undue side effects" is encompassed by the above-described dosage amount and dose frequency schedule. The term "an effective amount" means that amount of the compound or composition that will elicit the biological or medical response of a tissue, cell, system, animal, non-human mammal or human mammal that is being sought. This is intended to refer to situations where there may be a slowing, interrupting, arresting or stopping of the progression of the infection and may include prophylatic treatment of infections.

Pharmaceutical compositions of the present invention suitable for oral administration may be presented as discrete units such as capsules, cachets, or tablets, or aerosol sprays, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier, which constitutes one or more necessary Ingredients. In general, the compositions are prepared by uniformly and Intimately admixing the active ingredient with liquid carriers or finely divided solid carriers or both, and then, if necessary, shaping the product into the desired presentation.

The compositions of the present invention include compositions such as suspensions, solutions, elixirs, aerosols, and solid dosage forms. Carriers as described in general above are commonly used in the case of oral solid preparations (such as powders, capsules and tablets), with the oral solid preparations being preferred over the oral liquid preparations. The most preferred oral solid preparation is tablets.

Because of their ease of administration, tablets and capsules represent the most advantageous oral dosage unit form, in which case solid pharmaceutical carriers are employed. Examples of suitable carriers include excipients such as lactose, white sugar, sodium chloride, glucose solution, urea, starch, calcium carbonate, kaolin, crystalline cellulose and silicic acid, binders such as water, ethanol, propanol, simple syrup, glucose, starch solution, gelatin solution, carboxymethyl cellulose, shellac, methyl cellulose, potassium phosphate and polyvinyl pyrrolidone, disintegrants such as dried starch, sodium alginate, agar powder, laminaria powder, sodium hydrogen carbonate, calcium carbonate, Tween (fatty acid ester of polyoxyethylenesorbitan), sodium lauryl sulfate, stearic acid monoglyceride, starch, and lactose, disintegration inhibitors such as white sugar, stearic acid glyceryl ester, cacao butter and hydrogenated oils, absorption promoters such as quaternary ammonium bases and sodium lauryl sulfate, humectants such as glycerol and starch, absorbents such as starch, lactose, kaolin, bentonite and colloidal silicic acid, and lubricants such as purified talc, stearic add salts, boric acid powder, polyethylene glycol and solid polyethylene glycol.

The tablet, if desired, can be coated, and made into sugar-coated tablets, gelatin-coated tablets, enteric-coated tablets, film-coated tablets, or tablets comprising two or more layers.

If desired, tablets may be coated by standard aqueous or non-aqueous techniques.

In molding the pharmaceutical composition into pills, a wide variety of conventional carriers known in the art can be used. Examples of suitable carriers are excipients such as glucose, lactose, starch, cacao butter, hardened vegetable oils, kaolin and talc, binders such as gum arabic powder, tragacanth powder, gelatin, and ethanol, and disintegrants such as laminaria and agar.

In molding the pharmaceutical composition into a suppository form, a wide variety of carriers known in the art can be used. Examples of suitable carriers include polyethylene glycol, cacao butter, higher alcohols, gelatin, and semi-synthetic glycerides.

A second preferred method is parenterally for intramuscular, intravenous or subcutaneous administration.

A third preferred route of administration is topically, for which creams, ointments, shampoos, lotions, dusting powders and the like are well suited. Generally, an effective amount of the compound according to this invention in a topical form is from about 0.1% w/w to about 10% w/w of the total composition. Preferably, the effective amount of the compound of the invention is 1% w/w of the total composition.

In addition to the common dosage forms set out above, the compounds of the present invention may also be administered by controlled release means and/or delivery devices such as those described in U.S. Pat. Nos. 3,845,770; 3,916,899; 3,536,809; 3,598,123 and 4,008,719; the disclosures of which are hereby incorporated by reference.

Desirably, each oral dosage form contains from about 200 mg to about 1500 mg of the active ingredient. Most preferably, the solid oral dosage form such as a tablet, cachet or capsule contains either one of three dosages, about 200 mg, about 400 mg, or about 600 mg of the active ingredient.

When the pharmaceutical composition is formulated into an injectable preparation, in formulating the pharmaceutical composition into the form of a solution or suspension, all diluents customarily used in the art can be used. Examples of suitable diluents are water, ethyl alcohol, polypropylene glycol, ethoxylated isostearyl alcohol, polyoxyethylene sorbitol, and sorbitan esters. Sodium chloride, glucose or glycerol may be incorporated into a therapeutic agent.

The antimicrobial pharmaceutical composition may further contain ordinary dissolving aids, buffers, pain-alleviating agents, and preservatives, and optionally coloring agents, perfumes, flavors, sweeteners, and other drugs.

For topical application, there are employed as non-sprayable forms, viscous to semi-solid or solid forms comprising a carrier compatible with topical application and having a dynamic viscosity preferably greater than water. Suitable formulations include but are not limited to solutions, suspensions, emulsions, creams, ointments, powders, liniments, salves, aerosols, etc., which are, if desired, sterilized or mixed with auxiliary agents, e.g. preservatives, antioxidants, stabilizers, wetting agents, buffers or salts for influencing osmotic pressure, etc. For topical application, also suitable are sprayable aerosol preparations wherein the active ingredient preferably in combination with a solid or liquid inert carrier material.

A specific embodiment of the invention is the preparation of storage stable compositions of the compounds of the invention of formula I. Such stable compositions can be advantageously made through the use of selective stabilizers. Different stabilizers are known to those skilled in the art of making pharmaceutical compositions. Of special utility for making storage stable compositions of the compound of the invention of formula I, stabilizers such as disodium ethylenediaminetetraacetic acid (EDTA), tromethamine, cyclodextrins such as gamma-cyclodextrin, hydroxy-propyl-gamma-cyclodextrin have been found to be useful.

The following preparations and examples illustrate the methods of preparation of the compounds of the invention and are provided only as examples, and are not intended to limit the scope of the compounds of the invention. It will be apparent to those skilled in the art that many modifications, both to materials and methods may be practiced without departing from the purpose and scope of this invention.

DSC, IR and X-Ray diffraction analysis of the compounds of invention were carried out as described in Test Examples 1, 2 and 3.

TEST EXAMPLE—1

Powder X-Ray Diffraction Analysis of the Forms of the Invention

Approximately 300 mg of the test sample was thinly spread on a sample holder. Powder X-ray diffraction analyses (40 kv×40 mA Rigaku D/max 2200) were performed under the conditions listed below:

Scan speed 5°/min
Sampling time 7 min
Scan mode: continuous
2θ/θ reflection
Cu target (Ni filter)

TEST EXAMPLE—2

Thermal Analysis of the Forms the Invention

For the Differential Scanning Calorimetry, PERKIN-ELMER DSC 7 system was used. 3-5 mg of the teat sample was weighed into the aluminum pan, press sealed with an aluminium lid. After three tiny needle holes were made on the lid, the sample was analyzed by heating either from 30° C. to 300° C. or from 30° C. to 320° C. at a rate of 10° C./min.

TEST EXAMPLE—3

Infra-Red Spectrum Analysis of the Forms the Invention

Infra-red spectrum was obtained on BRUKER VECTOR 22 system and by using KBr pellet.

Preparations

The polymorphs A-1 and A-2 of (±)-1-cyclopropyl-6-fluoro-8-methoxy-7-(4-amino-3,3-dimethylpiperidin-1-yl)-1,4-dihydro-oxo-quinoline-3-carboxylic acid hydrochloride were prepared as per Example Nos. 103 and 104 respectively described in our co-pending US Patent application No. US 20030216568. The Powder X-ray diffraction spectra of polymorphs A-1 and A-2 are shown in FIGS. 1 and 2 respectively.

The polymorphs A-1 and A-2 of R-(+)-1-cyclopropyl-6-fluoro-8-methoxy-7-(4-amino-3,3-dimethylpiperidin-1-yl)-1,4-dihydro-4-oxo-quinoline-3-carboxylic acid hydrochloride_were prepared as per Example Nos. 107 and 108 respectively described in our co-pending US Patent application No. US 20030216568. The Powder X-ray diffraction spectra of polymorphs A-1 and A-2 are shown in FIGS. 3 and 4 respectively.

Figure 5:
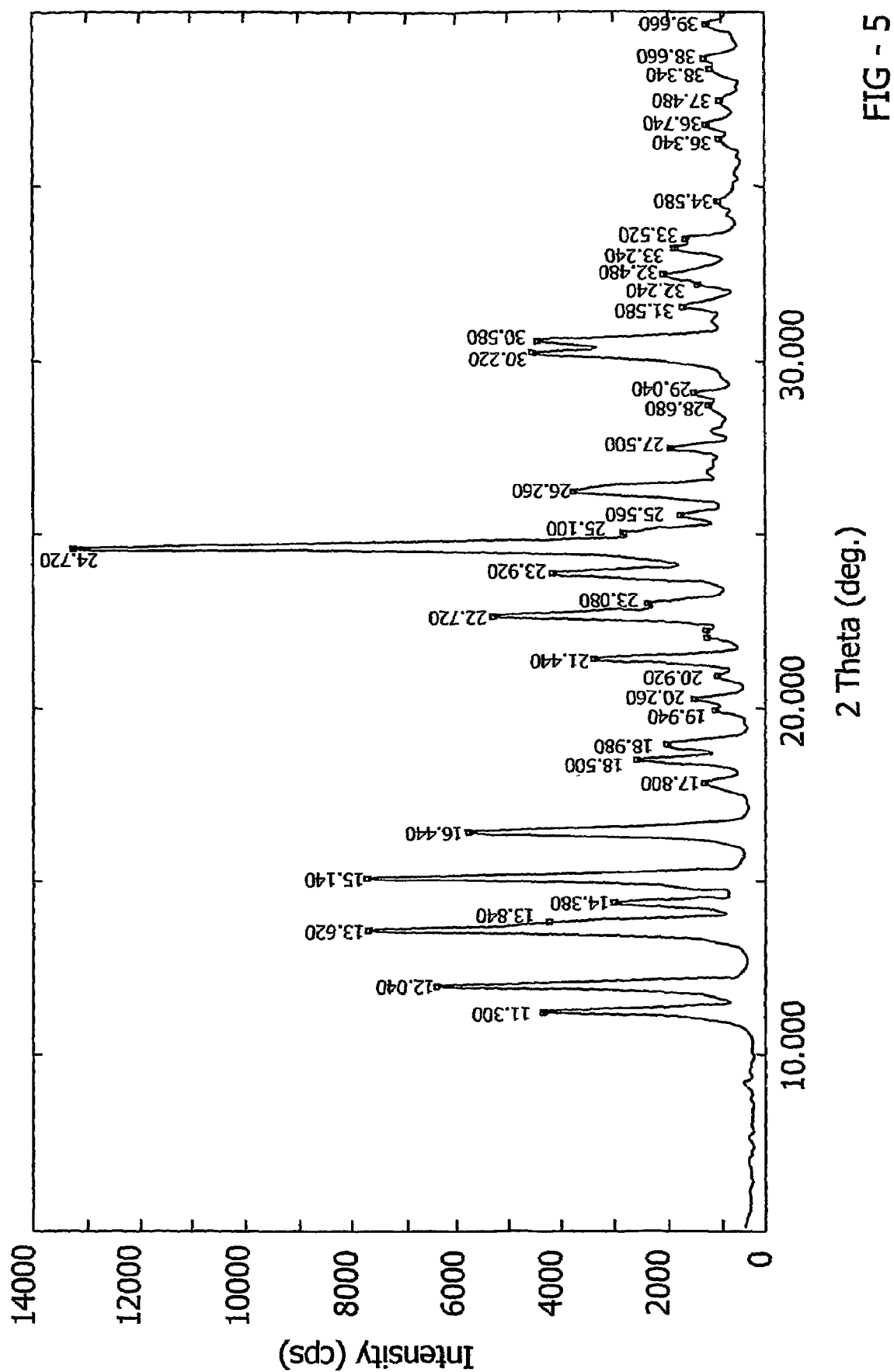
FIG. 5 represents a characteristic Powder X-ray diffraction (XRPD) spectrum of the crystalline A-1 form of S-(−)-1-cyclopropyl-6-fluoro-8-methoxy-7-(4-amino-3,3-dimethylpiperidin-1-yl)-1,4-dihydro-4-oxo-quinoline-3carboxylic acid hydrochloride prepared by the methods described in our pending US application No. 2003/0216568.
Figure 6:
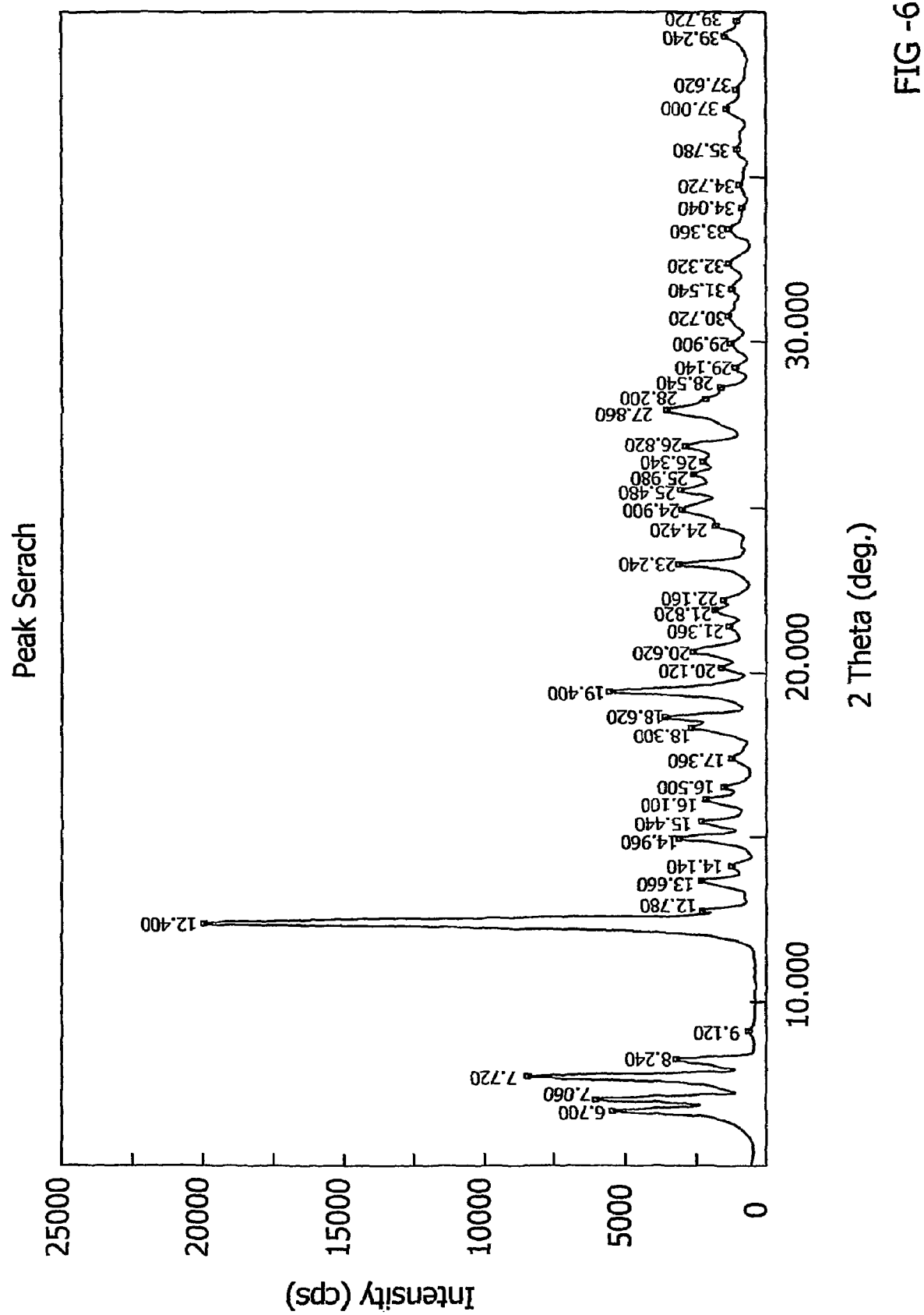
FIG. 6 represents a characteristic Powder X-ray diffraction (XRPD) spectrum of the crystalline A-2 form of S-(−)-1-cyclopropyl-6-fluoro-8-methoxy-7-(4-amino-3,3-dimethylpiperidin-1-yl)-1,4-dihydro-4-oxo-quinoline-3-carboxylic acid hydrochloride prepared by the methods described in our pending US application No. 2003/0216568.

The polymorphs A-1 and A-2 of S-(−)-1-cyclopropyl-6-fluoro-8-methoxy-7-(amino-3,3-dimethylpiperidin-1-yl)-1,4-dihydro-4-oxo-quinoline-3-carboxylic acid hydrochloride_were prepared as per Example Nos. 105 and 106 respectively described In our co-pending US Patent application No. 2003/0216568. The Powder X-ray diffraction spectra of polymorphs A-1 and A-2 are shown in FIGS. 5 and 6 respectively.

The free base (±)-1-cyclopropyl-6-fluoro-8-methoxy-7-(4-amino-3,3-dimethylpiperidin-1-yl)-1,4-dihydro-4-oxo-quinoline-3-carboxylic acid was prepared as per Example No.10 described in our co-pending US Patent applications No. US 20030216568.

The free base R-(+)-1-cyclopropyl-6-fluoro-8-methoxy-7-(4-amino-3,3-dimethylpiperidin-1-yl)-1,4-dihydro-4-oxo-quinoline-3-carboxylic acid was prepared as per Example No.16 described in our co-pending US Patent applications No. US 20030216568.

The free base S-(−)-1-cyclopropyl-6-fluoro-methoxy-7-(4-amino-3,3-dimethylpiperidin-1-yl)-1,4-dihydro-4-oxo-quinoline-3-carboxylic acid was prepared as per Example No.17 described in our co-pending US Patent applications Nos. 2003/0096812 and 2003/0216568.

The methods of preparation of polymorphs (±) A-3, (±) B-1, (±) B-2, (+) A-3, (+) B-1, (+) B-2, (−) A-3, (−) A-4, (−) B-1 and (−) B-2 are not limited to these methods.

Crystalline Polymorphic form of (±)-1-Cyclopropyl-6-fluoro-1,4-dihydro-8-methoxy-7-(4-amino-3,3-dimethyl-1-piperidinyl)-4-oxo-quinoline-3-carboxylic Acid Hydrochloride-Polymorph A1

(Example 103 of US patent publication 20030216568)

50 gm of (±)-1-cyclopropyl-6-fluoro-1,4-dihydro-8-methoxy-7-(4-amino-3,3-dimethyl-1-piperidinyl)-4-oxo-quinoline-3-carboxylic acid hydrochloride was dissolved in 4.0 liter methanol at reflux temperature. The clear solution was filtered through a celite bed and the resultant solution was concentrated to approximately 1 liter, cooled to a temperature between 25-35° C. and filtered under suction after 12 hours. The solid obtained was further dried at 70° C. under vacuum to provide crystalline material (35.6 gm).

The polymorph was characterized by the following analytical data.

Differential Scanning Calorimetry (DSC):
Endotherm at 252.33° C. (onset at 246.19° C.) exotherm at 205.0 (onset at 200.68° C.) and 259.00° C. (onset at 255.83° C.).

X-ray powder diffraction:
(2θ values): 11.16±0.2, 12.06±0.2, 13.74±0.2, 15.06±0.2, 16.46±0.2, 18.60±0.2, 21.72±0.2, 22.44±0.2, 23.72±0.2, 24.66±0.2, 25.90±0.2, 30.08±0.2, 32.58±0.2.

IR values (cm$^{-1}$): 3442, 2957, 1728, 1623, 1512, 1460, 1318, 1277, 1184, 1056, 938.

Crystalline Polymorphic Form of (±)-1-Cyclopropyl-6-fluoro-1,4-dihydro-8-methoxy-7-(4-amino-3,3-dimethyl-1-piperidinyl)-4-oxo-quinoline-3-carboxylic Acid Hydrochloride-Polymorph A2

(Example 104 of US patent publication 20030216568)

3 gm of (±)-1-cyclopropyl-6-fluoro-1,4-dihydro-8-methoxy-7-(4-amino-3,3-dimethyl-1-piperidinyl)-4-oxo-quinoline-3-carboxylic acid hydrochloride salt was dissolved in 15 ml of water at reflux temperature, allowed to crystallize by cooling to a temperature between 25-35° C. and filtered under suction. The solid obtained was further dried at 70° C. under vacuum to provide crystalline material (2.8 gm).

The polymorph was characterized by the following analytical data.

Differential Scanning Calorimetry (DSC):
Endotherm at 144.66 (onset 115.25) and 254.83° C. (onset at 251.00° C.), exotherm at 211.33 (onset at 208.35° C.) and 259.66° C. (onset at 257.18° C.).

X-ray powder diffraction:
(2θ values): 8.58±0.2, 13.08±0.2, 14.9±0.2, 16.72±0.2, 18.34±0.2, 22.68±0.2, 25.38±0.2, 25.92±0.2, 27.6±0.2, 28.18±0.2.

IR values (cm$^{-1}$): 3476, 3332, 2880, 1712, 1619, 1528, 1448, 1329, 1273, 1234, 1180, 1066, 1035, 989.

Crystalline polymorphic form of (−)-1-Cyclopropyl-6-fluoro-1,4-dihydro-8-methoxy-7-(4amino-3,3-dimethyl-1-piperidinyl)-4-oxo-quinoline-3-carboxylic Acid Hydrochloride-Polymorph A1

(EXAMPLE—105 of US patent application publication 20030216568)

30 gm of (−)-1-cyclopropyl-6fluoro-1,4-dihydro-8-methoxy-7-(4-amino-3,3-dimethyl-1-piperidinyl)-4-oxo-quinoline-3-carboxylic acid hydrochloride was dissolved in 3.0 liter methanol at reflux temperature. The clear solution was filtered through a celite bed and the resultant solution was concentrated to approximately 500 ml, cooled to a temperature between 25-35° C. and filtered under suction. The solid obtained was further dried at 70° C. under vacuum to provide crystalline material (24.0 gm).

The polymorph was characterized by the following analytical data.

Differential Scanning Calorimetry (DSC):
Endotherm at 126.5° C. (onset 93.94° C.) and 252.50° C. (onset at 245.14° C.), exotherm at 202.83 (onset at 200.02° C.) and 257.17° C. (onset at 255.66° C.).

X-ray powder diffraction: Crystalline nature.
(2θ values): 11.30±0.2, 12.06±0.2, 13.64±0.2, 14.4±0.2, 15.16±0.2, 16.48±0.2, 18.52±0.2, 21.48±0.2, 22.72±0.2, 23.94±0.2, 24.76±0.2, 26.42±0.2, 30.24±0.2, 30.60±0.2.

IR values (cm$^{-1}$): 3363, 2957, 1727, 1625, 1512, 1461, 1377, 1323, 1289, 1183, 1056, 942.

Crystalline polymorphic form of (−)-1-Cyclopropyl-6-fluoro-1,4-dihydro-8-methoxy-7-(4-amino-3,3-dimethyl-1-piperidinyl)-4-oxo-quinoline-3-carboxylic Acid Hydrochloride-Polymorph A2

(EXAMPLE 106 of US patent application publication 20030216568)

5 gm of (−)-1-cyclopropyl-6-fluoro-1,4-dihydro-8-methoxy-7-(4-amino-3,3-dimethyl-1-piperidinyl)-4-oxo-quinoline-3-carboxylic acid hydrochloride was dissolved in 10 ml mixture of 50% aqueous iso-propanol at reflux temperature, cooled to a temperature between 25-35° C. and filtered under suction. The solid obtained was further dried at 70° C. under vacuum to provide crystalline material (2.78 gm).

The polymorph characterized by the following analytical data.

Differential Scanning Calorimetry (DSC): Endotherm at 123.5 (onset 101.7) and 201.83° C. (onset at 189.84° C.), 244.83° C. (onset at 230.73° C.) exotherm at 210.5 (onset at 206.6° C.) and 253.17° C. (onset at 249.50° C.).

X-ray powder diffraction (22 values): 6.70±0.2, 7.06±0.2, 7.72±0.2, 8.24±0.2, 12.40±0.2, 13.66±0.2, 14.96±0.2, 18.62±0.2, 19.40±0.2, 23.24±0.2, 24.90±0.2, 27.86±0.2.

Crystalline Polymorphic Form of (+)-1-Cyclopropyl-6-fluoro-1,4-dihydro-8-m-ethoxy-7-(4-amino-3,3-dimethyl-1-piperidinyl)-4-oxo-quinoline-3-carboxylic Acid Hydrochloride-Polymorph A1

(EXAMPLE 107 of US patent application publication 20030216568)

30 gm of (+)-1-cyclopropyl-6-fluoro-1,4-dihydro-8-methoxy-7-(4amino-3,3-dimethyl-1-piperidinyl)-4-oxo-quinoline-3-carboxylic acid hydrochloride was dissolved in 3.0 liter methanol at reflux temperature. The clear solution was filtered through a celite bed and the resultant solution was concentrated to approximately 500 ml, cooled to a temperature between 25-35° C. and filtered under suction. The solid obtained was further dried at 70° C. under vacuum to provide crystalline material (24.0 gm).

The polymorph was characterized by the following analytical data.

Differential Scanning Calorimetry (DSC):

Endotherm at 131.5° C. (onset 92.32° C.) and 253.33° C. (onset at 248.28° C.), exotherm at 204.0° C. (onset at 200.8° C.) and 258.0° C. (onset at 256.83° C.).

X-ray powder diffraction: (22 values): 11.34±0.2, 12.08±0.2, 13.68±0.2, 14.44±0.2, 15.18±0.2, 16.50±0.2, 18.56±0.2, 21.50±0.2, 22.76±0.2, 23.98±0.2, 24.78±0.2, 26.24±0.2, 30.28±0.2, 30.64±0.2, 32.52±0.2.

IR values (cm$^{-1}$): 3653, 3369, 2960, 1727, 1627, 1511, 1465, 1377, 1331, 1279, 1183, 1058, 940.

Crystalline Polymorphic Form of (+)-1-Cyclopropyl-6-fluoro-1,4dihydro-8-methoxy-7-(4-amino-3,3-dimethyl-1-piperidinyl)-4-oxo-quinoline-3-carboxylic Add Hydrochloride-Polymorph A2

(Example 108 of US Patent application publication 20030216568)

5 gm of (+)-1-cyclopropyl-6-fluoro-1,4-dihydro-8-methoxy-7-(4-amino-3,3-dimethyl-1-piperidinyl)-4-oxo-quinoline-3-carboxylic acid hydrochloride was dissolved in 10 ml mixture of 50% aqueous iso-propanol at reflux temperature, cooled to a temperature between 25-35° C. and filtered under suction. The solid obtained was further dried at 70° C. under vacuum to provide crystalline material (3.40 gm).

The polymorph was characterized by the following analytical data.

Differential Scanning Calorimetry (DSC):

Endotherm at 136.66° C. (onset 101.0° C.) and 256.83° C. (onset at 251.92° C.) exotherm at 201.50° C. (onset at 198.60° C.) and 261.16° C. (onset at 259.83° C.). X-ray powder diffraction:

(22 values): 7.00±0.2, 7.66±0.2, 8.00±0.2, 12.32±0.2, 12.72±0.2, 13.58±0.2, 14.88±0.2, 15.36±0.2, 16.08±0.2, 18.38±0.2, 19.36±0.2, 20.58±0.2, 23.18±0.2, 25.40±0.2, 26.72±0.2, 72.82±0.2, 29.80±0.2, 30.60±0.2, 32.28±0.2, 36.94±0.2.

IR values (cm$^{-1}$): 3401, 2845, 2632, 1711, 1621, 1537, 1458, 1378, 1321, 1275, 1207, 1061, 989, 806.

(±)-1-Cyclopropyl-6-fluoro-1,4-dihydro-8-methoxy-7-(4-amino-3,3-dimethy-l-1-piperidinyl)-4-oxo-quinoline-3-carboxylic Acid (EXAMPLE-10 of US patent application publication 20030216568)

4-Benzyloxycarbonylamino-3,3-dimethyl piperidine (100 g, 0.381 mol) was suspended in 200 ml acetonitrile under stirring. To the solution was added (1-cyclopropyl-6,7-difluoro-8-methoxy-1,4-dihydro-4-oxo-quinoline-3-carboxylate O$^3$, O$^4$) difluoroboron chelate (65 g, 0.189 mol) and stirring was started at temperature between 25-35° C. The reaction mixture was stirred for 4-5 hrs at this temperature. After the reaction was completed, the solvent was removed under vacuum to dryness to obtain a solid. To the solid was charged 200 ml ethyl alcohol followed by triethylamine (20 g, 0.198 mol). The reaction mixture was stirred at reflux temperature for 2-3 hrs. The solution was left overnight at 25-35° C. The solid separated in the reaction mixture was filtered and washed with 50 ml ethanol. The filtered solid was stirred with reflux at 100-110° C. in concentrated hydrochloric acid (250 ml) for 2 hr. The resulting solution was taken to dryness by evaporating the acid under vacuum to obtain a residue. To the residue was added 1 L acetone and the suspension stirred for 1 hr. The resulting solid was filtered and washed with acetone. The residue was suspended in 600 ml chloroform and was refluxed for 30 minutes. The suspension was filtered and the residue washed with chloroform. The residue was suspended in methanol (600 ml) and was stirred at 30-35° C. for 30 minutes. The suspension was filtered to obtain a solid, which was dissolved in 1 L water under stirring at 60-70° C. The pH of the solution was adjusted between 8.0-9.0 by adding 30% aqueous sodium hydroxide solution. The reaction mixture was extracted with 600 ml.times.2 chloroform. The organic layers were combined and washed with water, dried over Na$_2$SO$_4$ and evaporated under reduced pressure to afford a solid which was further triturated with methyl alcohol and filtered to give 43 g (56%) titled compound.

m/z (M+1) 404, mp 222-224° C.

NMR (CDCl$_3$): 0.95-1.3 (m, 10H); 1.7-1.8 (m, 2H); 2.6 (t, 1H); 3.0 (dd, 1H); 3.3 (m 2H); 3.6 (m, 1H), (3.7 s, 3H); 4.02 (m, 1H), 7.9 (d, 1H); 8.8 (s, 1H).

An alternate procedure to prepare this compound is by a method similar to that described in Example 1 where 4-amino-3,3-dimethylpiperidine was used in place of 4-amino-3-methylpiperidine.

A second alternate procedure to prepare this compound is by treating 1-cyclopropyl-6-fluoro-1,4-dihydro-8-methoxy-7-(4-1-carbethoxyam-ino-3,3-dimethyl-1-piperidinyl)-4-oxo-quinoline-3-carboxylic acid [obtained from condensation of 1-cyclopropyl-6,7-difluoro-1,4-dihydro-8-m-ethoxy-4-oxo-quinoline-3-carboxylic acid difluoroborane chelate and 4-1-carbethoxyamino-3,3-dimethylpiperidine] (2.0 g, 4.0 mmol) under reflux with aqueous NaOH (0.6M, 100 ml) for 4 hr with stirring, filtered and the residue dried. The obtained crude product was adjusted to pH 3-5 by 3 N HCl, concentrated, triturated with acetone and crystallisation from methanol furnished the required product.

(+)-1-Cyclopropyl-6-fluoro-1,4-dihydro-8-methoxy-
7-(4-amino-3,3-dimethyl-1-piperidinyl)-4-oxo-
quinoline-3-carboxylic Acid (Example 16 of US patent-application publication20030216568)

Grams (19.34 mmol) of (+)-1-cyclopropyl-6-fluoro-1,4-dihydro-8-meth-oxy-7-(4-amino-3,3-dimethyl-1-piperidinyl)-4-oxo-quinoline-3-carboxylic acid hydrochloride were dissolved in 250 ml water under stirring. The solution pH was adjusted between 8.0-9.0 by adding 30% aqueous sodium hydroxide solution. The reaction mixture was extracted with 200 ml.times.2 chloroform. Combined organic layer was washed with water, dried over $Na_2SO_4$ and evaporated under reduced pressure to afford a solid which was further triturated with isopropyl alcohol and filtered to give 7.34 g (94%) above mentioned compound, mp 221-224° C.

NMR ($CDCl_3$): 0.95-1.3 (m, 10H); 1.7-1.8 (m, 2H); 2.6 (t, 1H); 3.0 (dd, 1H); 3.3 (m, 2H); 3.6 (m, 1H), (3.7 s, 3H); 4.02 (m, 1H), 7.9 (d, 1H); 8.8 (s, 1H).

$[\alpha]_D^{25}$ value +133.84° (c=1, chloroform).

(−)-1-Cyclopropyl-6-fluoro-1,4-dihydro8-methoxy-
7-(4-amino-3,3-dimethyl-1-piperidinyl)-4-oxo-
quinoline-3-carboxylic Acid (Example 17 of US patent application publication 20030216568).

Similarly, by using the procedure mentioned above, 8.40 g (19.11 mmol) of (−)-1-cyclopropyl-6-fluoro-1,4-dihydro-8-methoxy-7-(4-amino-3,3-dimethyl-1-piperidinyl)-4-oxo-quinoline-3-carboxylic acid hydrochloride was converted to 6.65 g (86%) titled compound. mp 222-225° C., $[\alpha]_D^{25}$ value 125.06° (c=1, chloroform).

EXAMPLE 1

Polymorphic form A-3 of (±)-1-cyclopropyl-6-
fluoro-8-methoxy-7-(4-amino-3,3-dimethylpiperi-
din-1-yl)-1,4-dihydro-4-oxo-quinoline-3-carboxylic
acid hydrochloride from Polymorphic form A-1

The polymorphic A-1 form of (±)-1-cyclopropyl-6-fluoro-8-methoxy-7-(4-amino-3,3-dimethylpiperidin-1-yl)-1,4-dihydro-4-oxo-quinoline-3-carboxylic acid hydrochloride (3 gm) was kept at a temperature between 130 to 135° C. for 3-4 hours to provide a form A-3 in quantitative yield.

Analysis: FIGS. 7, 17 and 27

Powder X-ray diffraction (2θ): 5.32±0.2°, 5.68±0.2°, 9.42±0.2°, 10.06±0.2°, 10.40±0.2°, 11.40±0.2°, 11.78±0.2°, 12.98±0.2°, 13.74±0.2°, 14.38±0.2°, 14.66±0.2°, 16.02±0.2°, 22.52±0.2°, 23.74±0.2°, 24.48±0.2°, 25.22±0.2°, 27.36±0.2°, 28.74±0.2°, 31.28±0.2°;

DSC: endotherm at 252.50° C. (onset at 243.43° C.);

Infra-red spectrum selected peaks ($cm^{-1}$): 3442, 2951, 2609, 1729, 1617, 1515, 1452, 1320, 1179, 952, 883.

EXAMPLE 2

Polymorphic form A-3 of (±)-1-cyclopropyl-4-
fluoro-8-methoxy-7-(4-amino-3,3-dimethylpiperi-
din-1-yl)-1,4-dihydro-4-oxo-quinoline-3-carboxylic
acid hydrochloride from Polymorphic form A-2

The polymorphic A-2 form of (±)-1-cyclopropyl-6-fluoro-8-methoxy-7-(4-amino-3,3-dimethylpiperidin-1-yl)-1,4-dihydro-4-oxo-quinoline-3-carboxylic acid hydrochloride (3 gm) was kept at a temperature between 130 to 135° C. for 3-4 hours to provide a form A-3 in quantitative yield having analytical data described in Example 1.

EXAMPLE 3

Polymorphic Form A-2 of (±)-1-cyclopropyl-6-
fluoro-8-methoxy-7-(4-amino-3,3-dimethylpiperi-
din-1-yl)-1,4-dihydro-4oxo-quinoline-3-carboxylic
acid hydrochloride from Polymorphic Form A-3

A suspension of A-3 form of (+)-1-cyclopropyl-6-fluoro-8-methoxy-7-(4-amino-3,3-dimethylpiperidin-1-yl)-1,4-dihydro-4-oxo-quinoline-3-carboxylic acid hydrochloride (2.0 gm) in water (6 ml) was stirred at 25-35° C. for 3 hours. Isopropanol (24 ml) was added to the suspension. The reaction mixture was stirred further for 12 hours and the crystals of the titled product isolated by filtration and dried under vacuum at a temperature between 60 to 70° C. Yield 1.9 gms, 95% having analytical data as described in Example 104 of our co-pending US application No. US 20030216568.

EXAMPLE 4

Polymorphic form A-3 of R-(+)-1-cyclopropyl-6-
fluoro-8-methoxy-7-(4-amino-3,3-dimethylpiperi-
din-1-yl)-1,4-dihydro-4-oxo-quinoline-3-carboxylic
acid hydrochloride from Polymorphic form A-1

The polymorphic A-1 form of R-(+)-1-cyclopropyl-6-fluoro-8-methoxy-7-(4-amino-3,3-dimethylpiperidin-1-yl)-1,4-dihydro-4-oxo-quinoline-3-carboxylic acid hydrochloride (3 gm) was kept at a temperature between 130 to 135° C. for 3-4 hours to provide a form A-3 in quantitative yield.

Analysis: FIGS. 8, 18 and 28

Powder X-ray diffraction (2θ): 5.34±0.2°, 5.70±0.2°, 9.46±0.2°, 10.08±0.2°, 10.44±0.20°, 11.42±0.2°, 11.82±0.2°, 12.86±0.2°, 13.62±0.2°, 14.26±0.2°, 14.72±0.2°, 16.08±0.2°, 22.16±0.2°, 23.68±0.2°, 24.18±0.2°, 24.86±0.2°, 25.98±0.2°, 27.04±0.2°, 28.84±0.2°, 31.56±0.2°, 31.84±0.2°;

DSC: endotherm at 251.16° C. (onset at 241.05° C.);

Infra-fed spectrum ($cm^{-1}$): 3430, 2805, 1029, 1728, 1617, 1515, 1452, 1180, 1051, 951.

EXAMPLE 5

Polymorphic Form A-3 of R-(+)-1-cyclopropyl-6-
fluoro-8-methoxy-7-(4-amino-3,3-dimethylpiperi-
din-1-yl)-1,4-dihydro-4-oxo-quinoline-3-carboxylic
acid hydrochloride from Polymorphic Form A-2

The polymorphic A-2 form of R-(+)-1-cyclopropyl-6-fluoro-8-methoxy-7-(4-amino-3,3-dimethylpiperidin-1-yl)-1,4-dihydro4-oxo-quinoline-3-carboxylic acid hydrochloride (1.0 gm) was kept at a temperature between 130 to 135° C. for 3-4 hours to provide a form A-4 in quantitative yield having analytical data described in Example 4.

EXAMPLE 6

Polymorphic Form A-2 of R-(+)-1-cyclopropyl-6-fluoro-8-methoxy-7-(4-amino-3,3-dimethylpiperidin-1-yl)-1,4-dihydro-4-oxo-quinoline-3-carboxylic acid hydrochloride from Polymorphic Form A-3

A suspension of polymorph A-3 form of R-(+)-1-cyclopropyl-6-fluoro-8-methoxy-7-(4-amino-3,3-dimethylpiperidin-1-yl)-1,4-dihydro-4-oxo-quinoline-3-carboxylic acid hydrochloride (2.0 gm) in water (6.0 ml) was heated under stirring at a temperature between 90-100° C. to provide a dear solution. The clear solution was allowed to cool and isopropanol (24.0 ml) was added. The resulting suspension was stirred at a temperature between 25-35° C. for 1 hour and the crystals of the titled product isolated by filtration and dried under vacuum at a temperature between 60 to 70° C. Yield 1.9 gm, 95% having analytical data as described in Example 108 of our co-pending US application No. US 20030216568.

EXAMPLE 7

Polymorphic Form A-3 of S-(−)-1-cyclopropyl-6-fluoro-8-methoxy-7-(4-amino-3,3-dimethylpiperidin-1-yl)-1,4-dihydro-4-oxo-quinoline-3carboxylic acid hydrochloride from Polymorphic Form A-1

Method-A

A suspension of A-1 form of S-(−)-1-cyclopropyl-6-fluoro-8-methoxy-7-(4-amino-3,3-dimethylpiperidin-1-yl)-1,4-dihydro-4-oxo-quinoline-3-carboxylic acid hydrochloride (150 gm) in water (450 ml) was stirred at 25-35° C. for 3 hours. Isopropanol (2.5 ltr) was added to the suspension. The reaction mixture was stirred further for 12 hours and the crystals of the titled product isolated by filtration and dried under vacuum at a temperature between 60 to 70° C.

Yield 120 gms, 80%.

The product is characterized by the X-ray diffraction pattern described above.

Analysis: FIGS. 9, 19 and 29.

Powder X-ray diffraction (2θ): 7.04±0.2°, 7.70±0.2°, 8.06±0.2°, 12.34±0.2°, 12.78±0.2°, 13.64±0.2°, 15.40±0.2°, 16.14±0.2°, 18.62±0.2°, 19.40±0.2°, 20.64±0.2°, 21.84±0.2°, 23.22±0.2°, 26.80±0.2°, 27.88±0.2°, 29.86±0.2°, 32.30±0.2°, 33.36±0.2°, 37.02±0.2°, 39.24±0.2°;

DSC: endotherm at 131.66° C. (onset at 95.32° C.) exotherm at 202.16° C. (onset at 198.36° C.), endotherm at 257.33° C. (onset at 252.35° C.));

Infra-red spectrum selected peaks (cm$^{-4}$): 3396, 1715, 1621, 1530, 1451, 1274.

Method-B

Polymorph A-1 of S-(−)-1-cyclopropyl-6-fluoro-8-methoxy-7-(4-amino-3,3-dimethylpiperidin-1-yl)-1,4-dihydro4-oxo-quinoline-3-carboxylic acid hydrochloride (100 mg) was dissolved in 0.9% aqueous solution of sodium chloride (10 ml) to obtain a clear solution, which was allowed to stand at 3-5° C. Crystals of the titled product which separated from the solution were isolated by filtration and dried under vacuum at a temperature between 60 to 70° C. Yield 76 mg, 76%. The product is characterized as polymorph A-3 according to the analytical data as shown for the product obtained under Method-A.

EXAMPLE 8

Polymorphic Form A-3 of S-(−)-1-cyclopropyl-6-fluoro-8-methoxy-7-(4-amino-3,3-dimethylpiperidin-1-yl)1,4-dihydro-4-oxo-quinoline-3-carboxylic acid hydrochloride from Polymorphic Form A-2

A suspension of polymorph A-2 form of S-(−)-1-cyclopropyl-6-fluoro-8-methoxy-7-(4-amino-3,3-dimethylpiperidin-1-yl)-1,4-dihydro-4-oxo-quinoline-3-carboxylic acid hydrochloride (1 gm) in water (3 ml) was heated under stirring at a temperature between 90-100° C. to provide a clear solution. The clear solution was allowed to cool and isopropanol (20 ml) was added. The resulting suspension was stirred at a temperature between 25-35° C. for 1 hour and the crystals of the titled product isolated by filtration and dried under vacuum at a temperature between 60 to 70° C. Yield 0.78 gm, 78% having analytical data as described in Example 7.

EXAMPLE 9

Polymorphic Form A-3 of S-(−)-1-cyclopropyl-6-fluoro-8-methoxy-7-(4-amino-3,3-dimethylpiperidin-1-yl)-1,4-dihydro-4-oxo-quinoline-3-carboxylic acid hydrochloride from Polymorphic Form A-4

A suspension of polymorphic A4 form of S-(−)-1-cyclopropyl-6-fluoro-8-methoxy-7-(4-amino-3,3-dimethylpiperidin-1-yl)-1,4-dihydro-4-oxo-quinoline-3-carboxylic acid hydrochloride (1.5 gm) in water (5 ml) was heated under stirring at a temperature between 90-100° C. to provide a clear solution. The clear solution was allowed to cool to 25-35° C. and isopropanol (50 ml) was added. The resulting suspension was stirred for 1 hour and the crystals of the titled product isolated by filtration and dried under vacuum at a temperature between 60 to 70° C. Yield 1.21 gm, 81% having analytical data as described in Example 7.

EXAMPLE 10

Polymorphic Form A-4 of S-(−)-1-cyclopropyl-6-fluoro-8-methoxy-7-(4-amino-3,3-dimethylpiperidin-1-yl)-1,4-dihydro-4-oxo-quinoline-3-carboxylic acid hydrochloride from Polymorphic Form A-1

The polymorphic A-1 form of S-(−)-1-cyclopropyl-6-fluoro-8-methoxy-7-(4-amino-3,3-dimethylpiperidin-1-yl)-1,4-dihydro4-oxo-quinoline-3-carboxylic acid hydrochloride (7.5gm) was kept at a temperature between 130 to 135° C. for 3-4 hours to provide a form A-4 in quantitative yield.

The product is characterized by the X-ray diffraction pattern described below.

Analysis: FIGS. 10, 20 and 30;

Powder X-ray diffraction (2θ): 5.34±0.2°, 5.68±0.2°, 9.48±0.2°, 10.08±0.2°, 10.44±0.2°, 11.42±0.2°, 11.84±0.2°, 12.86±0.2°, 13.62±0.2°, 14.24±0.2°, 14.74±0.2°, 16.08±0.2°, 22.16±0.2°, 24.14±0.2°, 24.82±0.2°, 25.94±0.2°, 27.02±0.2°, 28.84±0.2°, 31.82±0.2°;

DSC: endotherm at 254.33° C. (onset at 248.00° C.);

Infra-red spectrum (cm$^{-1}$): 2895, 1729, 1618, 1516, 1452, 1379, 1321, 1179, 1108, 1050, 951, 882, 808, 734.

EXAMPLE 11

Polymorphic Form A-4 of S-(−)-1-cyclopropyl-6-fluoro-8-methoxy-7-(4-amino-3,3-dimethylpiperidin-1-yl)-1,4-dihydro-4-oxo-quinoline-3-carboxylic acid hydrochloride from Polymorphic Form A-2

The polymorphic A-2 form of S-(−)-1-cyclopropyl-6-fluoro-8-methoxy-7-(4-amino-3,3-dimethylpiperidin-1-yl)-1,4-dihydro-4-oxo-quinoline-3-carboxylic acid hydrochloride (5 gm) was kept at a temperature between 130 to 135° C. for 3-4 hours to provide a form A-4 in quantitative yield having analytical data described in Example 10.

EXAMPLE 12

Polymorphic Form A-4 of S-(−)-1-cyclopropyl-6-fluoro-8-methoxy-7-(4-amino-3,3-dimethylpiperidin-1-yl)-1,4-dihydro-4-oxo-quinoline-3-carboxylic acid hydrochloride from Polymorphic Form A-3

The polymorphic A-3 form of S-(−)-1-cyclopropyl-6-fluoro-8-methoxy-7-(4-amino-3,3-dimethylpiperidin-1-yl)-1,4-dihydro-4-oxo-quinoline-3-carboxylic acid hydrochloride (5 gm) was kept at a temperature between 130 to 135° C. for 3-4 hours to provide a form A-4 in quantitative yield having analytical data described in Example 10.

EXAMPLE 13

Polymorphic form B-1 of (±)-1-cyclopropyl-6-fluoro-8-methoxy-7-(4-amino-3,3-dimethylpiperidin-1-yl)-1,4-dihydro-4-oxo-quinoline-3-carboxylic acid mesylate A suspension of (±)-1-cyclopropyl-6-fluoro-8-methoxy-7-(4-amino-3,3-dimethylpiperidin-1-yl)-1,4-dihydro-4-oxo-quinoline-3-carboxylic acid (8.0 gms, 19.8 mmol) in isopropanol (40 ml) was heated to reflux at 75-80° C. under stirring. Methane sulfonic acid (1.41 ml, 21.80 mmol) in 10 ml isopropyl alcohol was added to the suspension. The reaction mixture was stirred at a temperature between 75-80° C. for 1 hour. The suspension was cooled to a temperature between 25-35° C. and the crystals of the titled product isolated by filtration and dried under vacuum at a temperature between 60 to 70° C. Yield 8.5 gms, 86%.

Figure 11:
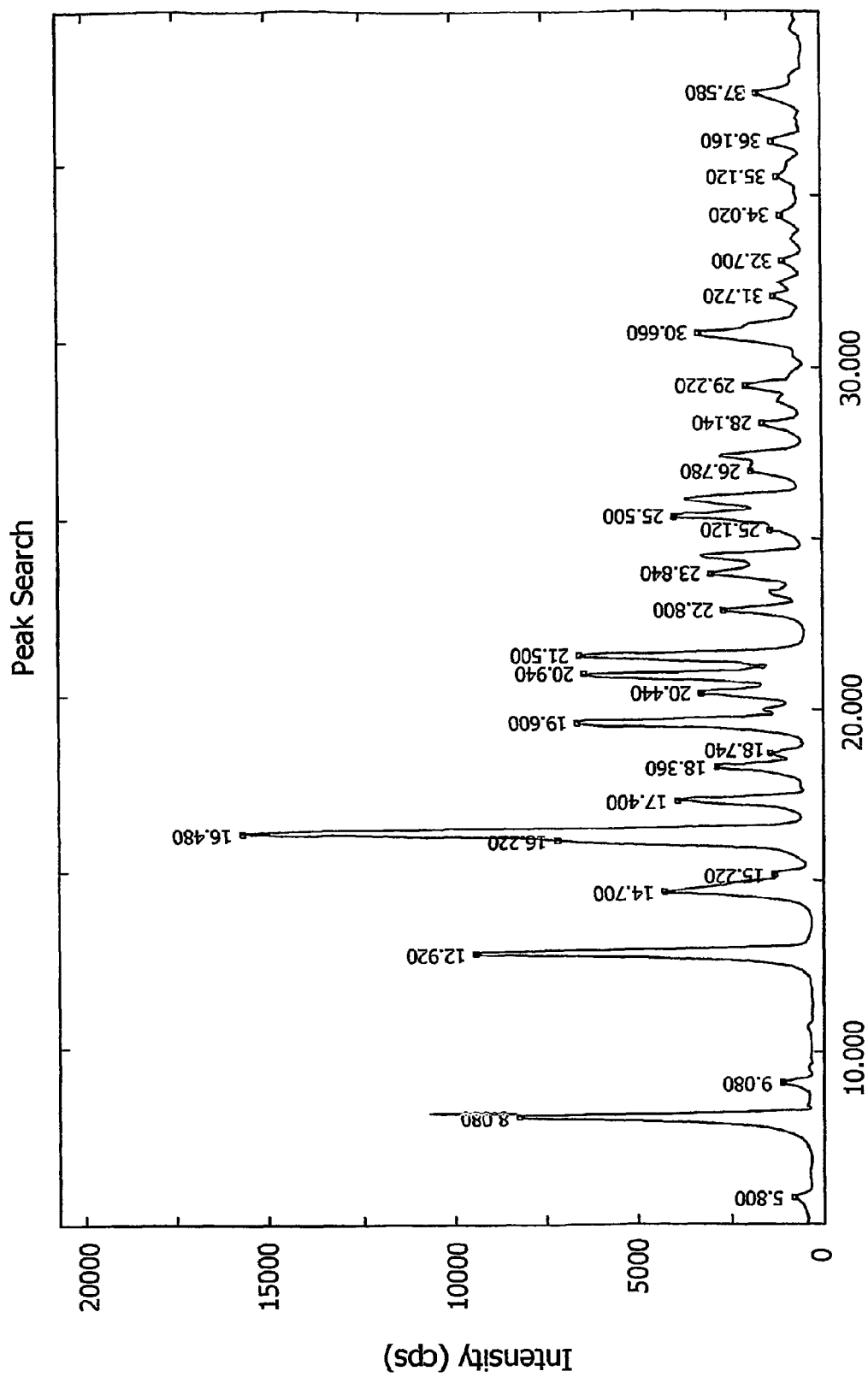
FIG. 11 represents the Powder X-ray diffraction (XRPD) spectrum of the crystalline B-1 form of (+)-1-cyclopropyl-6-fluoro-8-methoxy-7-(4-amino-3,3-dimethylpiperidin-1-yl) 1,4-dihydro-4-oxo-quinoline-3-carboxylic acid mesylate of the invention.
Figure 21:
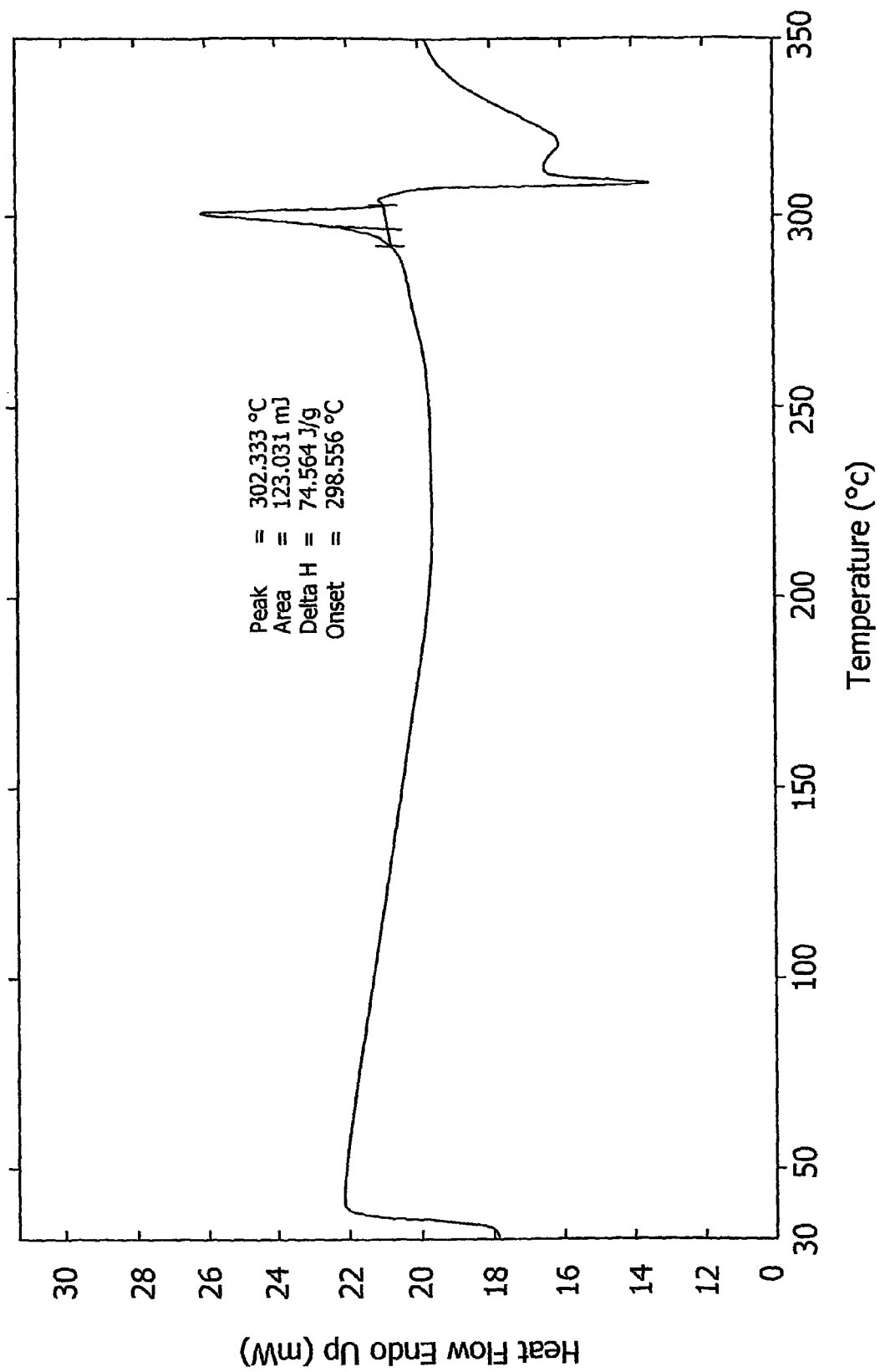
FIG. 21 represents the Differential Scanning Calorimetric (DSC) thermogram of the crystalline B-1 form of (±)-1-cyclopropyl-6-fluoro-8-methoxy-7-(4-amino-3,3-dimethylpiperidin-1-yl)-1,4-dihydro-4-oxo-quinoline-3-carboxylic acid mesylate of the invention.
Figure 31:
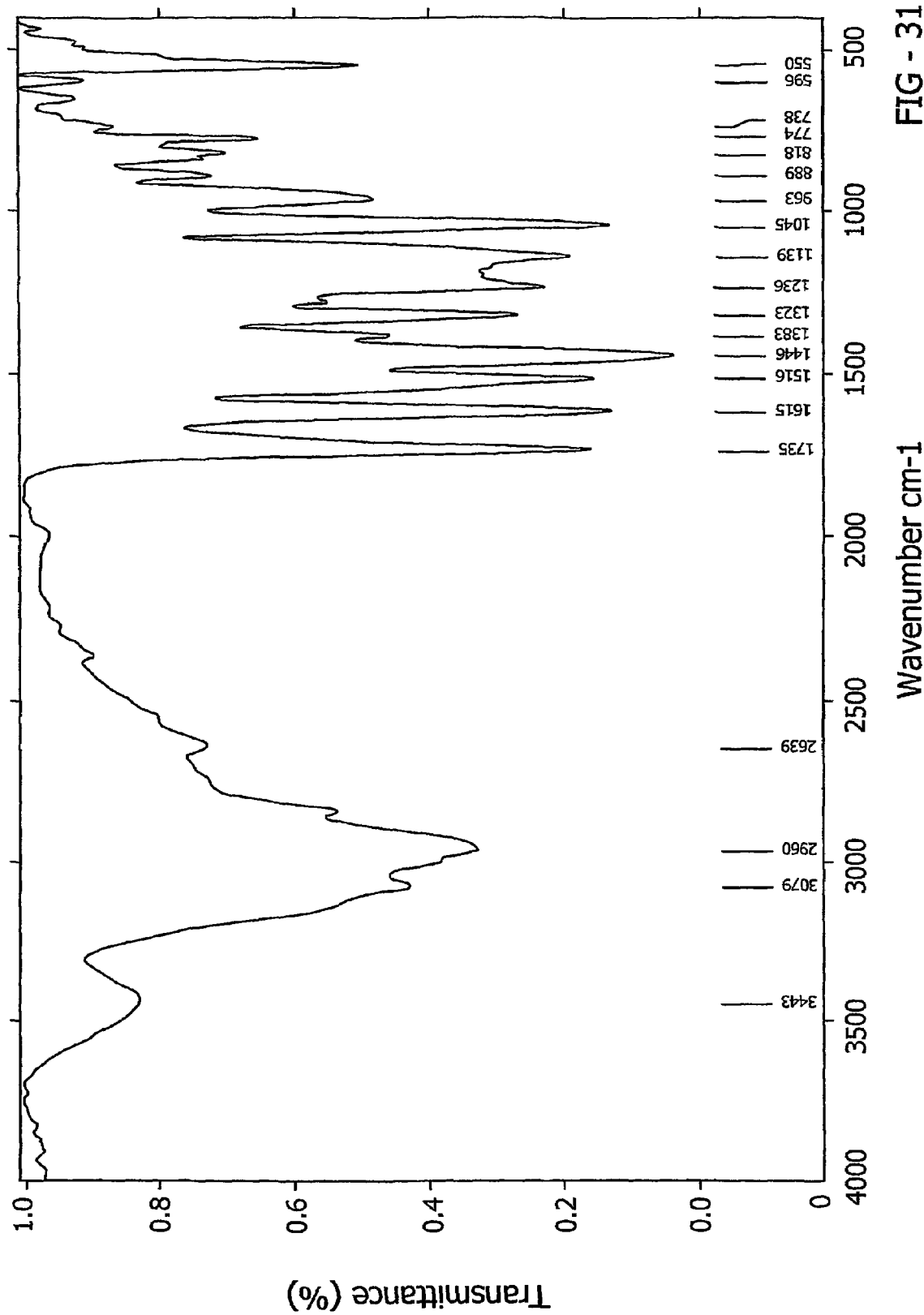
FIG. 31 represents the Infra-red (IR) spectrum of the crystalline B-1 form of (±)-1-cyclopropyl-6-fluoro-8-methoxy-7-(4-amino-3,3-dimethylpiperidin-1-yl)-1,4dihydro-4-oxo-quinoline-3-carboxylic acid mesylate of the invention.

Analysis: FIGS. 11, 21 and 31

Powder X-ray diffraction (2θ): 5.80±0.2°, 8.08±0.2°, 9.08±0.2°, 12.92±0.2°, 14.70±0.2°, 16.48±0.2°, 17.40±0.2°, 18.36±0.2°, 18.74±0.2°, 19.60±0.2°, 20.44±0.2°, 20.94±0.2°, 21.50±0.2°, 22.80±0.2°, 23.28±0.2°, 23.84±0.2°, 24.36±0.2°, 25.50±0.2°, 26.00±0.2°, 26.78±0.2°, 27.24±0.2°, 29.22±0.2°, 30.66±0.2°, 37.58±0.2°.

DSC: endotherm at 302.33° C. (onset at 298.55° C.);

Infra-red spectrum ($cm^{-1}$): 3443, 3079, 2960, 1735, 1615, 1516, 1446, 1383, 1323, 1236, 1139, 1045.

EXAMPLE 14

Polymorphic form B-1 of R-(+)-1-cyclopropyl-6-fluoro-8-methoxy-7-(4-amino-3,3-dimethylpiperidin-1-yl)-1,4-dihydro-4-oxo-quinoline-3-carboxylic acid mesylate By using procedure described in Example-13 and using R-(+)-1-cyclopropyl-6-fluoro-8-methoxy-7-(4-amino-3,3-dimethylpiperidin-1-yl)-1,4-dihydro-4-oxoquinoline-3-carboxylic acid the title polymorph was obtained in 86% yield.

Analysis: FIGS. 12, 22 and 32

Powder X-ray diffraction (2θ): 5.74±0.2°, 8.02±0.2°, 9.02±0.2°, 12.84±0.2°, 14.74±0.2°, 16.46±0.2°, 17.32±0.2°, 18.38±0.2°, 19.58±0.2°, 20.38±0.2°, 20.92±0.2°, 21.48±0.2°, 22.80±0.2°, 23.80±0.2°, 24.28±0.2°, 25.62±0.2°, 26.88±0.2°, 27.32±0.2°, 28.20±0.2°, 29.16±0.2°, 30.68±0.2°.

DSC: endotherm at 299.83° C. (onset at 295.27° C.);

Infra-red spectrum ($cm^{-1}$): 3442, 2958, 2625, 1735, 1616, 1516, 1446, 1323, 1236, 1140, 1045, 961, 550.

EXAMPLE 15

Polymorphic Form B-1 of S-(−)-1-cyclopropyl-6-fluoro-8-methoxy-7-(4-amino-3,3-dimethylpiperidin-1-yl)-1,4-dihydro-4-oxo-quinoline-3-carboxylic acid mesylate A suspension of S-(−)-1-cyclopropyl-6-fluoro-8-methoxy-7-(4-amino-3,3-dimethylpiperidin-1-yl)-1,4-dihydro-4-oxo-quinoline-3-arboxylic acid (12 gms, 29.77 mmol) in isopropanol (150 ml) was heated to reflux at 75-80° C. under stirring. Methane sulfonic acid (3.2 gms, 32.74 mmol) was added to the suspension. The reaction mixture was stirred at a temperature between 75-80° C. for 1 hour. The suspension was cooled to a temperature between 25-35° C. and the crystals of the titled product isolated by filtration and dried under vacuum at a temperature between 60 to 70° C. Yield 14 gms, 94%.

The product is characterized by the X-ray diffraction pattern described below.

Analysis: FIGS. 13, 23 and 33.

Powder X-ray diffraction (2θ): 8.02±0.2°, 12.84±0.2°, 14.70±0.2°, 16.44±0.2°, 17.30±0.2°, 19.56±0.2°, 20.90±0.2°, 21.46±0.2°, 23.76±0.2°, 25.56±0.2°, 27.30±0.2°, 30.66±0.2°, 37.46±0.2°;

DSC: endotherm at 301.00° C. (onset at 297.58° C.).

Infra-red spectrum ($cm^{-1}$): 3441, 2956, 1735, 1617, 1517, 1447, 1321, 1231, 1141, 1043, 886, 821, 776.

EXAMPLE 16

Polymorphic Form B2 of (±)-1-cyclopropyl-6-fluoro-8-methoxy-7-(4-amino-3,3-dimethylpiperidin-1-yl)-1,4-dihydro-4-oxo-quinoline-3-carboxylic acid mesylate from Polymorphic Form B-1

Crystalline form B-1 of (±)-1-cyclopropyl-6-fluoro-8-methoxy-7-(4-amino-3,3-dimethylpiperidin-1-yl)-1,4-dihydro-4-oxo-quinoline-3-carboxylic acid mesylate (2.0 gms, 4.0 mmol) was stirred in 6 ml water at a temperature between 80-100° C. under stirring to give a clear solution. The clear solution was cooled to 25-35° C. to provide a thick suspension. The thick suspension was stirred for 1 hour after adding 24 ml isopropanol at a temperature between 25-35° C. and the crystals of the titled product isolated by filtration and dried under vacuum at a temperature between 60 to 70° C. Yield 1.2 gms, 60%.

Figure 34:
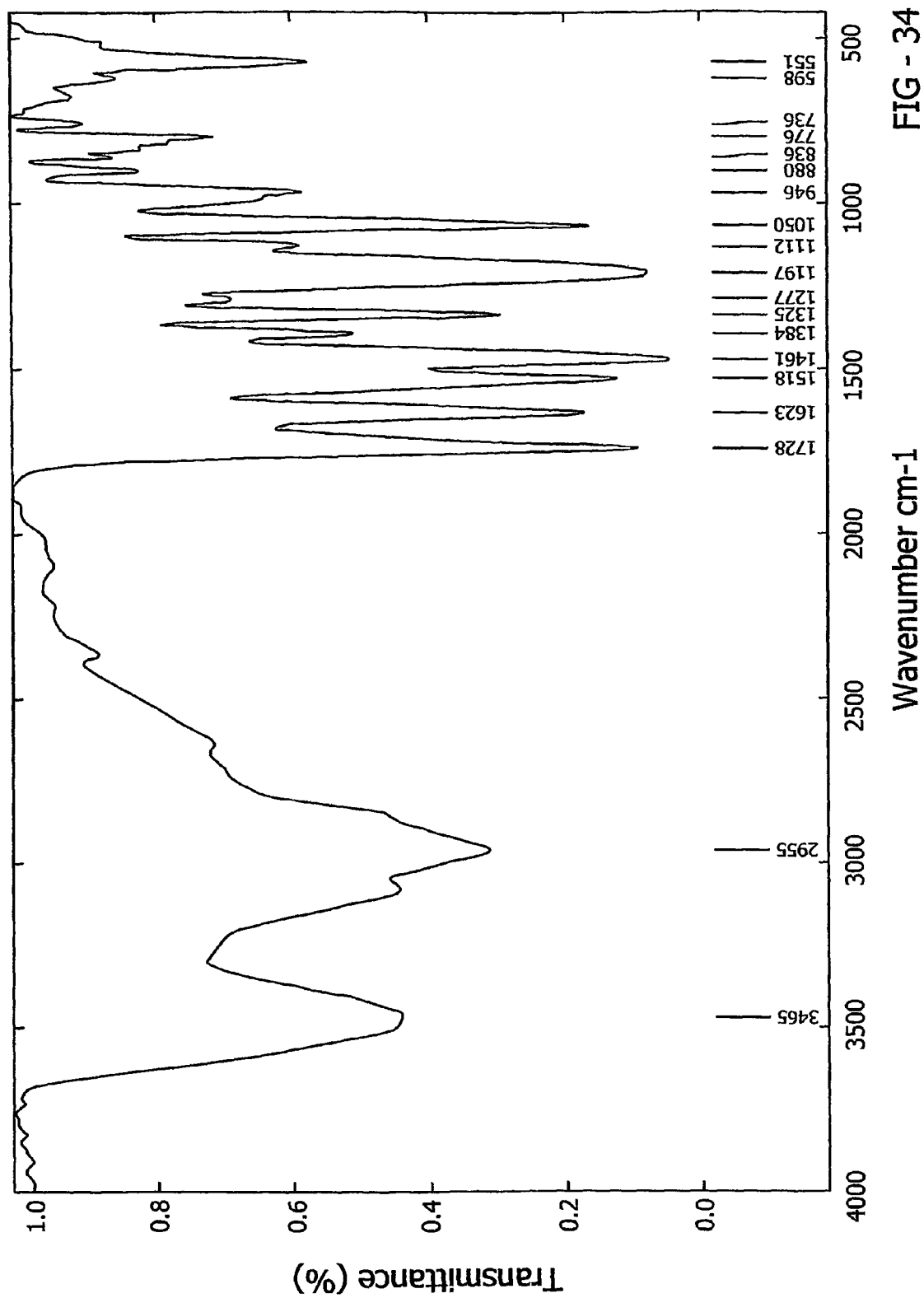
FIG. 34 represents the Infra-red (IR) spectrum of the crystalline B-2 form of (±)-1-cyclopropyl-6-fluoro-8-methoxy-7-(4-amino-3,3-dimethylpiperidin-1-yl)-1,4-dihydro4-oxo-quinoline-3-carboxylic acid methane sulfonate of the invention.

Analysis: FIGS. 14, 24 and 34

Powder X-ray diffraction (2θ): 9.40±0.2°, 9.94, 10.74±0.2°, 12.39±0.2°, 12.98±0.2°, 14.02±0.2°, 15.72±0.2°, 16.92±0.2°, 18.84±0.2°, 19.38±0.2°, 20.52±0.2°, 21.20±0.2°, 22.80, 22.96±0.2°, 24.64±0.2°, 25.54±0.2°, 28.38±0.2°, 29.92±0.2°, 30.79±0.2°, 35.92, 37.88±0.2°;

DSC: endotherm at 98.50° C. (onset at 74.41° C.), endotherm at 303.16° C. (onset at 298.849° C.);

Infra-red spectrum (cm$^{-1}$): 3465, 2955, 1728, 1623, 1518, 1461, 1384, 1325, 1277, 1197, 1112, 1050.

EXAMPLE 17

Polymorphic Form B-2 of R-(+)-1-cyclopropyl-6-fluoro-8-methoxy-7-(4-amino-3,3-dimethylpiperidin-1-yl)-1,4-dihydro-4-oxo-quinoline-3-carboxylic acid mesylate By using procedure described in Example-16 and using R-(+)-1-cyclopropyl-6-fluoro-8-methoxy-7-(4-amino-3,3-dimethylpiperidin-1-yl)-1,4-dihydro-4-oxo-quinoline-3-carboxylic acid the title polymorph was obtained in 56% yield.

Analysis: FIGS. 15, 25 and 35

X-ray powder diffractogram (2θ): 8.04±0.2°, 9.36±0.2°, 10.06±0.2°, 10.84±0.2°, 12.24±0.2°, 12.88±0.2°, 13.94±0.2°, 15.26±0.2°, 15.76±0.2°, 16.82±0.2°, 17.16±0.2°, 18.78±0.2°, 19.62±0.2°, 20.42±0.2°, 21.22±0.2°, 22.30±0.2°, 23.16±0.2°, 24.26±0.2+, 24.62±0.2°, 25.54±0.2°, 28.38±0.2°, 30.00±0.2°, 30.84±0.2°, 38.18±0.2°;

DSC: endotherm at 306.83° C. (onset at 303.39° C.);

Infrared spectrum (cm$^{-1}$): 3084, 2949, 1730, 1626, 1520, 1464, 1383, 1325, 1180, 1048, 949, 599.

EXAMPLE 18

Polymorphic Form B-2 of S-(−)-1-cyclopropyl-6-fluoro-8-methoxy-7-(4-amino-3,3-dimethylpiperidin-1-yl)-1,4-dihydro-4-oxo-quinoline-3-carboxylic acid mesylate from Polymorphic Form B-1

Crystalline form B-1 of S-(−)-1-cyclopropyl-6-fluoro-8-methoxy-7-(4-amino-3,3-dimethylpiperidin-1-yl)-1,4-dihydro-4-oxo-quinoline-3-carboxylic acid mesylate (2.0 gms, 4.04 mmol) was stirred in 3 ml water at a temperature between 80-100° C. under stirring to give a clear solution. The clear solution was cooled to 25-35° C. to provide a thick suspension. The thick suspension was stirred for 1 hour after adding 30 ml isopropanol at a temperature between 25-35° C. and the crystals of the titled product isolated by filtration and dried under vacuum at a temperature between 60 to 70° C. Yield 1.7 gms, 85%.

The product is characterized by the X-ray diffraction pattern described below.

Analysis: FIGS. 16, 26 and 36.

Powder X-ray diffraction (2θ): 9.38±0.2°, 10.04±0.2°, 12.28±0.2°, 12.94±0.2°, 13.98±0.2°, 15.78±0.2°, 16.86±0.2°, 18.80±0.2°, 19.62±0.2°, 21.24±0.2°, 22.32±0.2°, 23.18±0.2°, 24.64±0.2°, 25.56±0.2°, 28.44±0.2°, 30.02±0.2°, 30.90±0.2°, 39.74±0.2°;

DSC: exotherm at 83.83° C. (onset at 58.11° C.), endotherm at 305.50° C. (onset at 301.48° C.);

Infra-red spectrum (cm$^{-1}$): 3486, 1728, 1624, 1521, 1460, 1325, 1191, 1047, 879, 781.

Biological Activity

The MIC (μg/ml) of compounds of the invention against various organisms is determined in accordance with standard NCCLS protocol. In-vitro antimicrobial activity against Fluoroquinolone sensitive strains such as MSSA ATCC 25923, *S. pneumoniae* ATCC 49619, *S. sanguis* ATCC 10556, *E. faecalis* ATCC 29212 and *E. coli* ATCC 25922 is in the range of 0.05-0.20 μg/ml.

The MIC (μg/ml) of compounds of the invention against fluoroquinolone-resistant strains such as MRSA 032, FQ$^R$ *S. pneumoniae* 718, Cipro$^R$ *S. sanguis* 941, Cipro$^R$ *S. mitis* 938 is in the range of 0.2-1.56 μg/ml.

We claim:

1. A polymorph of racemic (±)-1-cyclopropyl-6-fluoro-8-methoxy-7-(4-amino-3,3-dimethylpiperidin-1-yl)-1,4-dihydro-4-oxo-quinoline-3-carboxylic acid hydrochloride, R-(+)-1-cyclopropyl-6-fluoro-8-methoxy-7-(4-amino-3,3-dimethylpiperidin-1-yl)-1,4-dihydro-4-oxo-quinoline-3-carboxylic acid hydrochloride, S-(−)-1-cyclopropyl-6-fluoro-8-methoxy-7-(4-amino-3,3-dimethylpiperidin-1-yl)-1,4-dihydro-4-oxo-quinoline-3-carboxylic acid hydrochloride and racemic (±)-1-cyclopropyl-6-fluoro-8-methoxy-7-(4-amino-3,3-dimethylpiperidin-1-yl)-1,4-dihydro-4-oxo-quinoline-3-carboxylic acid mesylate, R-(+)-1-cyclopropyl-6-fluoro-8-methoxy-7-(4-amino-3,3-dimethylpiperidin-1-yl)1,4-dihydro-4-oxo-quinoline-3-carboxylic acid mesylate, S-(−)-1-cyclopropyl-6-fluoro-8-methoxy-7-(4-amino-3,3-dimethylpiperidin-1-yl)-1,4-dihydro-4-oxo-quinoline-3-carboxylic acid mesylate having the formula I and II respectively

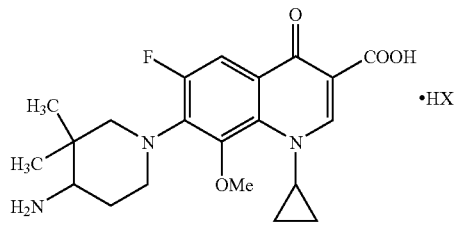

Formula I HX = HCl
Formula II HX = CH$_3$SO$_3$H wherein said polymorph is selected from the group comprising a) a racemic (±)-1-cyclopropyl-6-fluoro-8-methoxy-7-(4-amino-3,3-dimethylpiperidin-1-yl)-1,4-dihydro-4-oxo-quinoline-3-carboxylic acid hydrochloride polymorph A-3 exhibiting the following X-ray diffraction pattern (2θ): 5.32±0.2°, 5.68±0.2°, 9.49±0.2°, 10.06±0.2°, 10.40±0.2°, 11.40±0.2°, 11.78±0.2°, 12.98±0.2°, 13.74±0.2°, 14.38±0.2°, 14.66±0.2°, 16.02±0.2°, 22.52±0.2°, 23.74±0.2°, 24.48±0.2°, 25.92±0.2°, 27.36±0.2°, 28.74±0.2°, 31.28±0.2°, 31.72±0.2°;

b) a R-(+)-1-cyclopropyl-6-fluoro-8-methoxy-7-(4-amino-3,3-dimethylpiperidin-1-yl)-1,4-dihydro-4-oxo-quinoline-3-carboxylic acid hydrochloride polymorph A-3 exhibiting the following X-ray diffraction pattern (2θ): 5.34±0.2°, 5.70±0.2°, 9.46±0.2°, 10.08±0.2°, 10.44±0.2°, 11.42±0.2°, 11.82±0.2°, 12.86±0.2°, 13.62±0.2°, 14.26±0.2°, 14.72±0.2°, 16.08±0.2°, 22.16±0.2°, 23.68±0.2°, 24.18±0.2°, 24.86±0.2°, 25.98±0.2°, 27.04±0.2°, 28.84±0.2°, 31.56±0.2°, 31.84±0.2°;

c) a S-(−)-1-cyclopropyl-6-fluoro-8-methoxy-7-(4-amino-3,3-dimethylpiperidin-1-yl)-1,4-dihydro-4-oxo-quinoline-3-carboxylic acid hydrochloride polymorph A-3 exhibiting the following X-ray diffraction pattern (2θ): 7.04±0.2°, 7.70±0.2°, 8.06±0.2°, 12.34±0.2°, 12.78±0.2°, 13.64±0.2°, 15.40±0.2°, 16.14±0.2°, 18.69±0.2°, 19.40±0.2°, 20.64±0.2°, 21.84±0.2°, 23.22±0.2°, 26.80±0.2°, 27.88±0.2°, 29.86±0.2°, 32.30±0.2°, 33.36±0.2°, 37.02±0.2°, 39.24±0.2°;

d) a S-(−)-1-cyclopropyl-6-fluoro-8-methoxy-7-(4-amino-3,3-dimethylpiperidin-1-yl)-1,4-dihydro-4-oxo-quinoline-3-carboxylic acid hydrochloride polymorph A-4 exhibiting the following X-ray diffraction pattern
(2θ): 5.34±0.2°, 5.68±0.2°, 9.48±0.2°, 10.08±0.2°, 10.44±0.20, 11.42±0.2°, 11.84±0.2°, 12.86±0.2°, 13.62±0.2°, 14.24±0.2°, 14.74±0.2°, 16.08±0.2°, 22.16±0.2°, 24.14±0.2°, 24.82±0.2°, 25.94±0.2°, 27.02±0.2°, 28.84±0.2°, 31.82±0.2°;

e) a racemic-(±)-1-cyclopropyl-6-fluoro-8-methoxy-7-(4-amino-3,3-dimethylpiperidin-1-yl)-1,4-dihydro-4-oxo-quinoline-3-carboxylic acid mesylate polymorph B-1 exhibiting the following X-ray diffraction pattern
(2θ): 5.80±0.2°, 8.08±0.2°, 9.08±0.2°, 12.92±0.2°, 14.70±0.2°, 16.48±0.2°, 17.40±0.2°, 18.36±0.2°, 18.74±0.2°, 19.60±0.2°, 20.44±0.2°, 20.94±0.2°, 21.50±0.2°, 22.80±0.2°, 23.28±0.2°, 23.84±0.2°, 24.36±0.2°, 25.50±0.2°, 26.00±0.2°, 26.78±0.2°, 27.24±0.2°, 29.22±0.2°, 30.66±0.2°, 37.58±0.2°;

f) a R-(+)1-cyclopropyl-6-fluoro-8-methoxy-7-(4-amino-3,3-dimethylpiperidin-1-yl)-1,4-dihydro-4-oxo-quinoline-3-carboxylic acid mesylate polymorph B-1 exhibiting the following X-ray diffraction pattern
(2θ): 5.74±0.2°, 8.02±0.2°, 9.02±0.2°, 12.84±0.2°, 14.74±0.2°, 16.46±0.2°, 17.32±0.2°, 18.38±0.2°, 19.58±0.2°, 20.38±0.2°, 20.92±0.2°, 21.48±0.2°, 22.80±0.2°, 23.80±0.2°, 24.28±0.2°, 25.62±0.2°, 26.88±0.2°, 27.32±0.2°, 28.20±0.2°, 29.16±0.2°, 30.68±0.20;

g) a S-(−)-1-cyclopropyl-6-fluoro-8-methoxy-7-(4-amino-3,3-dimethylpipendin-1-yl)-1,4-dihydro-4-oxo-quinoline-3-carboxylic acid mesylate polymorph B-1 exhibiting the following X-ray diffraction pattern
X-ray powder diffraction (2θ): 8.02±0.2°, 12.84±0.2°, 14.70±0.2°, 16.44±0.2°, 17.30±0.2°, 19.56±0.2°, 20.90±0.2°, 21.46±0.2°, 23.76±0.2°, 25.56±0.2°, 27.30±0.2°, 30.66±0.2°, 37.46±0.2°;

h) a racemic (±)-1-cyclopropyl-6-fluoro-8-methoxy-7-(4-amino-3,3-dimethylpiperidin-1-yl)-1,4-dihydro-4-oxo-quinoline-3-carboxylic acid mesylate polymorph B-2 exhibiting the following X-ray diffraction pattern
(2θ): 9.40±0.2°, 9.94, 10.74±0.2°, 12.32±0.2°, 12.98±0.2°, 14.02±0.2°, 15.72±0.2°, 16.92±0.2°, 18.84±0.2°, 19.38±0.2°, 20.52±0.2°, 21.20±0.2°, 22.80, 22.96±0.2°, 24.64±0.2°, 25.54±0.2°, 28.38±0.2°, 29.92±0.2°, 30.72±0.2°, 35.92, 37.88±0.2°;

i) a R-(+)-1-cyclopropyl-6-fluoro-8-methoxy-7-(4-amino-3,3-dimethylpiperldin-1-yl)-1,4-dihydro-4-oxo-quinoline-3-carboxylic acid mesylate polymorph B-2 exhibiting the following X-ray diffraction pattern
(2θ): 8.04±0.2°, 9.36±0.2°, 10.06±0.2°, 10.84±0.2°, 12.24±0.2°, 12.88±0.2°, 13.94±0.2°, 15.26±0.2°, 15.75±0.2°, 16.82±0.2°, 17.16±0.2°, 18.78±0.2°, 19.62±0.2°, 20.42±0.2°, 21.22±0.2°, 22.30±0.2°, 23.16±0.2°, 24.26±0.2°, 24.62±0.2°, 25.54±0.2°, 28.38±0.2°, 30.00±0.2°, 30.84±0.2°, 38.18±0.2°;

j) a S-(−)-1-cyclopropyl-6-fluoro-8-methoxy-7-(4amino-3,3-dimethylpiperidin-1-yl)-1,4-dihydro-4-oxo-quinoline-3-carboxylic acid mesylate polymorph B-2 exhibiting the following X-ray diffraction pattern
(2θ): 9.38±0.2°, 10.04±0.2°, 12.28±0.2°, 12.94±0.2°, 13.98±0.2°, 15.78±0.2°, 16.86±0.2°, 18.80±0.2°, 19.62±0.2°, 21.24±0.2°, 22.39±0.2°, 23.18±0.2°, 24.64±0.2°, 25.56±0.2°, 28.44±0.2°, 30.02±0.2°, 30.90±0.2°, 39.74±0.2°.

2. The compound according to claim 1 corresponding to polymorph A-3 of racemic (±)-1-cyclopropyl-6-fluoro-8-methoxy-7-(4-amino-3,3-dimethylpiperidin-1-yl)-1,4-dihydro-4-oxo-quinoline-3-carboxylic acid hydrochloride.

3. The compound according to claim 1 corresponding to polymorph A-3 of R-(+)-1-cyclopropyl-6-fluoro-8-methoxy-7-(4-amino-3,3-dimethylpiperidin-1-yl)-1,4-dihydro-4-oxo-quinoline-3-carboxylic acid hydrochloride.

4. The compound according to claim 1 corresponding to polymorph A-3 of S-(−)-1-cyclopropyl-6-fluoro-8-methoxy-7-(4-amino-3,3-dimethylpiperidin-1-yl)-1,4-dihydro-4-oxo-quinoline-3-carboxylic acid hydrochloride.

5. The compound according to claim 1 corresponding to polymorph A-4 of S-(−)-1-cyclopropyl-6-fluoro-8-methoxy-7-(4-amino-3,3-dimethylpiperidin-1-yl)-1,4-dihydro-4-oxo-quinoline-3-carboxylic acid hydrochloride.

6. The compound according to claim 1 corresponding to polymorph B-1 of racemic (±)-1-cyclopropyl-6-fluoro-8-methoxy-7-(4-amino-3,3-dimethylpiperidin-1-yl)-1,4-dihydro-4-oxo-quinoline-3-carboxylic acid mesylate.

7. The compound according to claim 1 corresponding to polymorph B-1 of R-(+)-1-cyclopropyl-6-fluoro-8-methoxy-7-(4-amino-3,3-dimethylpiperidin-1-yl)-1,4-dihydro-4-oxo-quinoline-3-carboxylic acid mesylate.

8. The compound according to claim i corresponding to polymorph B-1 of S-(−)-1-cyclopropyl-6-fluoro-8-methoxy-7-(4-amino-3,3-dimethylpiperidin-1-yl)-1,4-dihydro-4-oxo-quinoline-3-carboxylic acid mesylate.

9. The compound according to claim 1 corresponding to polymorph B-2 of racemic (±)-1-cyclopropyl-6-fluoro-8-methoxy-7-(4-amino-3,3-dimethylpiperidin-1-yl)-1,4-dihydro-4-oxo-quinoline-3-carboxylic acid mesylate.

10. The compound according to claim 1 corresponding to polymorph B-2 of R-(+)-1-cyclopropyl-6-fluoro-8-methoxy-7-(4-amino-3,3-dimethylpiperidin-1-yl)-1,4-dihydro-4-oxo-quinoline-3-carboxylic acid mesylate.

11. The compound according to claim 1 corresponding to polymorph B-2 of S-(−)1-cyclopropyl-6-fluoro-8-methoxy-7-(4-amino-3,3-dimethylpiperidin-1-yl)-1,4-dihydro-4-oxo-quinoline-3-carboxylic acid mesylate.

12. A process for preparing polymorph A-3 of racemic (±)-1-cyclopropyl-6-fluoro-8-methoxy-7-(4-amino-3,3-dimethylpiperidin-1-yl)-1,4-dihydro-4-oxo-quinoline-3-carboxylic acid hydrochloride exhibiting the X-ray diffraction pattern
(2θ): 5.32±0.2°, 5.68±0.2°, 9.42±0.2°, 10.06±0.2°, 10.40±0.2°, 11.40±0.2°, 11.78±0.2°, 12.98±0.2°, 13.74±0.2°, 14.38±0.2°, 14.66±0.2°, 16.02±0.2°, 22.59±0.2°, 23.74±0.2°, 24.48±0.2°, 25.22±0.2°, 27.36±0.2°, 28.74±0.2°, 31.28±0.2°, 31.72±0.2°;
which process comprises the steps of
a) drying polymorphic A-1 form of racemic (±)-1-cyclopropyl-6-fluoro-8-methoxy-7-(4-amino-3,3-dimethylpiperidin-1-yl)-1,4-dihydro-4-oxo-quinoline-3-carboxylic acid hydrochloride at an elevated temperature, preferably 130° C. up to 150° C., optionally under reduced pressure sufficient to effect transformation to polymorphic form A-3; and
b) recovering the polymorphic form A-3 as a crystalline solid.

13. A process for preparing polymorph A-3 of racemic (±)-1-cyclopropyl-6-fluoro-8-methoxy-7-(4-amino-3,3-dimethylpiperidin-1-yl)-1,4-dihydro-4-oxo-quinoline-3-carboxylic acid hydrochloride, exhibiting the X-ray diffraction pattern
(2θ): 5.32±0.2°, 5.68±0.2°, 9.42±0.2°, 10.06±0.2°, 10.40±0.2°, 11.40±0.2°, 11.78±0.2°, 12.98±0.2°, 13.74±0.2°, 14.38±0.2°, 14.66±0.2°, 16.02±0.2°, 22.52±0.2°, 23.74±0.2°, 24.48±0.2°, 25.22±0.2°, 27.36±0.2°, 28.74±0.2°, 31.28±0.2°, 31.72±0.2°;

which process comprises the steps of:
 a) drying polymorphic A-2 form of racemic (±)-1-cyclopropyl-6-fluoro-8-methoxy-7-(4-amino-3,3-dimethylpiperidin-1-yl)-1,4-dihydro-4-oxo-quinoline-3-carboxylic acid hydrochloride at an elevated temperature, preferably 130° C. up to 150° C., optionally under reduced pressure sufficient to effect transformation to polymorphic form A-3; and
 b) recovering the polymorphic form A-3 as a crystalline solid.

14. A process for preparing polymorph A-3 of R-(+)-1-cyclopropyl-6-fluoro-8-methoxy-7-(4-amino-3,3-dimethylpiperidin-1-yl)-1,4-dihydro-4-oxo-quinoline-3-carboxylic acid hydrochloride exhibiting the X-ray diffraction pattern
 (2θ): 5.34±0.2°, 5.70±0.2°, 9.46±0.2°, 10.08±0.2°, 10.44±0.2°, 11.42±0.2°, 11.82±0.2°, 12.86±0.2°, 13.62±0.2°, 14.26±0.2°, 14.72±0.2°, 16.08±0.2°, 22.16±0.2°, 23.68±0.2°, 24.18±0.2°, 24.86±0.2°, 25.98±0.2°, 27.04±0.2°, 28.84±0.2°, 31.56±0.2°, 31.84±0.2°;

which process comprises the steps of
 a. drying polymorphic A-1 form of R-(+)-1-cyclopropyl-6-fluoro-8-methoxy-7-(4-amino-3,3-dimethylpiperidin-1-yl)-1,4-dihydro-4-oxo-quinoline-3-carboxylic acid hydrochloride at an elevated temperature, preferably 130° C. up to 150° C., optionally under reduced pressure sufficient to effect transformation to polymorphic form A-3; and
 b. recovering the polymorphic form A-3 as a crystalline solid.

15. A process for preparing polymorph A-3 of R-(+)-1-cyclopropyl-6-fluoro-8-methoxy-7-(4-amino-3,3-dimethylpiperidin-1-yl)-1,4-dihydro-4-oxo-quinoline-3-carboxylic acid hydrochloride exhibiting the X-ray diffraction pattern
 (2θ): 5.34±0.2°, 5.70±0.2°, 9.46±0.2°, 10.08±0.2°, 10.44±0.2°, 11.42±0.2°, 11.82±0.2°, 12.86±0.2°, 13.62±0.2°, 14.26±0.2°, 14.72±0.2°, 16.08±0.2°, 22.16±0.2°, 23.68±0.2°, 24.18±0.2°, 24.86±0.2°, 25.98±0.2°, 27.04±0.2°, 28.84±0.2°, 31.56±0.2°, 31.84±0.2°;

which process comprises the steps of
 a) drying polymorphic A-2 form of R-(+)-1-cyclopropyl-6-fluoro-8-methoxy-7-(4-amino-3,3-dimethylpiperidin-1-yl)-1,4-dihydro-4-oxo-quinoline-4-carboxylic acid hydrochloride at an elevated temperature, preferably 130° C. up to 150° C., optionally under reduced pressure sufficient to effect transformation to polymorphic form A-3; and
 b) recovering the polymorphic form A-3 as a crystalline solid.

16. A process for preparing polymorph A-4 of S-(−)-1-cyclopropyl-6-fluoro-8-methoxy-7-(4-amino-3,3-dimethylpiperidin-1-yl)-1,4-dihydro-4-oxo-quinoline-3-carboxylic acid hydrochloride, exhibiting the X-ray diffraction pattern
 (2θ): 5.34±0.2°, 5.68±0.2°, 9.48±0.2°, 10.08±0.2°, 10.44±0.2°, 11.42±0.2°, 11.84±0.2°, 12.86±0.2°, 13.62±0.2°, 14.24±0.2°, 14.74±0.2°, 16.08±0.2°, 22.16±0.2°, 24.14±0.2°, 24.82±0.2°, 25.94±0.2°, 27.02±0.2°, 28.84±0.2°, 31.82±0.2°;

which process comprises the steps of:
 a) drying polymorphic A-3 form of S-(−)-1-cyclopropyl-6-fluoro-8-methoxy-7-(4-amino-3,3dimethylpiperidin-1-yl)-1,4-dihydro-4-oxo-quinoline-3-carboxylic acid hydrochloride at an elevated temperature, preferably 130° C. up to 150° C., optionally under reduced pressure sufficient to effect transformation to polymorphic form A-4; and
 b) recovering the polymorphic form A-4 as a crystalline solid.

17. A process for preparing polymorph A-3 of S-(−)-1-cyclopropyl-6-fluoro-8-methoxy-7-(4-amino-3,3-dimethylpiperidin-1-yl)-1,4-dihydro-4-oxo-quinoline-3-carboxylic add hydrochloride exhibiting the X-ray diffraction pattern
 (2θ): 7.04±0.2°, 7.70±0.2°, 8.06±0.2°, 12.34±0.2°, 12.78±0.2°, 13.64±0.2°, 15.40±0.2°, 16.14±0.2θ, 18.62±0.2°, 19.40±0.2°, 20.64±0.2°, 21.84±0.2°, 23.22±0.2°, 26.80±0.2°, 27.88±0.2°, 29.86±0.2°, 32.30±0.2°, 33.36±0.2°, 37.02±0.2°, 39.24±0.2°;

which process comprises the steps of
 a) suspending or dissolving polymorphic form A-1 of S-(−)-1-cyclopropyl-6-fluoro-8-methoxy-7-(4-amino-3,3-dimethylpiperidin-1-yl)-1,4-dihydro-4-oxo-quinoline-3-carboxylic acid hydrochloride in water, if necessary by heating;
 b) stirring the mixture to form a suspension or a solution followed by adding a water-miscible organic solvent;
 c) recovering the polymorphic form A-3 as a crystal upon cooling the solution and filtrating; and
 d) drying resultant crystals to constant weight to provide the polymorph A-3.

18. A process for preparing polymorph A-3 of S-(−)-1-cyclopropyl-6-fluoro-8-methoxy-7-(4-amino-3,3-dimethylpiperidin-1-yl)-1,4-dihydro-4-oxo-quinoline-3-carboxylic acid hydrochloride exhibiting the X-ray diffraction pattern
 (2θ): 7.04±0.2°, 7.70±0.2°, 8.06±0.2°, 12.34±0.2°, 12.78±0.2°, 13.64±0.2°, 15.40±0.2°, 16.14±0.2°, 18.62±0.2°, 19.40±0.2°, 20.64±0.2°, 21.84±0.2°, 23.22±0.2°, 26.80±0.2°, 27.88±0.2°, 29.86±0.2°, 32.30±0.2°, 33.36±0.2°, 37.02±0.2°;

which process comprises the steps of:
 a) suspending or dissolving polymorphic form A-2 of S-(−)-1-cyclopropyl-6-fluoro-8-methoxy-7-(4-amino-3,3-dimethylpiperidin-1-yl)-1,4-dihydro-4-oxo-quinoline-3carboxylic acid hydrochloride in water, if necessary by heating;
 b) adding a water-miscible organic solvent and stirring resulting mixture for a sufficient period of time to effect the transformation completely to polymorphic form A-3;
 c) recovering the polymorphic form A-3 as a crystal upon cooling the solution and filtering; and
 d) drying the resultant crystals to a constant weight to yield the product A-3.

19. A process for preparing polymorph A-3 of S-(−)-1-cyclopropyl-6-fluoro-8-methoxy-7-(4-amino-3,3-dimethylpiperidin-1-yl)-1,4-dihydro-4-oxo-quinoline-3-carboxylic acid hydrochloride, from said polymorphs A-1 or A-2 or A-4 which process comprises
 a) suspending or dissolving polymorphic form A-1 or A-2 or A-4 of S-(−)-1-cyclopropyl-6-fluoro-8-methoxy-7-(4-amino-3,3-dimethylpiperidin-1-yl)-1,4-dihydro-4-oxo-quinoline-3-carboxylic acid hydrochloride in water, if necessary by heating;
 b) stirring the mixture at that temperature to form a suspension or a solution followed by adding a water-miscible organic solvent;
 c) recovering the polymorphic form A-3 as a crystal upon cooling the solution and filtrating;
 d) drying the resultant crystals to a constant weight to yield the product of the invention.

20. A process for preparing polymorph B-1 of racemic (±)-1-cyclopropyl-6-fluoro-8-methoxy-7-(4-amino-3,3-dimethylpiperidin-1-yl)-1,4-dihydro-oxo-quinoline-3-carboxylic acid mesylate, which comprises
 a) suspending or dissolving racemic (±)-1-cyclopropyl-6-fluoro-8-methoxy-7-(4-amino-3,3-dimethylpiperidin-1-yl)-1,4-dihydro-4-oxo-quinoline-3-carboxylic acid in a suitable organic solvent to form a suspension/solution;
 b) heating the suspension/solution and adding methane sulfonic acid at the elevated temperature;
 c) heating the reaction mixture at elevated temperature sufficient to effect transformation to the mesylate polymorphic form B-1;
 d) recovering the polymorphic form B-1 as a crystal upon cooling the solution and filtering;
 e) drying crystals to a constant weight to yield the polymorph B-1 of the invention.

21. A process for preparing polymorph B-1 of R-(+)-1-cyclopropyl-6-fluoro-8-methoxy-7-(4-amino-3,3-dimethylpiperidin-1-yl)-1,4-dihydro-4-oxo-quinoline-3-carboxylic acid mesylate, which comprises
 a) suspending or dissolving R-(+)-1-cyclopropyl-6-fluoro-8-methoxy-7-(4-amino-3,3-dimethylpiperidin-1-yl)-1,4-dihydro-4-oxo-quinoline-3-carboxylic acid in a suitable organic solvent to form a suspension/solution;
 b) heating the suspension/solution and adding methane sulfonic acid at the elevated temperature;
 c) heating the reaction mixture at elevated temperature sufficient to effect transformation to the mesylate polymorphic form B-1;
 d) recovering the polymorphic form B-1 as a crystal upon cooling the solution and filtering;
 e) drying crystals to a constant weight to yield the polymorph B-1 of the invention.

22. A process for preparing polymorph B-1 of S-(−)-1-cyclopropyl-6-fluoro-8-methoxy-7-(4-amino-3,3-dimethylpiperidin-1-yl)-1,4-dihydro-4-oxo-quinoline-3-carboxylic acid mesylate, which comprises
 a) suspending or dissolving (−)-1-cyclopropyl-6-fluoro-8-methoxy-7-(4-amino-3,3-dimethylpiperidin-1-yl)-1,4-dihydro-4-oxo-quinoline-3-carboxylic acid in a suitable organic solvent to form a suspension/solution;
 b) heating the suspension/solution and adding methane sulfonic acid at the elevated temperature;
 c) heating the reaction mixture at elevated temperature sufficient to effect transformation to the mesylate polymorphic form B-1;
 d) recovering the polymorphic form B-1 as a crystal upon cooling the solution and filtering;
 e) drying crystals to a constant weight to yield the polymorph B-1 of the invention.

23. A process for preparing polymorph B-2 of racemic (±)-1-cyclopropyl-6-fluoro-8-methoxy-7-(4-amino-3,3-dimethylpiperidin-1-yl)-1,4-dihydro-4-oxo-quinoline-3-carboxylic acid mesylate, which comprises
 a) dissolving crystalline polymorphic form B-1 of racemic (±)-1-cyclopropyl-6-fluoro-8-methoxy-7-(4-amino-3,3-dimethylpiperidin-1-yl)-1,4-dihydro-4-oxo-quinoline-3-carboxylic acid mesylate in water by heating to form a solution;
 b) cooling the solution and adding an aqueous-miscible organic solvent;
 c) allowing the reaction mixture to stand for a sufficient time to effect transformation to polymorphic form B-2,
 d) recovering the polymorphic form B-2 as a crystal upon cooling and filtering;
 e) drying resultant crystals to a constant weight to yield the polymorph B-2 of the invention.

24. A process for preparing polymorph B-2 of R-(+)-1-cyclopropyl-6-fluoro-8-methoxy-7-(4-amino-3,3-dimethylpiperidin-1-yl)-1,4-dihydro-4-oxo-quinoline-3-carboxylic acid mesylate, which comprises
 a) dissolving crystalline polymorphic form B-1 of R-(+)-1-cyclopropyl-6-fluoro-8-methoxy-7-(4-amino-3,3-dimethylpiperidin-1-yl)-1,4-dihydro-4-oxo-quinoline-3-carboxylic acid mesylate in water by heating to form a solution;
 b) cooling the solution and adding an aqueous-miscible organic solvent;
 c) allowing the reaction mixture to stand for a sufficient time to effect transformation to polymorphic form B-2,
 d) recovering the polymorphic form B-2 as a crystal upon cooling and filtering;
 e) drying resultant crystals to a constant weight to yield the polymorph B-2 of the invention;
 f) A process for preparing polymorph B-2 of S-(−)-1-cyclopropyl-6-fluoro-8-methoxy-7-(4-amino-3,3-dimethylpiperidin-1-yl)-1,4-dihydro-4-oxo-quinoline-3-carboxylic acid mesylate, which comprises
 g) dissolving crystalline polymorphic form B-1 of S-(−)-1-cyclopropyl-6-fluoro-8-methoxy-7-(4-amino-3,3-dimethylpiperidin-1-yl)-1,4-dihydro-4-oxo-quinoline-3-carboxylic acid mesylate in water by heating to form a solution;
 h) cooling the solution and adding an aqueous-miscible organic solvent;
 i) allowing the reaction mixture to stand for a sufficient time to effect transformation to polymorphic form B-2,
 j) recovering the polymorphic form B-2 as a crystal upon cooling and filtering;
 k) drying resultant crystals to a constant weight to yield the polymorph B-2 of the invention.

* * * * *